(12) United States Patent
Lathrop et al.

(10) Patent No.: US 7,998,160 B2
(45) Date of Patent: Aug. 16, 2011

(54) LANCING DEVICES HAVING LANCET EJECTION ASSEMBLY

(75) Inventors: Ray Adams Lathrop, Atlanta, GA (US); John Andrew Trissel, Canton, GA (US); Stephen J. Flynn, Peachtree City, GA (US); Samuel Mason Curry, San Francisco, CA (US); Bradley Koeppel, Smyrna, GA (US)

(73) Assignees: Abbott Diabetes Care Inc., Alameda, CA (US); Facet Technologies, LLC, Kennesaw, GA (US)

( * ) Notice: Subject to any disclaimer, the term of this patent is extended or adjusted under 35 U.S.C. 154(b) by 0 days.

(21) Appl. No.: 12/955,166

(22) Filed: Nov. 29, 2010

(65) Prior Publication Data
US 2011/0087134 A1 Apr. 14, 2011

Related U.S. Application Data

(62) Division of application No. 11/755,322, filed on May 30, 2007, now Pat. No. 7,867,244.

(60) Provisional application No. 60/877,215, filed on Dec. 26, 2006, provisional application No. 60/813,904, filed on Jun. 15, 2006.

(51) Int. Cl.
*A61B 17/14* (2006.01)
(52) U.S. Cl. .................................. 606/181
(58) Field of Classification Search .............. 606/181, 606/182, 183; 604/136, 137, 138, 139; 600/566, 600/567, 583
See application file for complete search history.

(56) References Cited

U.S. PATENT DOCUMENTS

| | | | | |
|---|---|---|---|---|
| 4,442,836 A * | 4/1984 | Meinecke et al. | ............ | 606/182 |
| 4,895,147 A * | 1/1990 | Bodicky et al. | ............ | 606/182 |
| 5,318,584 A * | 6/1994 | Lange et al. | ............ | 606/182 |
| 5,423,847 A * | 6/1995 | Strong et al. | ............ | 606/182 |
| 6,045,567 A * | 4/2000 | Taylor et al. | ............ | 606/181 |
| 6,197,040 B1 * | 3/2001 | LeVaughn et al. | ............ | 606/182 |
| 6,346,114 B1 * | 2/2002 | Schraga | ............ | 606/182 |
| 6,602,268 B2 * | 8/2003 | Kuhr et al. | ............ | 606/181 |
| 7,452,366 B2 * | 11/2008 | Chen et al. | ............ | 606/181 |
| 2003/0050656 A1 * | 3/2003 | Schraga | ............ | 606/182 |
| 2003/0225430 A1 * | 12/2003 | Schraga | ............ | 606/182 |
| 2004/0186500 A1 * | 9/2004 | Koike et al. | ............ | 606/181 |
| 2004/0260325 A1 * | 12/2004 | Kuhr et al. | ............ | 606/181 |
| 2005/0125019 A1 * | 6/2005 | Kudrna et al. | ............ | 606/182 |
| 2005/0234492 A1 * | 10/2005 | Tsai et al. | ............ | 606/181 |
| 2005/0251188 A1 * | 11/2005 | Chen et al. | ............ | 606/181 |
| 2006/0206135 A1 * | 9/2006 | Uehata et al. | ............ | 606/181 |
| 2009/0069832 A1 * | 3/2009 | Kitamura et al. | ............ | 606/181 |
| 2009/0143810 A1 * | 6/2009 | Kitamura et al. | ............ | 606/182 |
| 2009/0228035 A1 * | 9/2009 | Kitamura et al. | ............ | 606/181 |
| 2009/0275968 A1 * | 11/2009 | Kitamura et al. | ............ | 606/182 |
| 2009/0299398 A1 * | 12/2009 | Yoritaka et al. | ............ | 606/182 |

* cited by examiner

*Primary Examiner* — Anhtuan Nguyen
*Assistant Examiner* — Jonathan W Miles
(74) *Attorney, Agent, or Firm* — Young Basile

(57) ABSTRACT

A lancing device is provided for use with a removable lancet. The lancing device includes a housing and a lancet carrier slidably disposed within the housing and adapted to receive the lancet. A user-actuated ejection slide is mounted to the housing to eject the lancet from the lancet carrier. A locking member is pivotally mounted to the housing. As the ejection slide moves forward, it rotates the locking member to block forward movement of the lancet carrier during ejection. The locking member is configured so that substantially all of the force exerted on it by the lancet carrier is transmitted to the housing via the pivotal mounting.

18 Claims, 49 Drawing Sheets

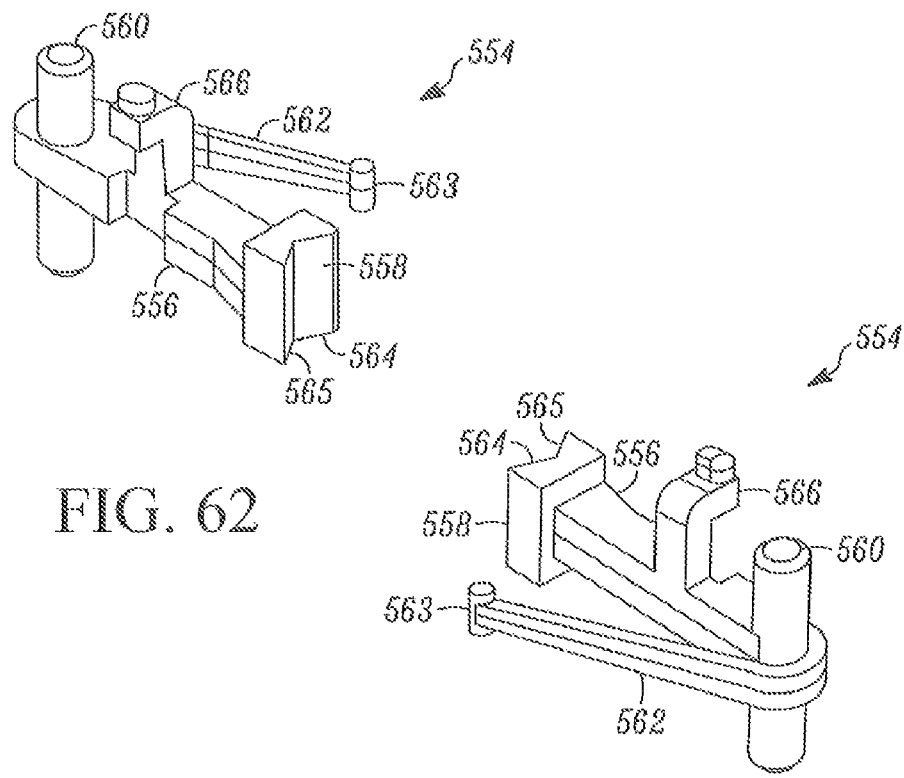
FIG. 62
FIG. 63
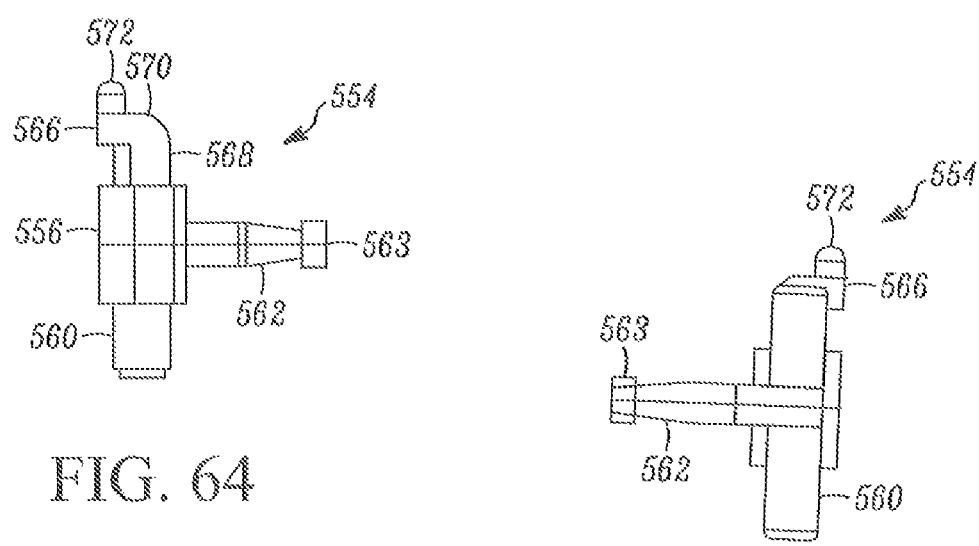
FIG. 64
FIG. 65

LANCING DEVICES HAVING LANCET EJECTION ASSEMBLY

CROSS REFERENCE TO CO-PENDING APPLICATIONS

This Application is a divisional of U.S. patent application Ser. No. 11/755,322 filed on May 30, 2007 and claims the benefit of the filing date of U.S. Provisional Patent Application Ser. No. 60/813,904 filed Jun. 15, 2006 and U.S. Provisional Patent Application Ser. No. 60/877,215 filed Dec. 26, 2006, the entire contents of all being incorporated herein by reference.

BACKGROUND

Lancing devices are typically handheld units that permit users to draw blood for testing and diagnostic purposes. These devices include a housing with a piercing aperture, a lancet that contains one or more needles, and a firing mechanism. The firing mechanism typically includes a spring or other biasing means which can be cocked either by insertion of the lancet or by pulling a cocking handle, for example. Once the lancing device is cocked, it is placed against the user's skin, often the fingertip. The user can then press a trigger to actuate the firing mechanism, which momentarily drives the sharp tip of the needle through the piercing aperture to puncture the user's skin and draw blood. When the lancing operation is complete, the user can press a second actuator to eject the lancet for removal and disposal.

A consideration in the design of lancets is to minimize the discomfort experienced by users during the lancing process. To this end, some lancing devices include mechanisms to adjust the distance that the needle sharp protrudes through the piercing aperture, thus regulating the depth that the needle penetrates the user's skin. In some cases, these depth adjustment mechanisms include adjustable stops that limit the forward movement of the lancet during firing. In other cases, depth adjustment mechanisms adjust the tip of the lancing device to reduce or increase the distance that the needle sharp protrudes from the lancing device. One approach for depth adjustment is illustrated in U.S. Pat. No. 5,984,940. A lancet holder is moved axially within a lancing device housing to move the needle closer to or farther away from the piercing aperture, thus adjusting penetration depth.

Another consideration in the design of lancing devices is to avoid accidental needle pricks when inserting and removing lancets from the lancing device. To this end, lancets include safety features such as frangible tabs which cover the needle sharp prior to insertion in the lancing device. Once the lancet is inserted, the use can break off and remove the frangible tab. Some lancets also include sleeves coaxially mounted to the main body of the lancet. The sleeve can be positioned so that it protectively encloses the needle sharp. During the lancing operation, the main body of the lancet slides through the sleeve to expose the lancet sharp. After removal of the lancet, however, the sleeve can be locked in its protective position, reducing the likelihood that a person handling the use lancet will prick himself or herself.

Lancing devices can draw blood from a user's fingertip or other body part. A fingertip is a good testing site because it contains a large number of blood vessels and it is therefore easy to draw an adequate quantity of blood from the fingertip. However, fingertips are also sensitive and users who must frequently draw blood samples may experience discomfort from repeated sampling of the fingertips. Therefore, some users also perform lancing operations on parts of the body, and this is known as alternate site testing or alternate site incision, also known as "AST."

To effectively draw blood from an alternate site, it is helpful to have the needle penetrate the skin more deeply. It is also helpful to have a relatively wide piercing aperture. A wider piercing aperture acts as an expression ring by allowing the skin to pucker into the aperture's opening and by compressing a wider area of skin around the incision. When skin protrudes through the aperture into the housing, it is also more deeply penetrated by the lancet.

A piercing aperture that is suitably wide for AST lancing may be too wide for finger testing. Thus, some lancing devices provide removable endcaps with different size piercing apertures. A user attaches one endcap (with a wider piercing aperture) when the lancing device is used for AST lancing; and a different endcap (with a more narrow piercing aperture) when the lancing device is used for fingertip lancing.

Another approach has been proposed in which the piercing aperture is adjustable in size, as illustrated in US Patent Application Publication Number 2004/0236251. The smaller size is used during the incision, whether on a finger tip or alternate site. Once the incision is made, the piercing aperture is expanded to provide a larger opening that can be used to express the desired quantity of blood from an alternate site. The size of the piercing aperture can be adjusted by moving a reference member into the piercing aperture, effectively obstructing the opening and providing a flat surface against which the user's skin (finger tip or alternate site) is pressed for lancing. After the incision is made, the reference member is retracted to provide an unobstructed, relatively wide expression opening.

It has also been proposed that the reference member be attached to the lancet itself. During incision, the lancet and the reference member are moved together toward the piercing aperture to effectively narrow the piercing aperture. After incision, the reference member and the lancet are retracted to leave the piercing aperture unobstructed. Prior to the lancet's insertion into the lancing device, the reference member can be adjusted relative to the lancet for purposes of regulating the penetration depth of the needle.

Another consideration in the design of lancing systems is the ease with which a lancet can be inserted into the lancing device. It is known that when a lancet is inserted into a lancing device, the force of the insertion can be used to cock the device. However, if the device is already cocked, and a lancet was to be inserted, there is some risk that the device would discharge during the insertion process and the user would be accidentally pricked. It is also known to provide a removable cap on the housing to permit insertion of the lancet. However, this requires an additional step in the process (namely, removing the cap). It would be desirable to provide a lancing device that can be loaded without removal of the cap and that could not be loaded when cocked.

Another consideration in the design of lancets is to minimize the handling of the lancet by the user during ejection of the lancet from the lancing device. To this end, it is known to provide ejection mechanisms that include a sliding member that engages the lancet to push it out of the lancing device. In such cases, it is helpful to restrain the lancet carrier from forward movement. Known mechanisms for achieving this use the sliding member to actuate a releasable connector to engage the lancet carrier and prevent its forward movement, as shown for example in U.S. Pat. No. 6,197,040. The releasable connector is biased towards the ejection slide and away from the lancet carrier and is configured so that when the lancet carrier is urged forward, a force vector is transmitted through the connector to the ejection slide. This means that the slide and the ejector rub against each other with a degree of force, causing friction that is discernable to the user. It would be desirable to provide an ejection mechanism that minimizes friction and force imposed on moving parts to reduce wear.

SUMMARY

In accordance with some embodiments, a lancing device is provided for use with a removable lancet. The lancing device comprises a housing, a lancet carrier slidably disposed within the housing and adapted to receive the lancet; an ejection slide mounted to the housing and configured to eject the lancet from the lancet carrier; and a locking member cooperating with the ejection slide to move into blocking engagement with the lancet carrier when the ejection slide ejects the lancet. The locking member contacts the housing on one or more bearing surfaces apart from the ejection slide. The locking member is configured so that substantially all of the force exerted on it by the lancet carrier is transmitted to the housing via the one or more bearing surfaces.

In accordance with other embodiments, a lancing device is provided for use with a removable lancet. The lancing device includes a housing; a lancet carrier slidably disposed within the housing and adapted to receive the lancet; an ejection slide mounted to the housing and configured to eject the lancet from the lancet carrier; and a locking member cooperating with the ejection slide to move into blocking engagement with the lancet carrier when the ejection slide ejects the lancet. The locking member and lancet carrier are configured so that forward thrust of the lancet carrier urges the locking member to remain in blocking engagement with the lancet carrier when the ejection slide ejects the lancet.

In accordance with other embodiments, a lancing device is provided for use with a removable lancet having a needle terminating in a sharp tip and a sleeve disposed about at least a portion of needle for sliding movement between a forward position in which the sharp tip is protectively surrounded by the sleeve and a rearward position in which the sharp tip projects from the sleeve. The lancing device includes a housing; a lancet carrier slidably disposed within the housing and adapted to receive the lancet; a user-actuated ejection slide mounted to the housing and configured to eject the lancet from the lancet carrier; and a locking member. The locking member has at least a first end and a pivot mounted to the housing. The locking member engages the user-actuated ejection slide to move the first end about the pivot and into blocking engagement with the lancet carrier when the user-actuated slide ejects the lancet. A receiver holds the sleeve stationery relative to the needle and has an elongated axial slot to receive the second member. The locking member is configured so that substantially all of the force exerted on it by the lancet carrier is transmitted to the housing via the pivot.

BRIEF DESCRIPTION OF THE DRAWINGS

The description herein makes reference to the accompanying drawings wherein like reference numerals refer to like parts throughout the several views, and wherein:

FIG. 47b is a side elevation of the cap of the lancing device shown in FIG. 47a;

FIG. 62 is a front perspective view of the locking member of FIGS. 60a and 60b;

FIG. 63 is a rear perspective view of a locking member of FIG. 62;

FIG. 64 is a front elevation of the locking member of FIG. 62;

FIG. 65 is rear elevation of the locking member of FIG. 62;

FIG. 70 is an isolated perspective view of the trigger and locking member of FIG. 60a;

DETAILED DESCRIPTION OF THE EMBODIMENTS

Overview

Figure 1:
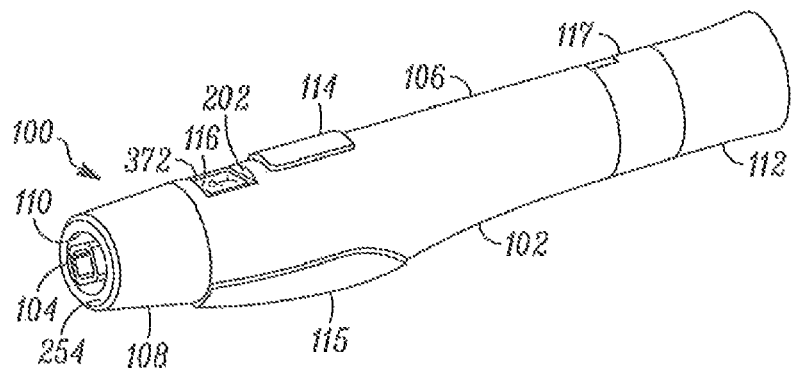
FIG. 1 is a perspective view of a lancing device in accordance with one embodiment of the invention, including a removable lancet inserted therein.

Referring to FIGS. 1-4, a lancing system 100 in accordance with an embodiment of the invention is illustrated, including a lancing device 102 and removable lancet 104. As explained below, lancing system 100 is operated by a user to draw a sample of blood or other bodily fluid from the body such as for diagnostic purposes. Lancing device 102 includes a housing 106 with a skin-engaging cap 108 having a piercing aperture 110, a cocking handle 112 used to cock an internal firing mechanism (described below with reference to FIGS. 30a-30d), a trigger 114 for firing the internal firing mechanism, and an ejection slide 115 to eject lancet 104 from lancing device 102 after use.

Lancing device 102 includes an alternative site testing ("AST") mode actuator ring 116, a user-actuated assembly or user-controlled actuator which the user may rotate to switch lancing device 102 from a finger mode (in which lancing device 102 is well-suited for drawing blood from the user's fingertip) to AST mode (in which lancing device 102 is well suited for drawing blood from part of a user's body other than a fingertip).

Lancing device 102 includes a depth adjuster 117, which the user may rotate to limit the forward axial movement of lancet 104 relative to the skin-engaging surface of cap 108, and thereby limit the depth that lancet 104 penetrates a user's skin.

Figure 3:
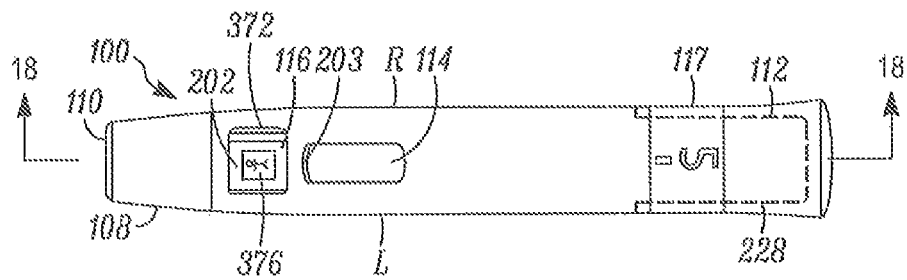
FIG. 3 is top plan view of the lancing device of FIG. 1.
Figure 4:
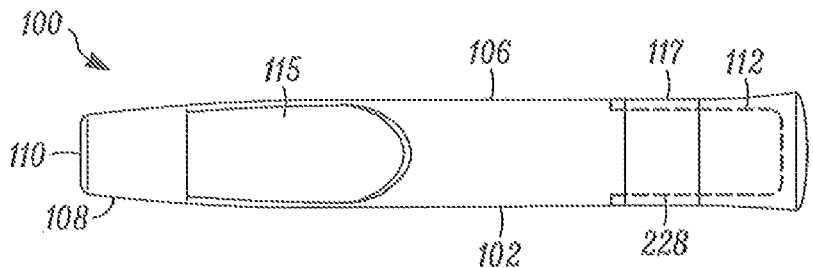
FIG. 4 is a bottom plan view of the lancing device of FIG. 1.

In this specification, unless otherwise provided, the terms "forward" and "front" mean toward the skin-engaging longitudinal end of lancing device 102, and "rear" and "rearward" mean toward longitudinal end of lancing device 102 opposite the skin-engaging end; and term "left" means the left side L of lancing device 102 and the term "right" means the right side R of lancing device 102 (as shown in FIG. 3).

Figure 5:
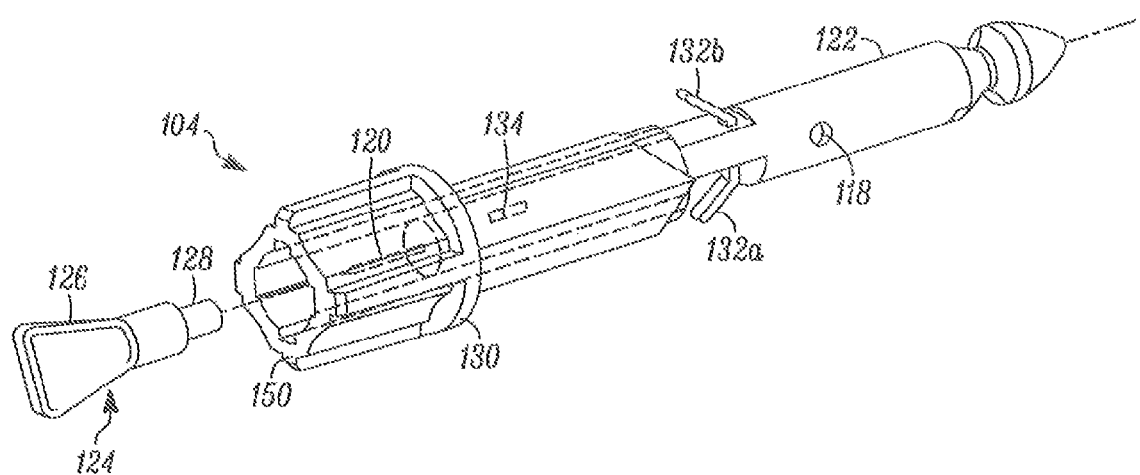
FIG. 5 is a perspective view of a lancet for use with the lancing device of FIG. 1, including a removable tab and a sleeve in an extended position to protectively surround the lancet's needle.
Figure 6:
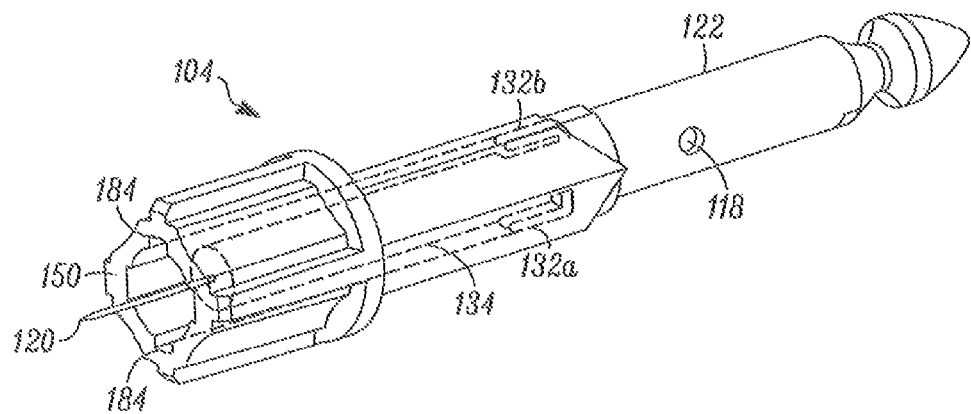
FIG. 6 is a perspective view of the lancet of FIG. 5 showing the sleeve moved to a rearward position to expose the needle's sharp tip.

As shown in FIGS. 5 and 6, lancet 104 includes a needle 118 whose length (excluding a sharp tip 120) is encased in an elongated lancet body 122. A removable tab 124 includes a flange 126 and an elongated stem 128 that encases the sharp tip 120 of needle 118. Stem 128 is frangibly attached to the front end of lancet body 122. A sleeve 130 slides axially over a portion of the lancet body 122 between forward position (as shown in FIG. 5), in which it protectively surrounds the sharp tip 120 of needle 118, and a rearward position (as shown in FIG. 6) in which a portion of sharp tip 120 protrudes beyond the front end of sleeve 130.

The general operation of lancing system 100 is illustrated in FIGS. 7a-7d. Beginning in FIG. 7a, the user inserts lancet 104 into lancing device 102 through piercing aperture 110. Removable tab 124 (shown in FIG. 7a with phantom lines seen through the user's thumb) provides a convenient fingergrip while also protecting the user from exposure to sharp tip 120 and maintains the sterility of the sharp tip 120.

Firm insertion of lancet 104 may cock lancing device 102 (e.g., in AST mode). After initial use, lancing device 102 may also be cocked by pulling cocking handle 112 (see FIG. 1). The mechanisms for cocking lancing device 102 are explained below.

Figure 7A:
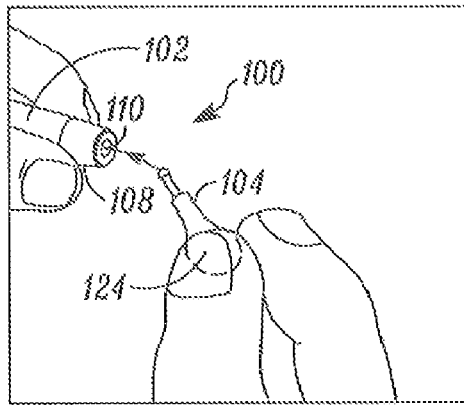
FIGS. 7a through 7d are a series of diagrams showing the general operation of the lancing device and lancet of FIGS. 1-6.
Figure 7B:
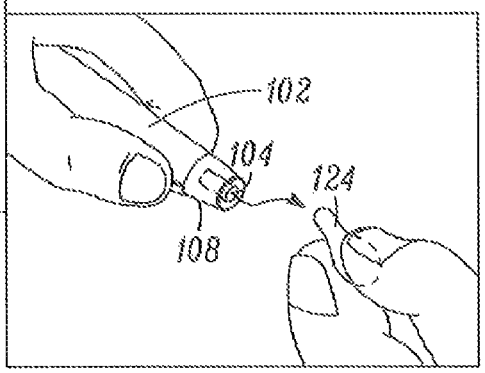

Once lancet 104 is fully inserted, removable tab 124 extends from piercing aperture 110. Referring to FIG. 7b, the user then twists the removable tab 124 to sever it from lancet body 122 along their frangible connection and pulls removable tab 124 off of sharp tip 120. At this time, sharp tip 120 is enclosed within cap 108. Once removable tab 124 is removed, substantially all of lancet 104 can be enclosed by cap 108 of housing 106, so that no part of lancet 104 protrudes beyond piercing aperture 110 by an amount sufficient to displace the user's skin from the skin engaging surface of cap 108.

With lancet 104 inserted into lancing device 102 and lancing device 102 having been cocked, the user places the front surface of sleeve 130 of skin-engaging cap 108 onto his or her finger or other body part and presses trigger 114. The depression of trigger 114 actuates a firing mechanism within housing 106 (described below) to momentarily thrust needle 118 forward through piercing aperture 110.

Figure 7C:
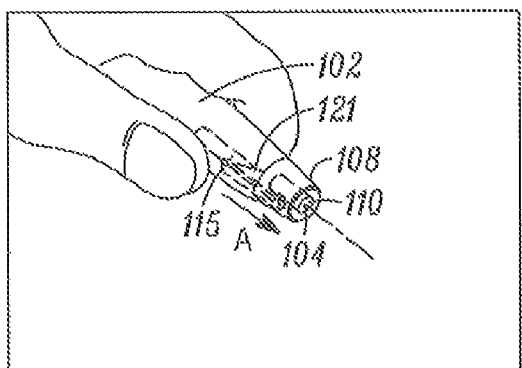

Referring to FIG. 7c, after lancing device 102 is fired, the user slides ejection slide 115 on the underside of housing 106 in the direction of arrow A to partially eject lancet 104 through piercing aperture 110 of cap 108. The mechanisms for ejection are described below with reference to FIGS. 45 and 46. As the user slides ejection slide 115 in the direction of arrow A, the ejection slide engages an ejection actuator 121 inside housing (shown in FIG. 7c with phantom lines; see also FIGS. 45 and 46) to push lancet sleeve 130 into its forward position relative to lancet body 122 so that lancet sleeve 130 surrounds sharp tip 120 in a protective closure (as shown in FIG. 5) and the front-most portion of lancet sleeve 130 projects out of piercing aperture 110 for withdrawing engagement by a user's finger tips. Lancet 104 can also be expelled from lancet device 102 by force of gravity after operation of ejection slide 115, without the user having to touch lancet 104.

Figure 7D:
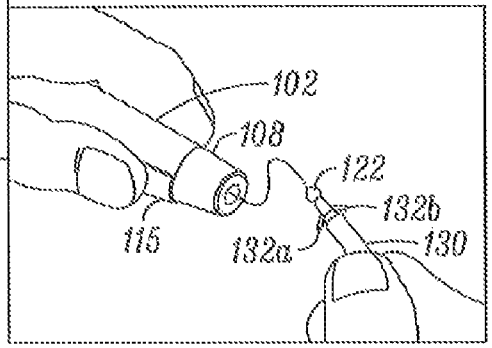

As shown in FIG. 7d, grasping the lancet sleeve 130, the user removes lancet 104 from lancing device 102. Upon ejection, lancet sleeve 130 is locked into its protective position by the extension of locking members or wings 132a, 132b from lancet body 122 (as shown in FIG. 5), thus reducing the possibility the a user will accidentally prick himself or herself on sharp tip 120.

Lancing system 100 can also be used in a kit which includes test strips and an analyzer. After lancing system 100 is operated to draw blood, the user applies the bead of blood to the test strip and inserts the test strip into the analyzer for assessment of blood composition, such as levels of glucose.
Lancet Referring to FIGS. 8-16, the construction of lancet 104 is described, beginning with lancet body 122. Guidance ribs 134 are formed on the top and bottom sides of lancet body 122 near its front end. Guidance ribs 134 extend radially from lancet body 122, with the elongated extent of guidance ribs 134 running parallel to the major axis of lancet body 122.

The diameter of lancet body 122 tapers to form a conical rear end 136 and a neck 138 which define there between a mounting bulb 140.

Wing wells 142a and 142b are formed in left and right lateral surfaces of lancet body 122, respectively, near the mid-section of lancet body 122. Extending from each wing well 142a, 142b is one of locking members, or wings 132a, 132b. Each of wings 132a, 132b has a short, stiff base portion 144 extending radially out from lancet body 122 and a planar flexion member 146 having a wingtip 148 extending in generally forward direction but at an acute angle, which in this case is illustrated as approximately 45° away from the major axis of the lancet body 122 when in the extended configuration. Wings 132a, 132b may be molded as part of lancet body 122.

Figure 8:
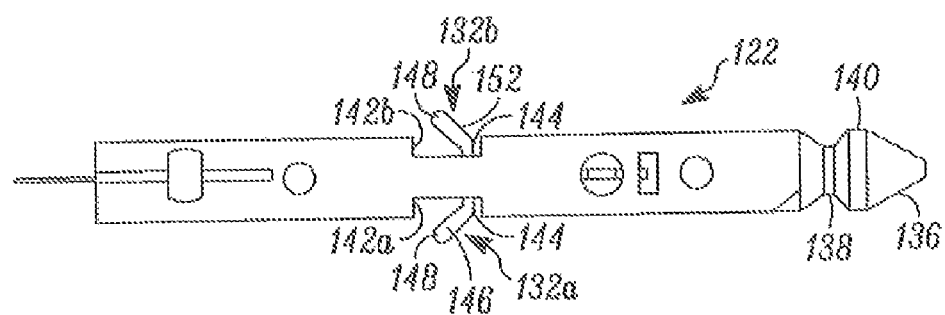
FIG. 8 is a top plan view of the lancet body of the lancet of FIG. 5.
Figure 9:
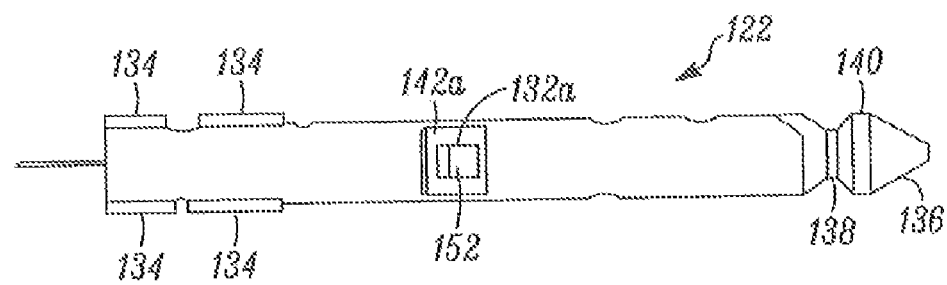
FIG. 9 is a left side view of the lancet body of FIG. 8.

Wings 132a, 132b can flap into a retracted configuration by folding planar flexion members 146 from their extended position shown in FIG. 8 to a retracted position in which flexion member 146 is folded forward by approximately 45° so that flexion member 146 is substantially disposed within its corresponding one of wing wells 142a, 142b. Planar flexion members 146 are flexible and resilient in that they can be folded into wing wells 142a, 142b under the influence of a lateral force, but will return to their outward extended configuration when that force is removed.

Other suitable locking members may be used as an alternative to wings 132a, 132b. These other suitable locking members include, but are not limited to, pivoting members that pivot rather than fold into the wing wells, studs that extend out from the lancet body that can be pushed into a retracted position into a well in the lancet body, or barbs.

Figure 93A:
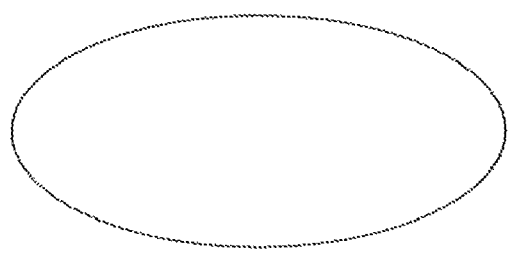
FIGS. 93a-c are front-view perspectives of the sleeve with a cross section that is one of ovular, circular, and polygonal.
Figure 93B:
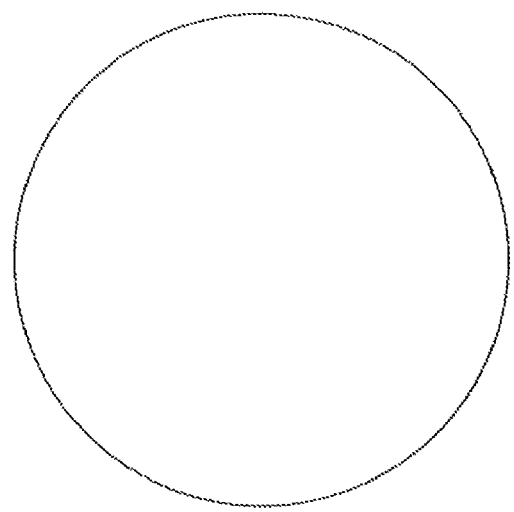
Figure 93C:
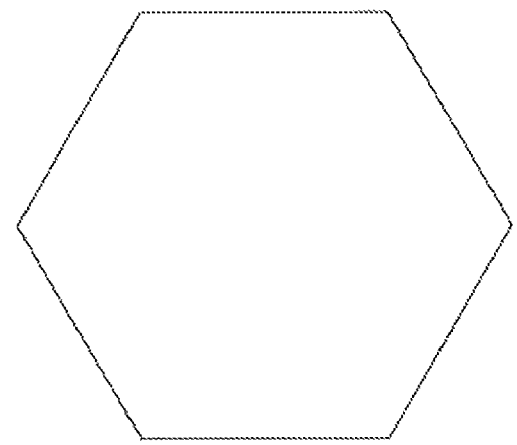

FIGS. 10-16 illustrate lancet sleeve 130 in more detail. Sleeve 130 is generally tubular in construction with a front end 150 and a rear end 152 and defining an elongated inner chamber 154 there between. Sleeve 130 is divided into a front portion 156 and a rear portion 158. Four outer guidance ribs 160a through 160d project radially from the front portion 156 of sleeve 130 at 90° intervals, extending along the longitudinal extent of front portion 156. Front ends 162a through 162d of guidance ribs 160a-160d have a slight bevel. Although sleeve 130 is tubular, sleeve 130 can be made with different sectional shapes or slots (to reduce the material used to manufacture sleeve 130). In additional embodiments, the sleeve 130 has a cross section that is one of polygonal, circular and ovular, as shown in FIGS. 93a-c.

An annular flange 164 circumscribes sleeve 130 between its front portion 156 and rear portion 158. The front face of annular flange 164 defines a mounting shoulder 166 and the rear face of annular flange 164 defines an ejection shoulder 168. As further explained below, mounting shoulder 166 provides a surface permitting a receiver 170 (see FIG. 17) that is internal to housing 106 to engage sleeve 130, and ejection shoulder 168 provides a surface for ejection actuator 121 (also internal to housing 106; see FIGS. 17 and 18) to engage sleeve 130.

Figure 42:
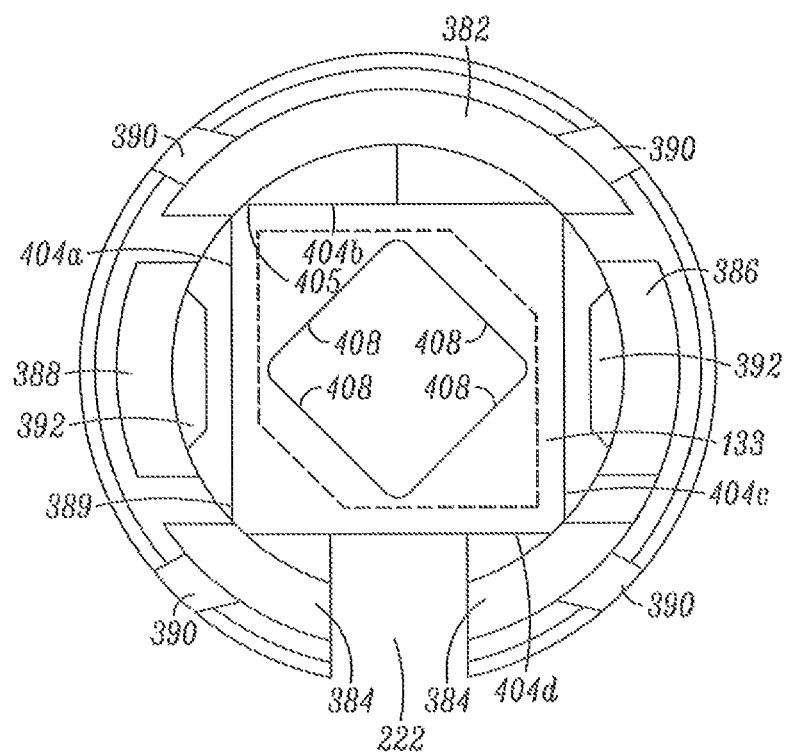
FIG. 42 is a front view of the receiver and lancet (shown in phantom lines) of FIG. 40.
Figure 43:
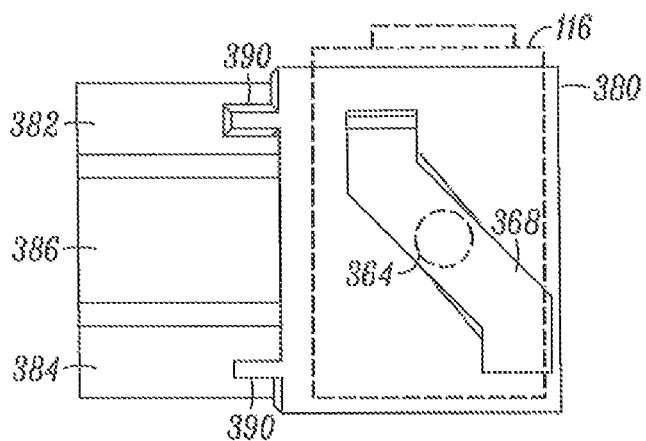
FIG. 43 is a left side view of the receiver of FIG. 38.

In rear portion 158, sleeve 130 is generally hexagonal in cross section (except for its rear end 152, as explained below) and defines lower planar faces 172a and 172f, upper planar faces 172c and 172d and lateral planar faces 172b and 172e. Lateral planar faces 172b and 172e can be used during manufacturing to position sleeve for installation on lancet body. Also, as explained below, when lancet 104 is inserted into receiver 170, lower planar faces 172a and 172f and upper planar faces 172c and 172d mate with corresponding surfaces inside receiver 170 to orient lancet 104 within lancing device 102, as shown in FIG. 42.

Figure 13:
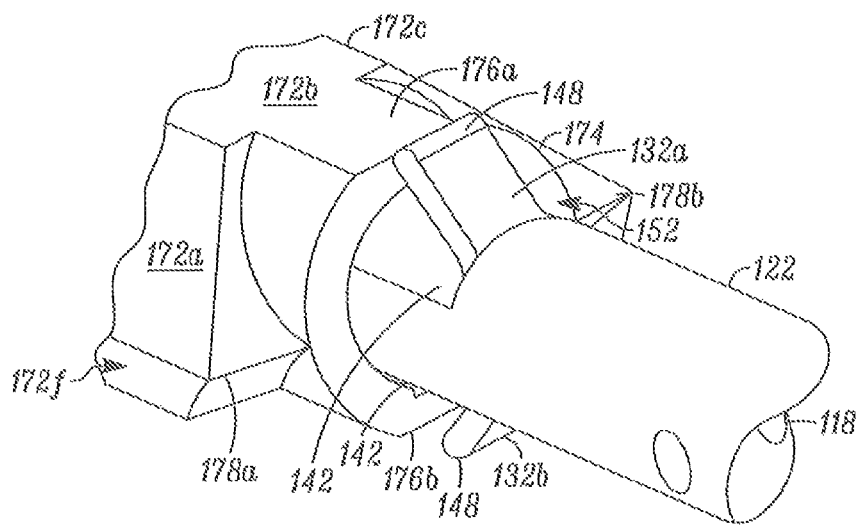
FIG. 13 is a isolated perspective view showing detail of the lancet of FIG. 5, including the rear end of the sleeve and the wings on the lancet body that prevent rearward movement of the sleeve relative to the lancet body.

As best seen in FIG. 13, the exterior shape of sleeve 130 at its rear end 152 is that of a cylinder 174 with its top and bottom surfaces sheared off to form planar surfaces 176a and 176b. Planar surfaces 176a and 176b are contiguous with lateral planar faces 172b and 172e, respectively. Lower planar surfaces 172a and 172f terminate in beveled corner 178a on the left side of cylinder 174 and upper planar surfaces 172c and 172d terminate in beveled corner 178b on the right side of cylinder 174. Beveled corners 178a, 178b act as guiding surfaces to rotate lancet sleeve 130 into its proper orientation as it is inserted into receiver 170.

Figure 14:
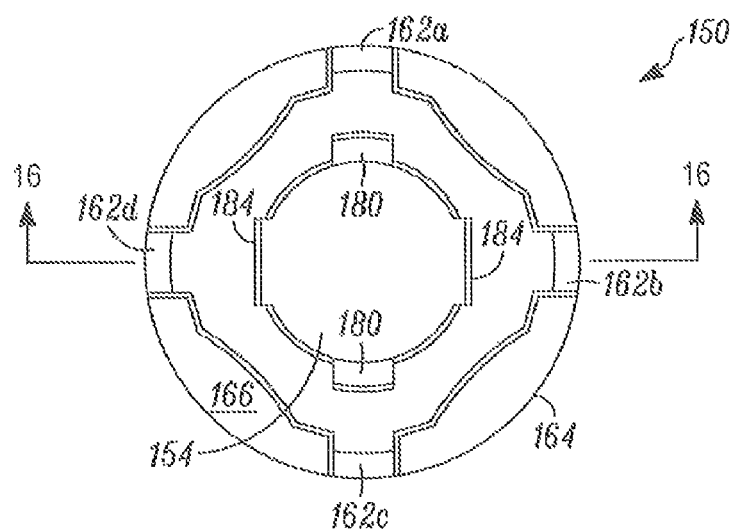
FIG. 14 is a front view of the lancet sleeve of FIG. 10.
Figure 15:
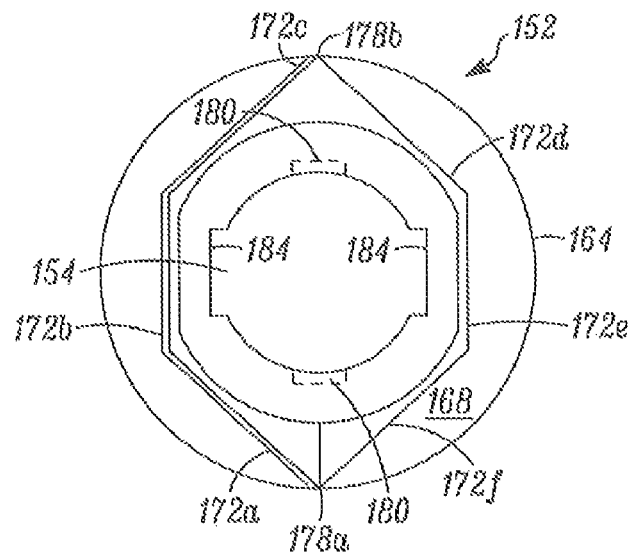
FIG. 15 is rear view of the lancet sleeve of FIG. 10.
Figure 16:
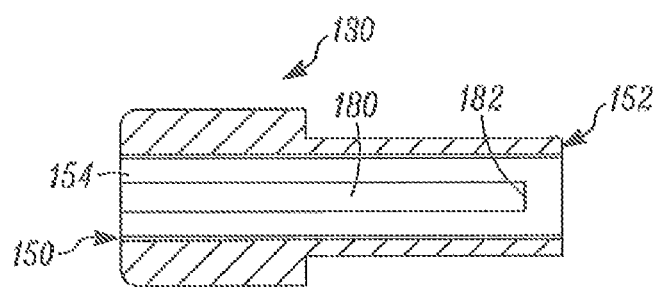
FIG. 16 is a cross-sectional view of the lancet sleeve of FIG. 10 taken along the lines 16-16 in FIG. 14.

The inner chamber 154 of sleeve 130 is sized and configured to allow lancet body 122 to be snugly coaxially disposed within sleeve 130. The sleeve 130 has a width of less than 5 mm. As best seen in FIGS. 14-16, inner chamber 154 is generally cylindrical with upper and lower grooves 180 extending longitudinally through sleeve at the top and bottom of inner chamber 154, respectively. Grooves 180 are each sized and positioned to receive guidance ribs 134 of lancet body 122 in sliding engagement. As best seen in the sectional view of FIG. 16, each of grooves 180 extends from front end 150 of sleeve 130 to one of backstops 182 that are displaced from rear end 152 of sleeve 130.

Each of guidance ribs 134 of lancet body 122 fits into one of grooves 180, permitting sleeve 130 to slide axially forward over lancet body 122 to an extended protective position (in which front portion 156 of sleeve 130 surrounds sharp tip 120, as shown in FIG. 5) and backward over lancet body 122 to a retracted position (in which sharp tip 120 extends past the front end 150 of sleeve 130, as shown in FIG. 6). Back stops 182 engage one of rearmost ends of guidance ribs 134 to prevent sleeve 130 from sliding off the front of lancet body 122.

The cylindrical contour of inner chamber 154 is further modified by the inclusion of elongated guide surfaces which are wing engagement surfaces 184, a pair of wide, shallow lateral grooves on opposing lateral sides of sleeve 130 that extend the length of sleeve 130.

The function of wing engagement surfaces 184 is explained as follows. When wings 132a, 132b are in the extended configuration, their wingtips 148 span a distance greater than the diameter of inner chamber 154. If sleeve 130 moves rearward relative to lancet body 122 from its protective extended configuration (shown in FIGS. 5 and 13), wingtips 148, if extended, will engage the rear end 152 of lancet sleeve 130, blocking further rearward movement of sleeve 130 and in effect locking sleeve 130 in its protective extended position, as shown in FIG. 5.

However, when wings 132a, 132b are in their retracted configuration (that is, folded into wing wells 142a, 142b as shown in FIG. 6), they do not extend beyond the diameter of inner chamber 154, so that sleeve 130 can slide axially over the wing wells 142a, 142b without interruption. As sleeve 130 slides over wings 132a, 132b, each of the wings (now folded into wing wells 142a, 142b) brushes along the longitudinal extent of wing engagement surfaces 184, or elongated guide surfaces as shown in FIG. 6. These surfaces contain the locking member or wings 132a, 132b in their retracted configuration when the sleeve 130 moves over the wings.

Sleeve 130 and wings 132a, 132b can be separate components, as shown above, so that sleeve 130 can be in space-apart relation to wings 132a, 132b. This permits sleeve to be moved over a wider range of lancet body 122 to accommodate operation of lancing device 102 in AST and finger modes, as described below.

Note that for simplicity in illustration, the relative axial movement of sleeve 130 and lancet body 122 is described solely in terms of sleeve 130 moving over the body 122. In operation of lancing device 102, most notably during firing of lancet 104, this same relative movement is achieved by moving the lancet body 122 while the sleeve 130 remains stationary. However, the mechanical interaction between sleeve 130 and body 122 in that case is still as described above.

Internal Construction of Lancing Device

Figure 17:
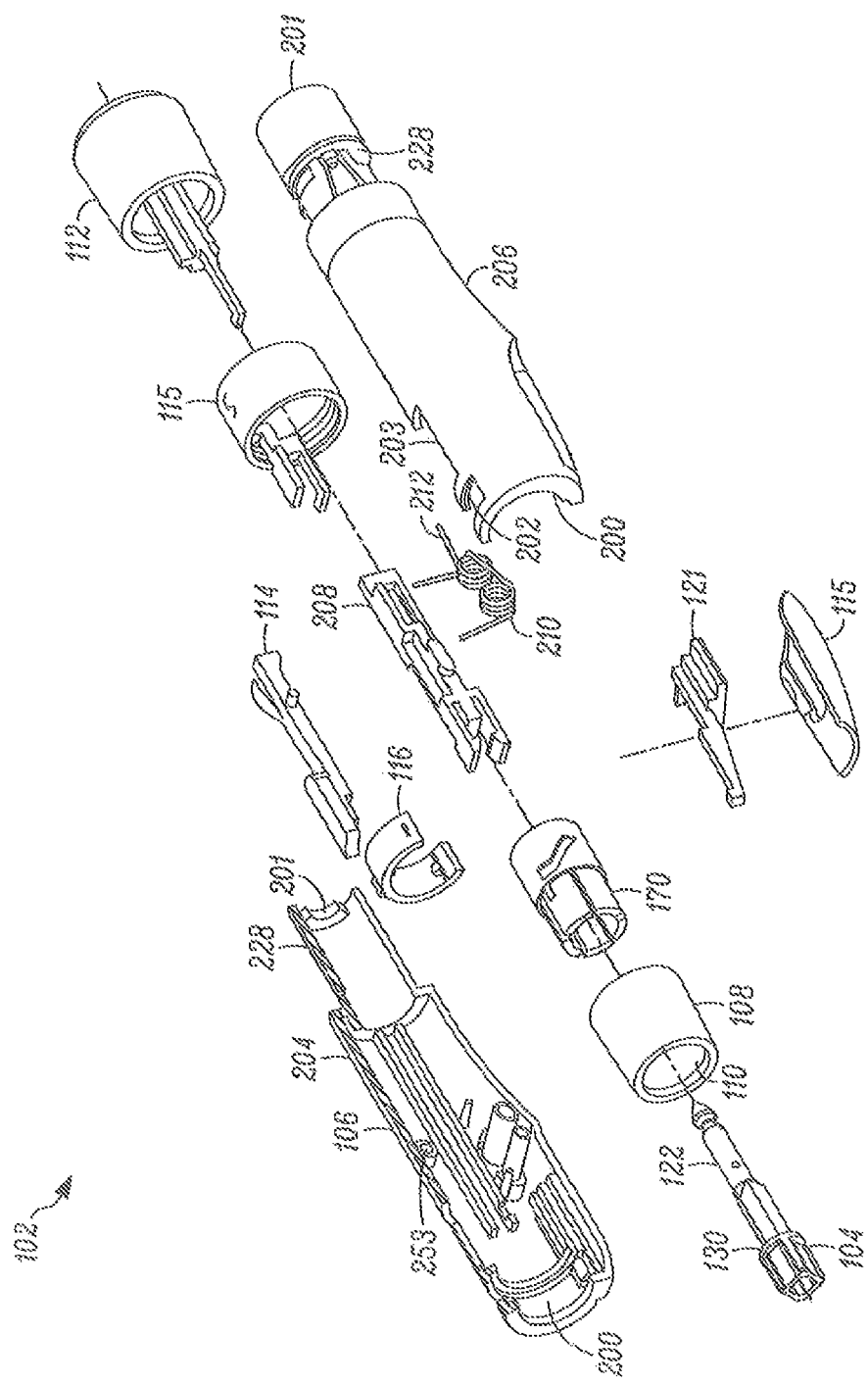
FIG. 17 is an exploded perspective view of the lancing device of FIG. 1.
Figure 18:
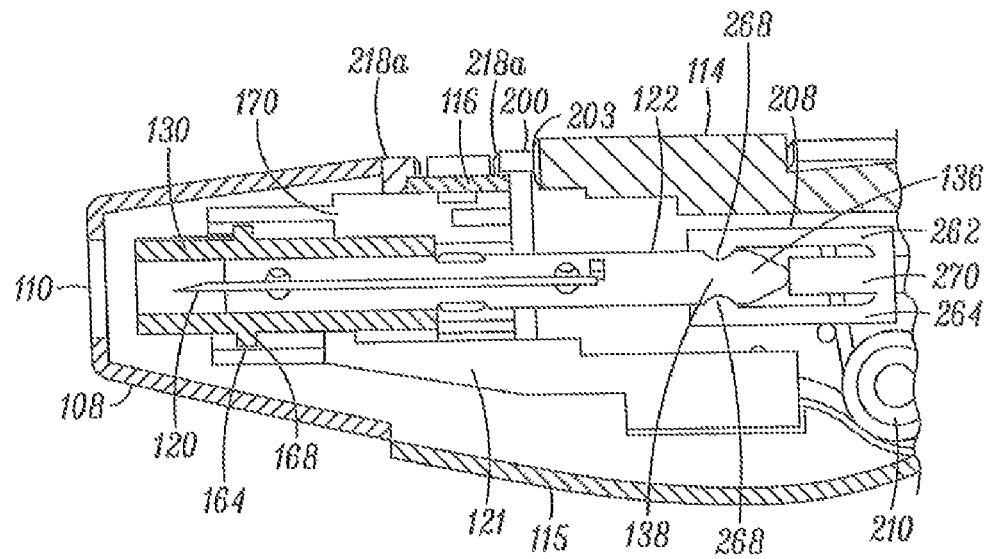
FIG. 18 is a cross-sectional view of the lancing device taken along the lines 18-18 of FIG. 3, including the lancet of FIG. 5 as inserted into the lancing device.

Referring to FIGS. 17 and 18, the internal construction of lancing device 102 is shown. Receiver 170 is coupled to AST mode actuator ring 116 and engages lancet sleeve 130 to move lancet sleeve in response to movement of AST mode actuator ring 116. A slidable lancet carrier 208 engages lancet body 122. A drive spring 210 propels the lancet carrier 208 toward piercing aperture 110 to drive lancet needle 118 to pierce the user's skin or other bodily tissue. A return spring 212 propels lancet carrier 208, removing needle's sharp tip 120 out of the user's skin after piercing. The combination of lancet carrier 208 and at least drive spring 210 acts as a lancet holding assembly to hold and move lancet. An ejection actuator 121 is coupled to ejection slide 115 and ejects lancet 104 from lancing device 102 in response to movement by the user of ejection slide 115. Also located within housing are portions of cocking handle 112 and depth adjuster 117 as described below.

These components of lancing device 102 will now be described.

Housing

Figure 20:
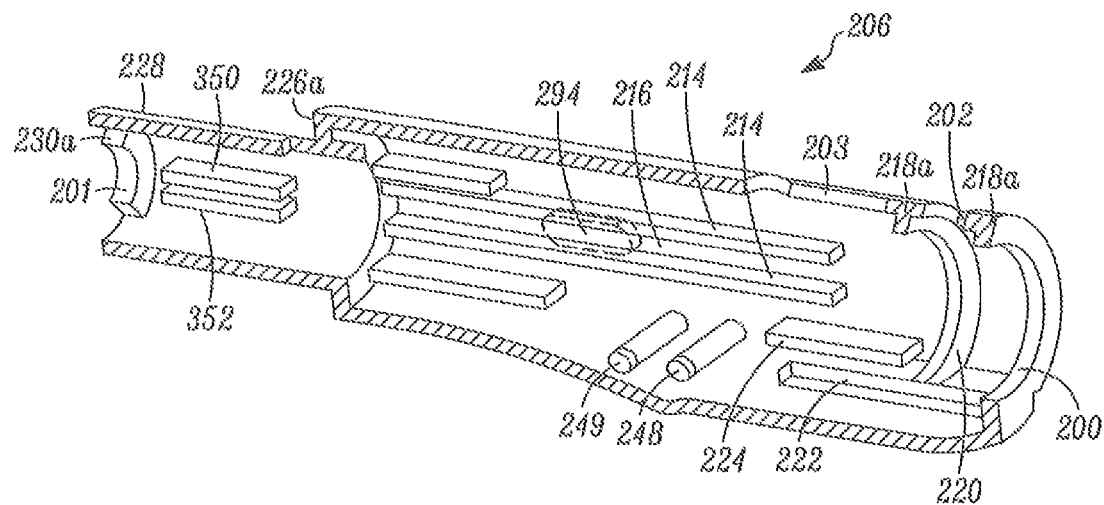
FIG. 20 is a perspective view of the left half of the housing of the lancing device of FIG. 1.
Figure 21:
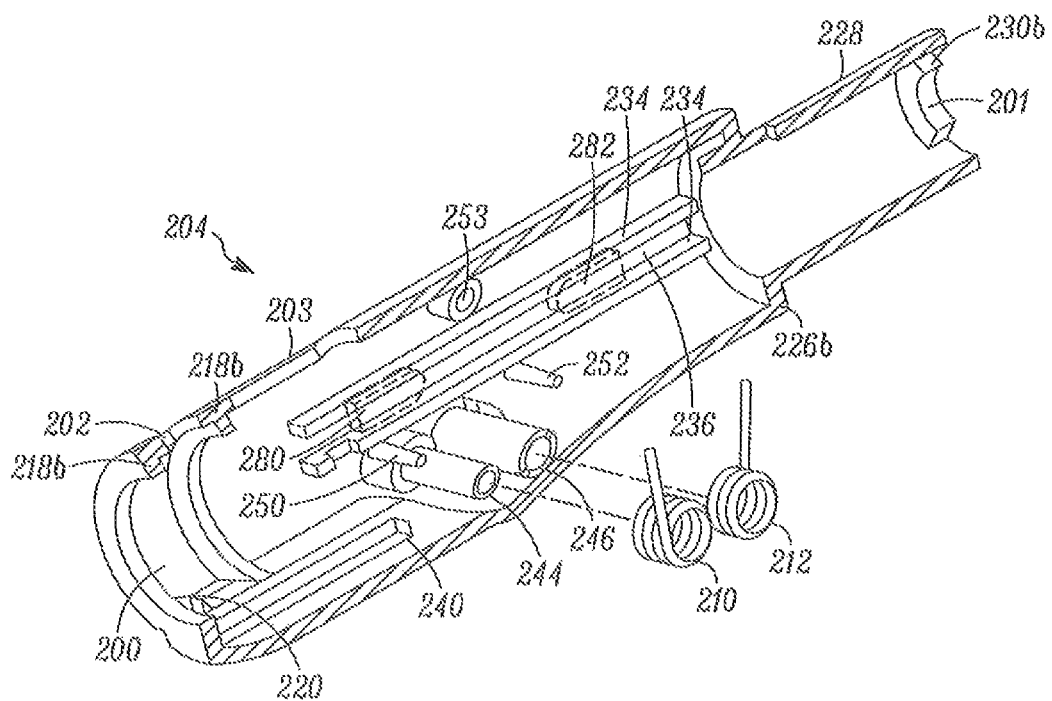
FIG. 21 is a perspective view of the right half of the housing of the lancing device of FIG. 1.

FIGS. 20 and 21 illustrate the construction of housing 106. Housing 106 defines an elongated hollow barrel having a front aperture 200, rear aperture 201, AST mode actuator aperture 202 (through which a portion of AST mode actuator ring 116 extends and trigger aperture 203 (through which a portion of trigger 114 extends). Note that for ease of manufacture, housing 106 may be formed of a conjoined left half 206 and right half 204 as shown in FIGS. 20 and 21, respectively.

Referring to FIG. 20, the left half 206 of housing 106 includes a pair of elongated, spaced-apart guides 214 defining there between a lancet carrier left-hand guide track 216.

Left half 206 also includes near its front end a pair of semi-annular flanges 218a. Flanges 218a define the left half of shoulders 220 that are spaced apart slightly more than the width of AST mode actuator ring 116, so that AST mode actuator ring 116 can be mounted for rotation between shoulders 220 of housing 106, as shown in FIG. 18. The front most of flanges 218a also defines the left half of front aperture 200 of housing 106.

An elongated slot 222 is formed near the lower front end of left half 206. As explained below, elongated slot 222 provides a guide track for ejection actuator 121 as it slides axially to eject lancet 104 from lancing device 102 and also permits intercoupling of ejection slide 115 and ejection actuator 121 through housing 106. Adjacent to and just above elongated slot 222 is an elongated member 224 that functions as an additional guide for the movement of ejection actuator 121.

A rearward portion of left half 206 has a reduced diameter to define a semi-annular rear flange 226a from which extends the left half of a distal mounting portion 228. As best seen in FIG. 1, cocking handle 112 and depth adjustment ring 117 are mounted to distal mounting portion 228. Near the rear end of distal mounting portion 228 is a semi-annular flange 230a defining the left half rear aperture 201, which has a diameter narrower than the rest of mounting portion 228 to provide an annular guide ring for cocking handle 112.

Referring to FIG. 21, right half 204 of housing 106 includes a pair of elongated, spaced-apart guides 234 running along a portion of the upper longitudinal extent of right half 204. Spaced apart guides 234 define there between the lancet carrier right-hand guide track 236.

Right half 204 also includes near its front end a pair of semi-annular flanges 218b aligned with flanges 218a of left half 206. Flanges 218b define the right half of shoulders 220, as explained above in reference to left half 206. The frontmost of flanges 218b also defines the right half of front aperture 200 of housing 106.

An elongated slot 240 for ejection slide 115 and ejection actuator 121 is formed near the lower front end of right half 204. Slot 240 is in alignment with and performs the same function as its counter-part slot 222 of left half 206.

Figure 19:
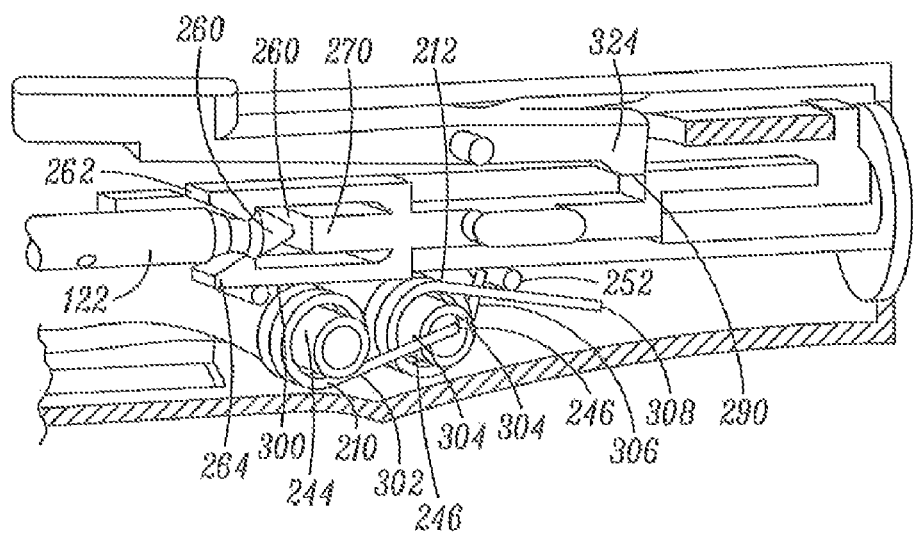
FIG. 19 is a partial perspective view of internal components of the lancing device of FIG. 1 showing drive springs and a portion of the lancet of FIG. 5 as inserted into the device.

Below lancet carrier right hand guide track 236 are positioned a drive spring boss 244 on which drive spring 210 is mounted (as best seen in FIG. 19) and a return spring boss 246 on which return spring 212 is mounted (as best seen in FIG. 19). Each of bosses 244 and 246 is hollow and open ended for mating engagement with its corresponding one of support bosses 248 and 249, respectively, projecting from left half (see FIG. 20).

Positioned forward of and slightly above drive spring boss 244 is a drive spring stop 250 in the form of a finger. Positioned rearward of and slightly above return spring boss 246 is return spring stop 252 also in the form of a finger. The operations of drive spring stop 250 and return spring stop 252 are explained below in reference to FIGS. 30a through 30d.

Positioned near the upper end of right half 204 just rearward of trigger aperture 203, is an open-ended cylindrical trigger pivot well 253, on which trigger 114 is pivotally mounted as described below in reference to FIGS. 27 through 29.

A rearward portion of right half 204 has a reduced diameter to define a semi-annular rear flange 226b from which extends the right half of distal mounting portion 228. Near the rear end of distal mounting portion 228 is a semi-annular flange 230b defining the right half of rear aperture 201 of housing 106.

Cap

Figure 2:
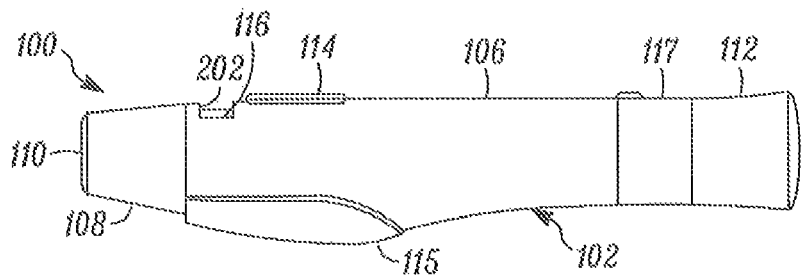
FIG. 2 is a left side view of the lancing device of FIG. 1.
Figure 31:
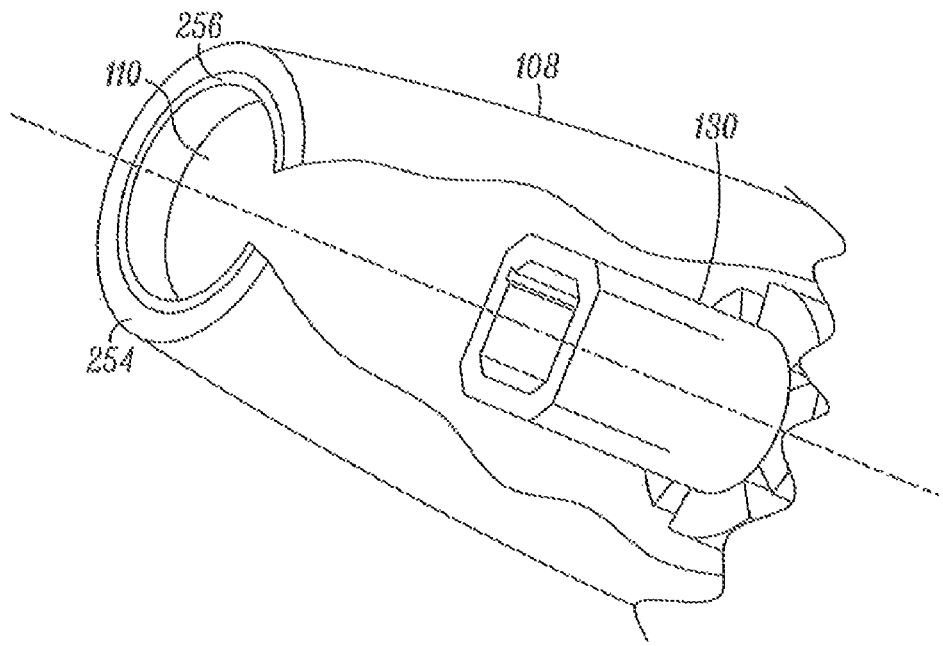
FIG. 31 is an isolated perspective view of the cap of the lancing device of FIG. 1, showing the position of the lancet sleeve when lancing device is in finger mode.

Referring to FIGS. 1 through 3, attached to the front end of housing 106 is cap 108. Cap 108 may be opaque (so that users do not see the sharp tip 120). Cap 108 provides protective closure around sharp tip 120 when lancet 104 is inserted into lancing device 102. Referring to FIG. 31, cap 108 also includes an annular skin-engaging proximal surface 254 that forms a compression ring 256 about piercing aperture 110. Although cap 108 may be constructed in a variety of sizes and configurations, in certain embodiments piercing aperture 110 may be about 5 mm to about 15 mm in diameter and skin-compression ring 256 may have a width of about 1 mm to about 3 mm. The operation of skin-compression ring 256 and piercing aperture 110 will be described as follows in relation to AST mode actuator ring 116. Skin compression ring may be circular or have other shapes and need not be continuous or completely annular.

Cap 108 can be removable from the front end of housing 106 to permit cleaning of the interior of lancing device 102. To permit its removal, cap 108 can be threadably connected to housing 106 or connected via snap fit, for example. However, during operation of lancing device 102 it is not necessary to remove cap 108. Alternatively, cap 108 can be permanently attached to or integrally molded with housing 106. Lancet 104 can be loaded into lancing device through piercing aperture 110 while cap 108 remains attached to housing 106. As explained below, the same cap 108 can be used when lancing device 102 is operated in both finger mode and AST mode. In other words, cap 108 need not be replaced to accommodate use of lancing device in finger and AST modes.

Lancet Carrier

Figure 22:
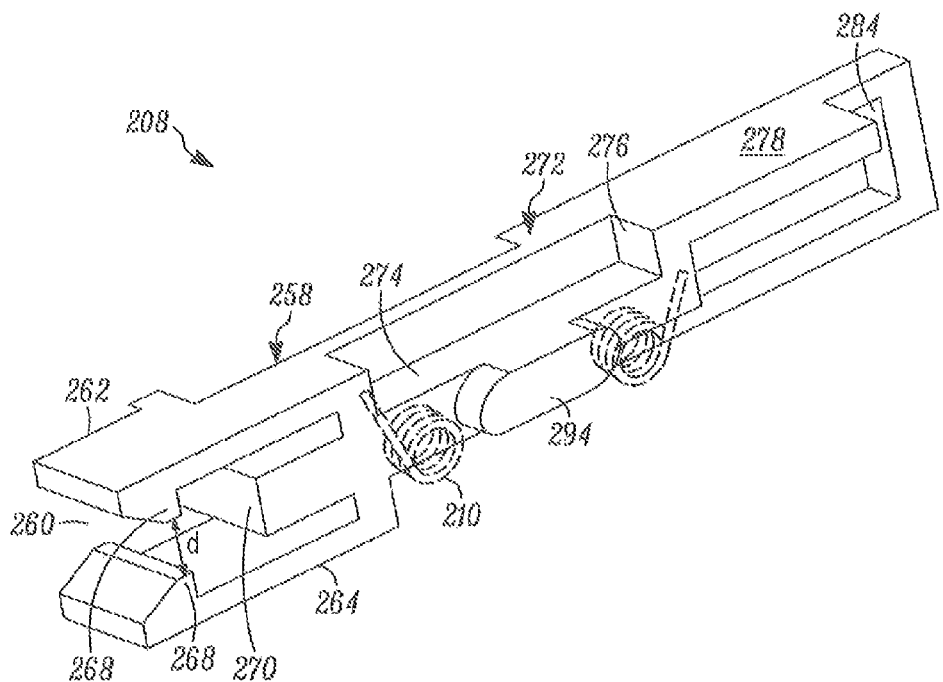
FIG. 22 is a left-front perspective view of the lancet carrier of FIG. 17.
Figure 23:
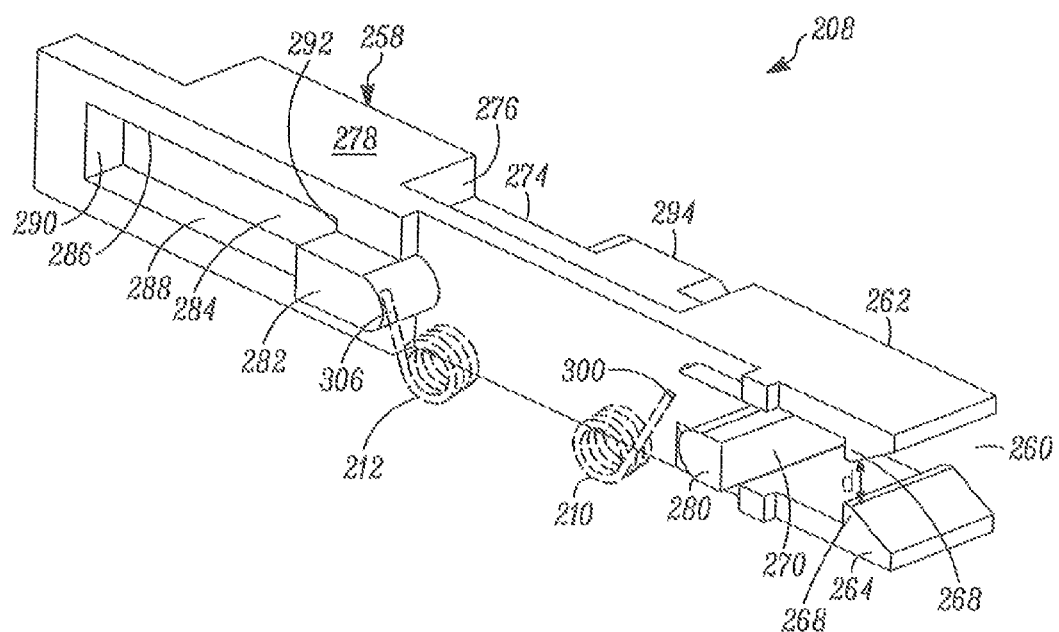
FIG. 23 is a right-front perspective view of the lancet carrier of FIG. 17.

Referring to FIGS. 22 and 23, lancet carrier 208 is described in more detail. Lancet carrier 208 has the primary function of holding lancet 104 as lancet 104 is inserted, fired and ejected from lancing device 102. Lancet carrier 208 includes a main body 258 defining at is front end a mouth 260 comprised of an upper jaw 262 and a lower jaw 264. Upper and lower receiving jaws 262 and 264 are formed of flexible elongated planar members extending forward from main body 258 of lancet carrier 208. The tips of each of upper and lower jaws 262 and 264 include one of two opposing inwardly projecting snaps 268. Unless a force is applied to urge jaws 262 and 264 apart, jaws 262 and 264 will tend to remain in the closed position shown in FIGS. 22 and 23. When jaws 262 and 264 are in the closed position, distance d between snaps 268 is less than the diameter of the mounting bulb 140 of the lancet body 122. It will be appreciated that lancet carrier 208 operates as part of a lancet holding assembly that engages the lancet needle at a position that is independent of the position of receiver 170.

Referring to FIGS. 18 and 19, as lancet 104 is inserted into lancing device 102, lancet body 122 extends through receiver 170 until its conical rear end 136 abuts mouth 260. The distal tip of conical rear end 136 is sufficiently narrow to slide easily between the snaps 268 of upper and lower jaws 262, 264. However, as the conical rear end 136 is plunged further into mouth 260, portions of conical rear end 136 having a wider diameter enter mouth 260 and force apart upper and lower jaws 262, 264 until the mounting bulb 140 of body passes through jaws 262, 264. Once mounting bulb 140 passes, jaws snap shut around neck 138, whose narrower diameter creates a recess that engages snaps 268. Lancet carrier 208 will thus hold lancet body 122 until a sufficient forward force is applied to expel lancet body from mouth 260.

A push plate 270 extends from main body 258 near in the rear of mouth 260 so that push plate 270 abuts the tip of conical rear end 136 of lancet body 122 when lancet body 122 is fully inserted into mouth 260.

Referring to FIG. 22, the top surface 272 of lancet carrier 208 has an intermediately positioned recess 274 that defines a backwall 276. To the rear of recess 274, top surface 272 provides a platform 278. Recess 274 and platform 278 provide surfaces by which trigger 114 engages lancet carrier 208, as described below.

Referring to FIG. 23, a carrier drive spring engagement boss 280 and carrier return spring engagement boss 282 extend from the left side of lancet carrier 208. Carrier drive spring engagement boss can extend out from push plate 270. As explained below in reference to FIGS. 30a through 30d, bosses 280 and 282 engage drive spring 210 and return spring 212, respectively, during the firing of lancing device 102. Drive spring engagement boss 280 has a rounded contour on its rearward-facing side. Return spring engagement boss 282 has a rounded contour on its forward facing side.

An elongated horizontal slot 284 is provided in rearward half portion of lancet carrier 208, below platform 278. Slot 284 defines horizontal sidewalls 286 and 288, a back wall 290 and a front wall 292. As will be explained below with reference to FIGS. 30a through 30d, slot 284 receives engagement members of cocking handle 112 and depth adjustment ring 117.

Carrier drive and return spring engagement bosses 280 and 282 are disposed within lancet carrier right-hand guide track 236 in housing 106 (see FIG. 21) to permit lancet carrier 208 to slide axially within housing 106 along guide track 236. A guide boss 294 extends laterally from the left hand side of lancet carrier 208 just below recess 274 (FIG. 20). Guide boss 294 engages lancet carrier left hand guide track 216 in housing 106 (See FIG. 20) to permit lancet carrier 208 to slide axially within housing 106 along guide track 216. The axial sliding movement of lancet carrier 208 within housing 106 permits lancet carrier (and thus lancet) to be moved under the operation of drive spring 210 to effectuate the cocking, firing and skin-piercing operations of lancing device 102, as described below.

Cocking and Firing

Referring to FIGS. 19 and 21, a drive member has a drive spring 210 torsion spring mounted about drive spring boss 244 of housing 106. A first terminus of drive spring 210 forms a tine 300 that engages the rounded contour of drive spring engagement boss 280. The opposing terminus of drive spring 210 forms a tine 302 that is received by drive spring retention notches 304 on return spring boss 246 of housing 106 (FIG. 19). When drive spring 210 is cocked (as described below), it urges the lancet carrier 208 toward piercing aperture 110 to extend sharp tip 120 into the user's skin.

Referring to FIGS. 19 and 23, return spring 212 is a torsion spring mounted about return spring boss 246 extending from housing 106. A first terminus of return spring 212 is a tine 306 that engages the rounded contour of a return spring engagement boss 282 on the lancet carrier 208. The opposing terminus of return spring 212 is an anchor tine 308 that is engaged return spring stop 252 extending from housing 106. When return spring 212 is tensioned (as described below), it urges lancet carrier 208 away from piercing aperture 110 to retract the sharp tip 120 from the user's skin.

Figure 24:
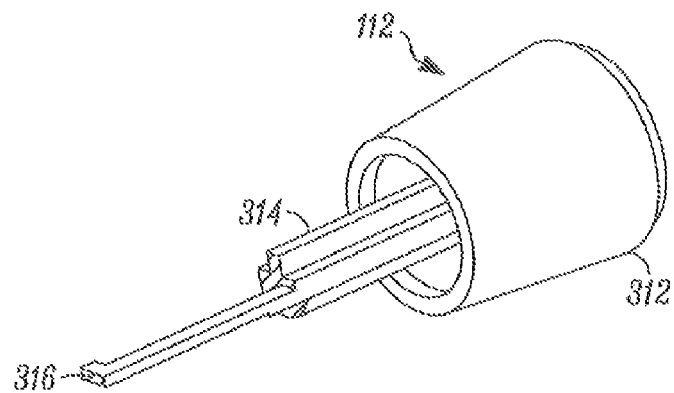
FIG. 24 is a perspective view of the cocking handle of FIG. 17.
Figure 30A:
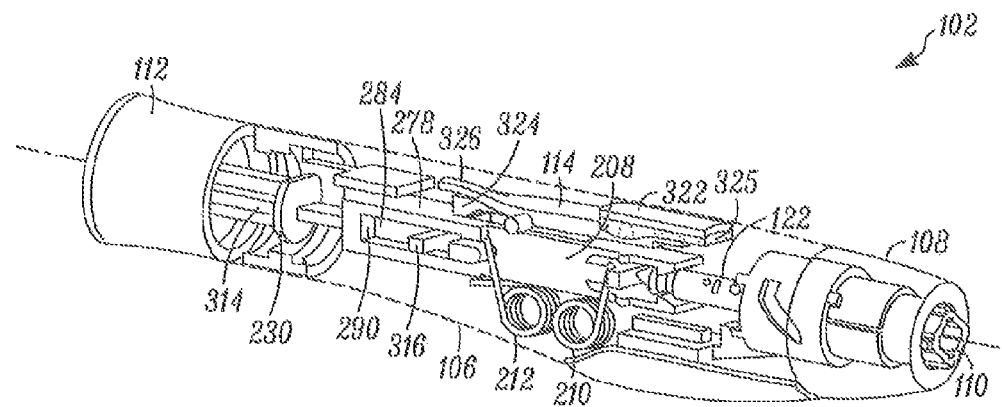
FIGS. 30a through 30d are a series of cut-away right-hand perspective views of the lancing device of FIG. 1, illustrating its cocking and firing operation.

Referring to FIG. 24, cocking handle 112 has a generally cylindrical handle portion 312 sized to fit over rear aperture 201 of housing 106, and an elongated rod 314 extending from handle portion 312. The forward tip of rod 314 terminates in an L-shaped engagement hook 316, which is positioned in slot 284 of lancet carrier 208 as shown in FIG. 30a. As best seen in FIGS. 30a-d, cocking handle 112 is located over rear end of housing 106, with elongated rod 314 passing into the interior of housing 106 through rear aperture 201. The constricted diameter of rear aperture 201 restrains elongated rod 314 to axial movement within housing 106.

A compression spring (not shown) may be placed at rear aperture 201 of housing 106, with one end of the spring secured to housing 106 and the other end secured to handle portion 312 to bias handle portion 312 toward housing.

Figure 27:
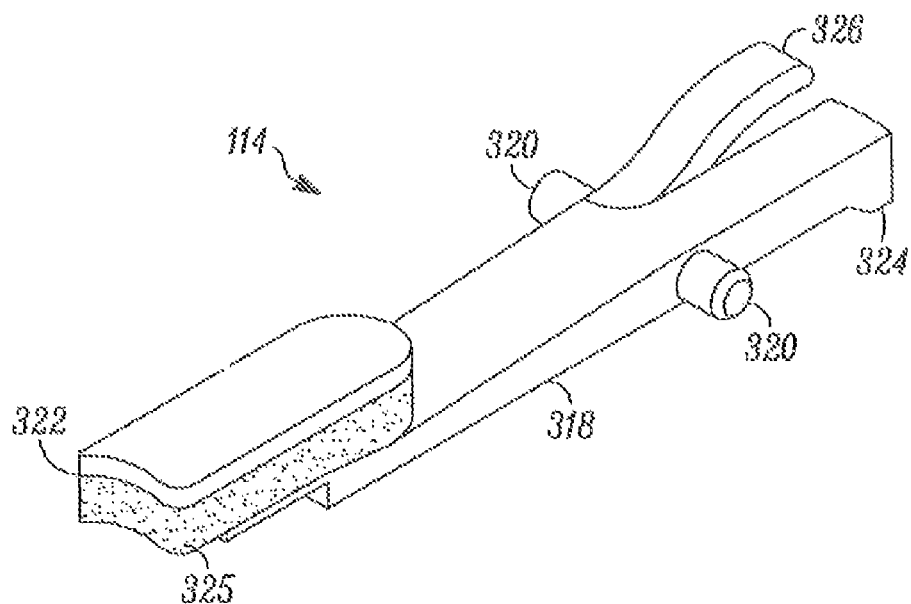
FIG. 27 is a perspective view of the trigger of FIG. 17.
Figure 28:
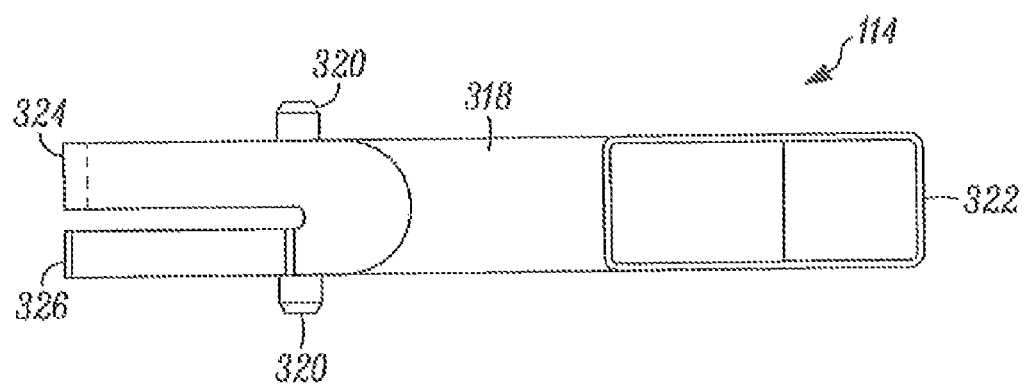
FIG. 28 is a top plan view of the trigger of FIG. 27.
Figure 29A:
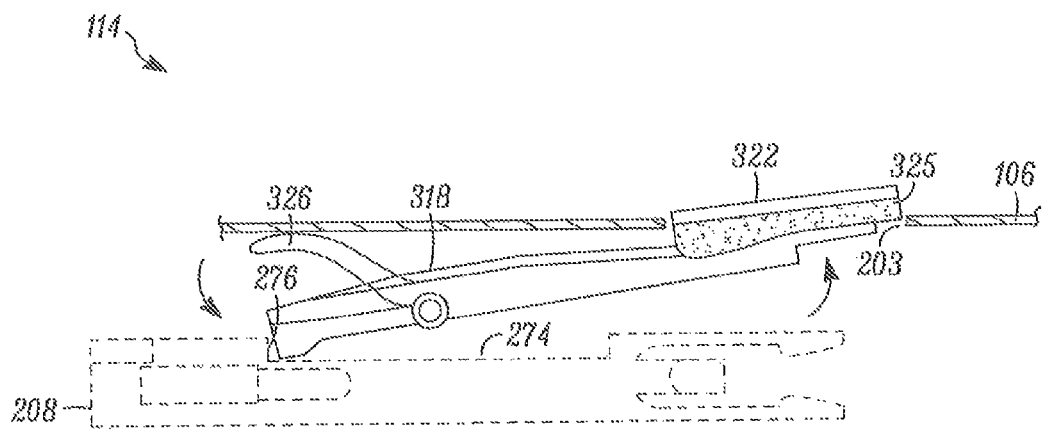
FIG. 29a is a right side view of the trigger of FIG. 26 and its relationship with the lancet carrier of FIG. 22 (shown in phantom lines) showing the position of the trigger relative to the housing of the lancing device when the lancing device is cocked.
Figure 29B:
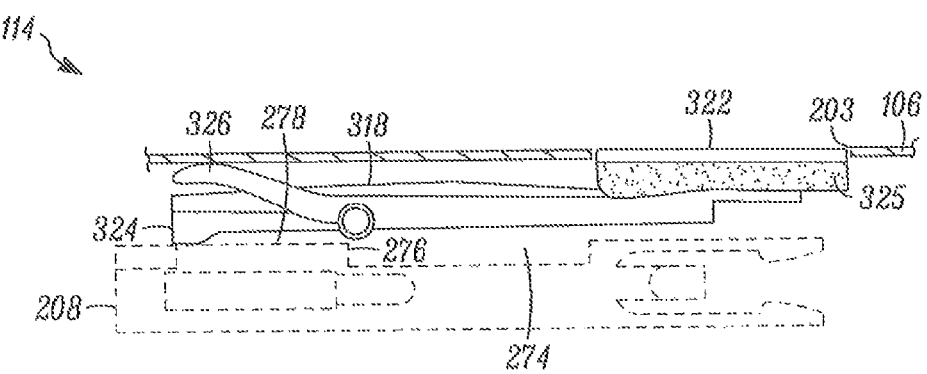
FIG. 29b is a right side view of the trigger of FIG. 26 and its relationship with the lancet carrier of FIG. 22 (shown in phantom lines) showing the position of the trigger relative to the housing of the lancing device when the lancing device is uncocked.

As shown in FIGS. 27 through 29, trigger 114 has an elongated body 318 with opposing laterally extending pivots 320. A user-actuated trigger button 322 is located at the front end of elongated body 318. A tooth 324 depends from the rear end of elongated body 318 and engages the top of lancet carrier 208 as shown in FIG. 29b.

Trigger 114 is mounted to the housing 106 with the trigger button 322 extending through trigger aperture 203 in housing 106 (see FIG. 29a) and each of pivots 320 mounting to one of wells 253 formed in the interior of housing 106.

Trigger button 322 includes a colored band 325 circumscribing the bottom portion of trigger button 322 and can have a color that contrasts with the color of the remainder of trigger button 322. For example, trigger button 322 can be black with a colored band 325 that is red. Colored band 325 is visible to a user when the trigger button 322 extends fully through trigger aperture 203. Colored band 325 is at least partially obscured from the user's view by the housing 106 when trigger button 322 does not fully extend through the trigger aperture 203, as shown in FIG. 29. If desired, other indicia may be used instead of a colored band, including for example graphics or alphanumeric symbols, which are placed along the bottom portion of trigger button 322.

A biasing leaf element 326 extends from the rear end of trigger 114 and urges downward the rear end of elongated body 318 so as to urge tooth 324 toward lancet carrier 208 and, in see-saw fashion, urges trigger button 322 upward. By pressing trigger button 322 down, the user can overcome the force of biasing leaf element 326 and swing tooth 324 upward away from lancet carrier 208 to fire lancing device 104 when cocked.

Referring to FIGS. 29a and 29b, the position of trigger 114 relative to housing 106 is illustrated when lancing device 102 is in its cocked and uncocked positions, respectively. As shown in FIG. 29a, when lancing device is cocked, trigger button 322 extends through trigger aperture 203 in housing 106 so that colored band 325 is visible to user, to provide both tactile and visual feedback to the user that lancing device 102 is cocked. As shown in FIG. 29b, when lancing device 102 is uncocked, trigger button 322 is withdrawn so that it does not extend through trigger aperture 203 and the top surface of trigger button 203 is even with the surface of housing 106. In this position, colored band 325 is not visible. When trigger button 322 is withdrawn and colored band 325 is not visible, the user has both tactile and visual feedback that lancing device 102 is not cocked.

Figure 30B:
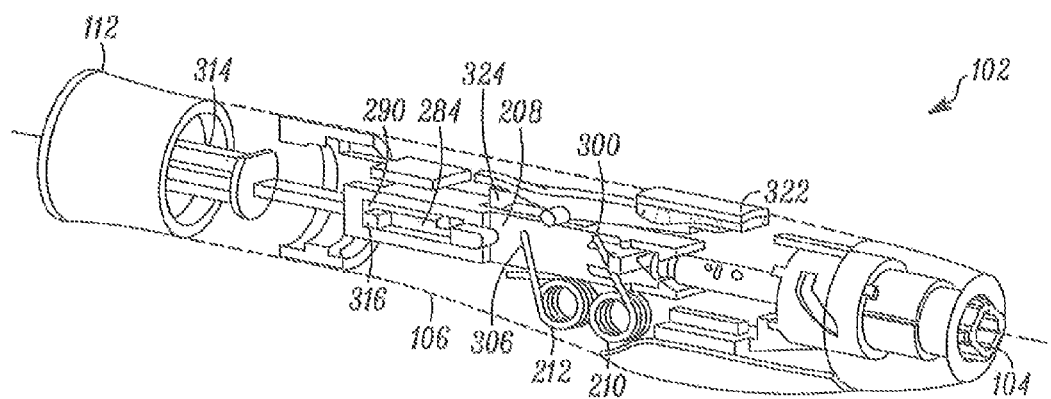
Figure 30C:
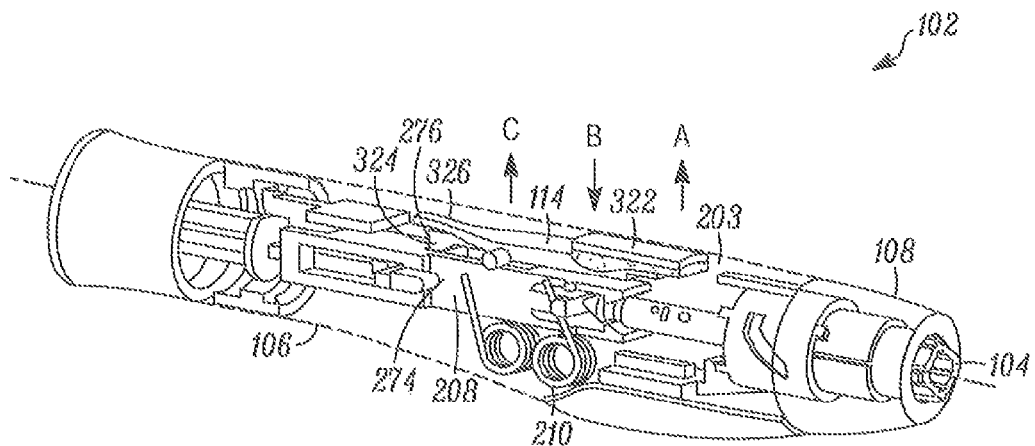
Figure 30D:
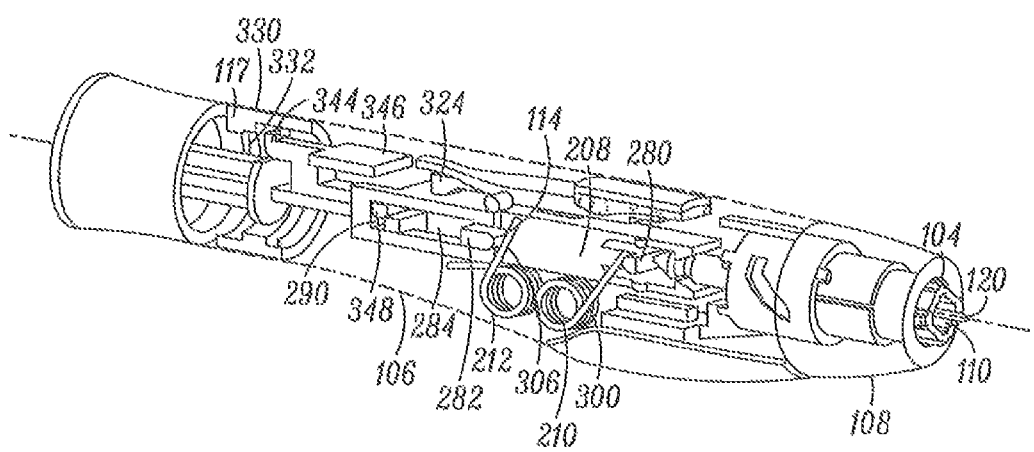

Referring to FIGS. 30a through 30d, the cocking and firing process of lancing device 102 is described in more detail. Lancet carrier 208 can have three principal positions relative to drive spring 210 and return spring 212: the neutral position (FIG. 30a), cocked position (FIG. 30c), and the extended firing position (FIG. 30d).

Referring to FIG. 30a, in its neutral position, lancet carrier 208 is positioned so that both drive and return springs 210 and 212 are in a relaxed state. The neutral position is the position that lancing device 102 returns to after it has been fired.

In the neutral position, tooth 324 of trigger 114 rests on platform 278 of lancet carrier 208 (as also shown in FIG. 29b). This forces trigger button 322, in see-saw fashion, to withdraw from the trigger aperture 203 in the housing 106 so that trigger button 322 either flush with exterior of housing 106 or can extend only partially outside housing 106. In either case, colored band 325 on trigger button 322 is not visible to the user, as also shown in FIG. 29b.

In the neutral position, cocking handle 112 is at rest on the rear end of housing 106, cocking rod 314 is fully extended into housing 106 and cocking hook 316 is disposed in slot 284 some distance removed from backwall 290.

Referring to FIG. 30b, the user cocks lancing device by pulling cocking handle 112 away from housing. As cocking handle 112 is pulled, cocking rod 314 is drawn in a rearward direction through rear aperture 201 and cocking hook 316 slides rearward through slot 284 until cocking hook abuts backwall 290. With cocking hook 316 abutting backwall 290, continued pulling of cocking handle 112 pulls lancet carrier 208 rearward relative to its neutral position so that drive spring engagement boss 280 pushes tine 300 of drive spring 210 into a tensioned or cocked position.

Referring to FIG. 30c, when lancet carrier 208 is in a fully cocked state, the lancet carrier 208 is moved rearward so that its recess 274 is positioned under tooth 324 of trigger 114. Under the urging of bias leaf 326, tooth 324 extends into recess 274 and engages back wall 276, holding lancet carrier 208 in its fully cocked position. A more detailed view of the engagement of tooth 324 into recess 274 is shown in FIG. 29a.

As bias leaf 326 pushes tooth 324 into lancet carrier recess 274, it urges trigger button 322 upward in the direction of Arrow A to fully extend through trigger aperture 203. In this position, colored band 325 about the base of the trigger button 322 is visible to the end user to indicate that the lancing device 102 is cocked, as also shown in FIG. 29a.

When the user depresses the trigger button 322 (in the direction of arrow B), the force of biasing leaf 326 is overcome, and tooth 324 swings upward (in the direction of arrow C) out of recess 274 in lancet carrier 208. Once tooth 324 is removed from recess 274, cocked lancet carrier 208 is no longer restrained and it accelerates forward under the force of drive spring 210 toward its extended piercing position as shown in FIG. 30c.

Referring to FIG. 30d, lancet carrier 208 is shown in its extended piercing position after having been fired (that is, released from its cocked position) by the user's actuation of trigger 114. In this extended piercing position, drive spring 210 (by action of tine upon drive spring engagement boss 280 (not shown)), has propelled lancet carrier 208 toward piercing aperture 110 in cap 108. As a result, sharp tip 120 protrudes momentarily from the piercing aperture 110 in the cap 108 to pierce the user's skin.

In the extended piercing position, lancet carrier 208 is positioned forward of the neutral position, so that return spring engagement boss 282 pushes tine 306 of return spring 212 into a tensioned position. In this tensioned position, return spring tine 306 urges the lancet carrier 208 rearward, away from the user's skin back toward the neutral position shown in FIG. 30a, thus withdrawing sharp tip 120 from the skin.

Note that during the cocking and firing operations described above, lancet sleeve 130 can remain stationary.

As explained above, lancet carrier 208 can also be cocked by insertion of lancet 104 while lancing device 102 is in AST mode. When lancet 104 is inserted, conical rear end 136 of lancet body 122 pushes lancet carrier 208 rearward to its cocked position, where tooth 324, of trigger 114, extends into recess 274 of lancet carrier 208 to hold lancet carrier in its cocked position.

It will be appreciated that springs 210 and 212 and trigger 114 comprise a user-actuated drive mechanism. Any other suitable drive mechanisms can be employed, including for example, coil springs, electromagnetic drives, or impact hammer arrangements. It will be further appreciated that the trigger mechanism employed may be any other suitable triggering means, including for example pulley movement actuated by rotating or pulling the lancet device or a sliding mechanism.

Depth Adjustment

Figure 25:
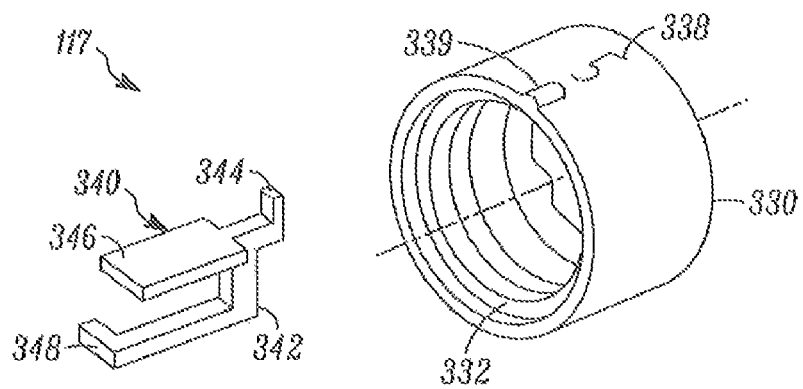
FIG. 25 is a front perspective view of the depth adjustment ring and depth actuator of FIG. 17.
Figure 26:
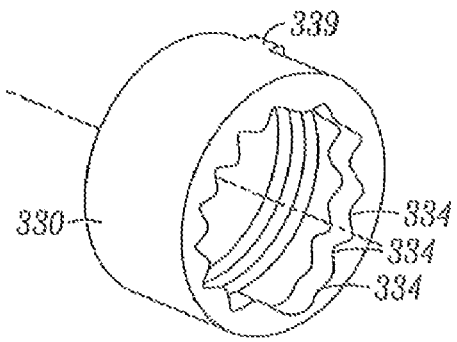
FIG. 26 is rear perspective view of the depth adjustment ring of FIG. 17.

Referring to FIGS. 25 and 26, the function of depth adjuster 117 is to limit the forward axial movement of sharp tip 120 relative to the skin-engaging surface 254 of cap 108, and thereby limit the depth that sharp tip 120 penetrates the user's skin.

Depth adjuster 117 includes a depth adjustment ring 330 mounted for rotation about the distal mounting portion 228 of housing 106 as shown in FIGS. 1-4. The forward interior portion of depth adjustment ring 330 has threads 332, and the rearward interior portion depth adjustment ring 330 has circumferentially arranged detents 334. A protrusion (not shown) on portion 228 of housing 106 engages detents 334 to provide discrete settings for depth adjustment ring 330 as it rotates about distal mounting portion 228.

The exterior of depth adjustment ring 330 is accessible to users for rotation and includes indicia 338 and a knob 339 to facilitate manipulation by the user. As depth adjustment ring 330 rotates, indicia 338 are visible to the user to indicate the resulting depth setting.

Depth adjuster 117 also includes a depth adjuster actuator 340, which has an generally Z-shaped chassis 342. A finger 344 projects from the rear end of Z-shaped chassis 342 and is sized to fit in threads 332. A guide surface 346 extends from an intermediate portion of Z-shaped chassis 342. A depth stop 348 projects from the forward end of Z-shaped chassis.

As best seen in FIG. 30d, depth adjuster actuator 340 is installed within housing 106 so that finger 344 is disposed with threads 332, guide surface 346 is adjacent to and parallel with guide surface 350, 352 of housing, and depth stop 348 is disposed within slot 284 of lancet carrier 208.

As depth adjustment ring 330 rotates, finger 344 follows threads 332 causing depth adjustment actuator 340 to move axially forward and rearward (depending on the direction that depth adjustment ring 330 is rotated). This motion in turn causes depth stop 348 to slide forward and rearward relative to slot 284 (depending on the direction that depth adjustment ring 330 is rotated). The motion of depth adjuster actuator 340 is limited by the length of slot 284 or alternatively by the length of threads 332. There is now a pair of stops that limit the rotation of the ring 330.

Guide surfaces 346 and depth stop 348 slide along adjacent planar parallel guide surfaces 350 and 352, respectively, extending from housing 106 (see FIG. 20) interact to limit motion of depth actuator 340 to axial (as opposed to lateral) movement.

When the user depresses trigger 114 when lancing device is in its cocked state, drive spring 210 propels lancet carrier 208 forward to extend sharp tip 120 through piercing aperture 110 and into the user's skin. During forward motion of lancet carrier 208, depth stop 348 remains stationary so that eventually the back wall 290 of slot 284 will impact depth stop 348, as shown in FIG. 30d. This impact prevents further forward movement of lancet carrier 208 relative to housing 106 and thus limits the penetration of sharp tip 120. By rotating depth adjustment ring 330, the user can selectively position depth stop 348 relative to lancet carrier 208 (as indicated by indicia 338) and thus control penetration depth of sharp tip 120.

AST Mode Adjustment

Lancing device 102 operates in AST mode and finger mode. In AST mode, lancing device 102 is configured for use with fleshy parts of the body such as a thigh or forearm. In finger mode, lancing device 102 is configured for use with a fingertip.

Figure 33:
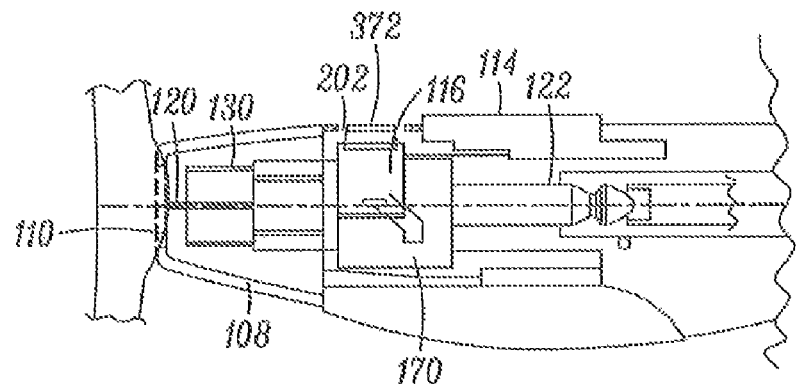
FIG. 33 is a left side view (with housing cut away to reveal internal mechanisms) of the lancing device in AST mode with the cap placed on a user's skin in preparation for lancing operations.

Referring to FIGS. 31 and 33, operation of lancing device 102 in an AST mode is shown. In AST mode, cap 108 is placed against a fleshy part of the body. Compression ring 256 engages the user's skin, causing it to pucker inside the relatively wide piercing aperture 110. The puckered flesh is then pierced by sharp tip 120, as shown in FIG. 33, allowing the user to apply pressure before, during and after lancing to help with blood acquisition. Clearance prevents wicking of the blood drop and allows the user to see when sufficient blood has been acquired.

Figure 32:
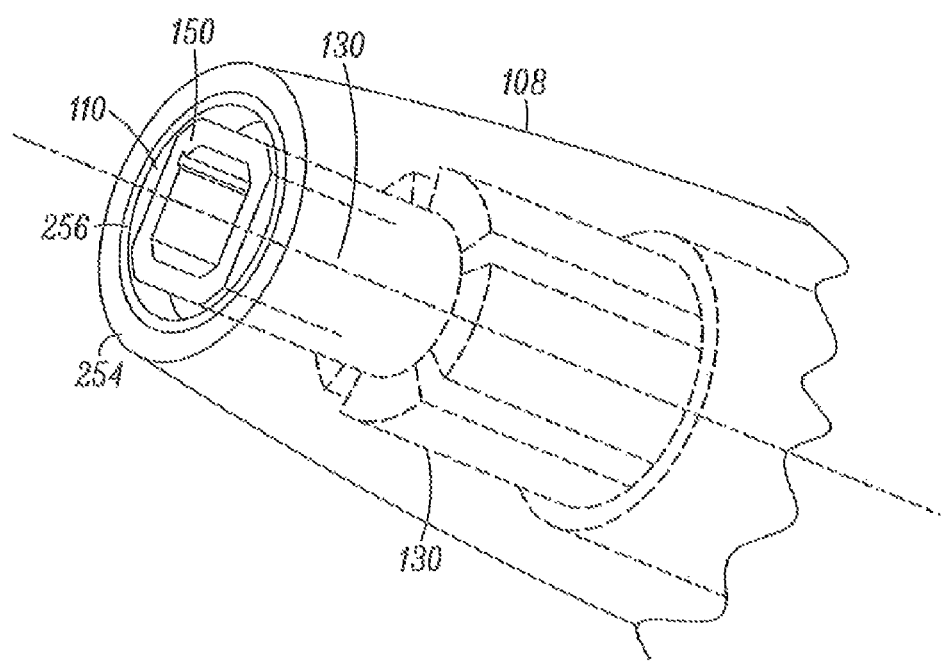
FIG. 32 is an isolated perspective view of the cap of the lancing device of FIG. 1, showing the position of the lancet sleeve when lancing device is in AST mode.
Figure 34:
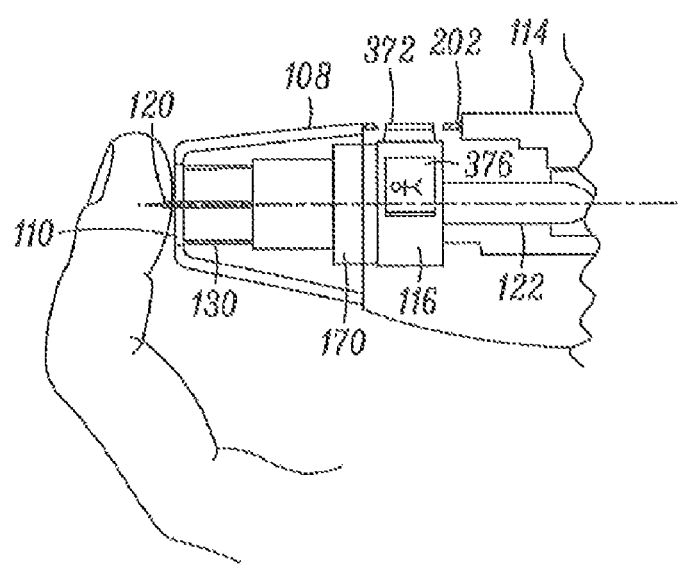
FIG. 34 is s a left side (with housing cut away to reveal internal mechanisms) of the lancing device in finger mode with the cap placed on a user's finger in preparation for lancing operations.

Referring to FIGS. 32 and 34, operation of lancing device 102 in a finger mode is shown. In finger mode, sleeve 130 is slid toward the front end of the cap 108 (by means of AST mode actuator ring 116 and receiver 170, as described below), so that the front end 150 of sleeve 130 is interposed in or obstructs a portion of piecing aperture 110, providing in conjunction with compression ring 256, a skin-engaging contour that is suitable for placement against a finger. The obstruction of the piercing aperture 110 that is effected by sleeve 130 need not be complete; rather sleeve 130 can be placed in proximity to piercing aperture 110 so that the user's skin will encounter sleeve 130 when cap 108 is placed against the user's body prior to firing lancing device 102, and consequently, the user's skin will not be able to pucker into cap 108 through piercing aperture 110, at least to the same extent as the skin could pucker if sleeve 130 were not obstructing piercing aperture 110. When sleeve 130 obstructs piercing aperture 110, front end 150 of sleeve 130 can be substantially coplanar with compression ring 256.

Referring to FIGS. 33 and 34, sleeve 130 is held by receiver 170, which in turn is controlled in cam-like fashion by AST mode actuator ring 116. To transition between AST and finger mode, the user rotates AST mode actuator ring 116, which drives the receiver 170 (and hence the lancet sleeve 130) axially toward or away from the skin-engaging surface 254 of the cap 108 (depending on which direction the user rotates AST mode actuator ring 116). It will be seen that AST mode actuator ring 116 operates as a user-actuated assembly or user-controlled actuator to transition the lancing device between finger mode and AST mode by moving sleeve 130 into a first or forward position where it obstructs piercing aperture 110 and a second or rearward position where sleeve 130 is withdrawn from piercing aperture 110 so that sleeve 130 no longer impinges on the user's skin when cap 108 is placed into contact with the user prior to firing lancing device 102. Alternatively, sleeve 130 can protrude forward past the skin contacting surface of cap 108. When the sleeve 130 is in its second or rearward position, for AST mode, it is sufficiently spaced apart from the piercing aperture 110 so that it does not flatten the user's puckered skin during incision, as shown in FIG. 33.

In other words, when the lancet sleeve 130 is interposed within the piercing aperture 110, it adjusts the effective size of the piercing aperture 110 to a second diameter of the front end of the sleeve 150. When the lancet sleeve 130 is withdrawn from the piercing aperture 110, it adjusts the effective size of the piercing aperture to a larger first diameter, in this embodiment, the diameter of unobstructed piercing aperture 110. This larger first diameter is sufficiently large to allow the user's skin to pucker into the piercing aperture 110, as shown in FIG. 33. Other mechanisms for changing the effective size of the piercing aperture 110 and can be used as well. For example, the sleeve 130 can be mounted to the housing 106, as opposed to the lancet 104, or the skin engaging cap 108 can be deformed.

Figure 35:
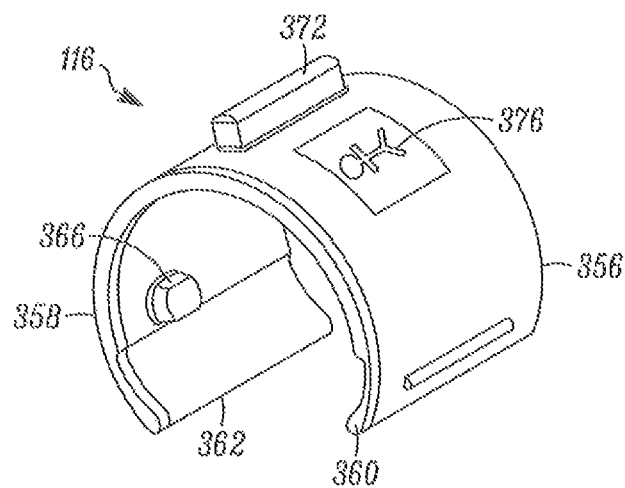
FIG. 35 is front perspective view of the AST mode actuator ring of FIG. 17.
Figure 36:
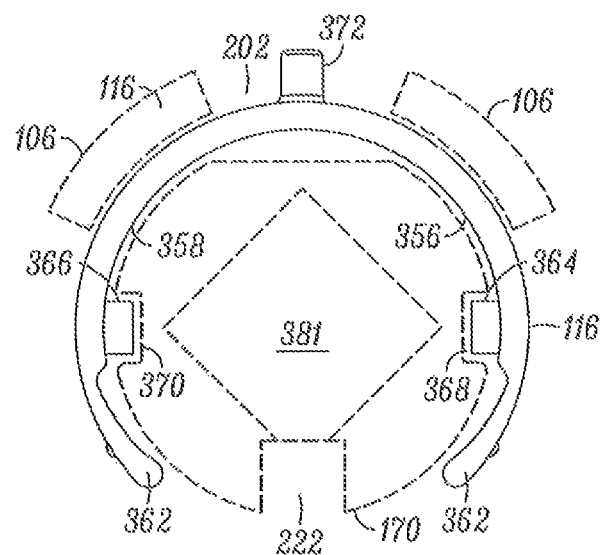
FIG. 36 is a front view of the AST mode actuator ring of FIG. 35 and its relationship with the receiver of FIG. 17 (shown in phantom lines)
Figure 37:
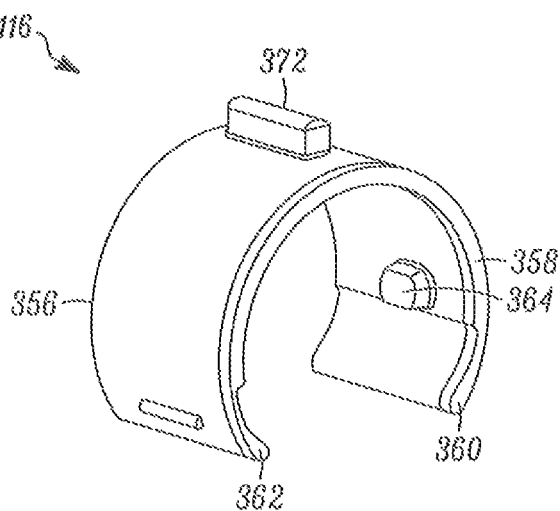
FIG. 37 is a rear perspective view of the AST mode actuator of FIG. 35.

AST mode actuator ring 116 is shown in more detail in FIGS. 35-37. AST mode actuator ring 116 is a semi-circular body rotatably mounted in housing 106 between shoulders 220 (FIG. 20). AST mode actuator ring 116 includes left and right semi-circular portions 356 and 358 each terminating in clasping ends 360 and 362, respectively. The diameter of AST mode actuator ring 116 is sized to permit it to be secured about receiver 170 as shown in FIG. 36 (with sectional view of receiver 170) when left and right semi-circular portions 356 and 358 are flexed slightly outward by the girth of receiver 170 to urge clasping ends 360 and 362 into tight engagement of receiver 170.

Figure 44:
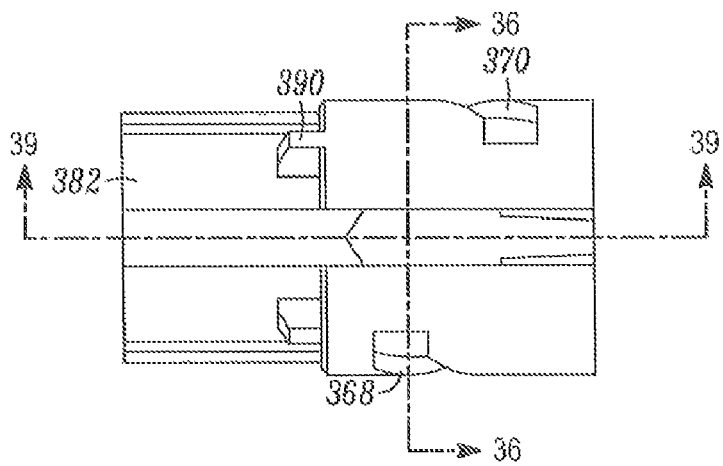
FIG. 44 is a top plan view of the receiver of FIG. 38.

AST mode actuator ring 116 includes two opposing bosses 364 and 366, each of left and right semi-circular portions 356 and 358, respectively. Each boss 364 and 366 is sized to engage corresponding cam trails 368 and 370 on receiver 170 (see FIGS. 38 and 44), so that rotation of AST mode actuator ring 116 will selectively position receiver 170 (and thus lancet sleeve) axially forward and axially rearward, depending on which direction AST mode actuator ring 116 is rotated. Receiver 170 is disposed within housing 106 to allow axial (but not rotational) maneuvers.

As best seen in FIGS. 3, 18 and 36, a user-actuated member in the form of control member 372 extends from the AST mode actuator ring 116 through AST mode actuator aperture 202 in the housing 106 to provide a user interface for manipulation of AST mode actuator ring 116 by the user. The user has adjusted the effective size of the piercing aperture 110 to the chosen diameter when a portion of the AST mode actuator ring 116 is positioned in visual association with the indicia. Because control member 372 is captured in AST mode actuator aperture 202, the size of AST mode actuator aperture 202 defines the range that the user can rotate AST mode actuator ring 116. Other user interfaces can be employed, including textured gripping surfaces. AST mode actuator aperture 202 is forms a slot having lateral ends that define a path of travel there between for control member 372. The shape of aperture 202 may be varied to ovoid, rectilinear or other suitable shapes.

Indicia 376 on the outer circumferential surface of the AST mode actuator ring 116 is visible to the user through AST mode actuator aperture 202 when AST mode actuator ring 116 has been rotated to the switch lancing device 102 into AST mode. In this case, indicia 376 is a diagram of a human body, conveying to the user the fact that in AST mode lancing device 102 can be used to draw bodily fluid from tissue other than a finger, other symbols or icons may be used. Alternatively, indicia 376 can be located on AST mode actuator ring 116 so that indicia 376 is visible through AST mode actuator aperture 202 when AST mode actuator ring 116 has been rotated to switch lancing device 102 into finger mode. Alternatively, two indicia can be used, one to indicate AST mode and the other to indicate finger mode. Alternatively, the two indicia may be located on the housing.

Figure 38:
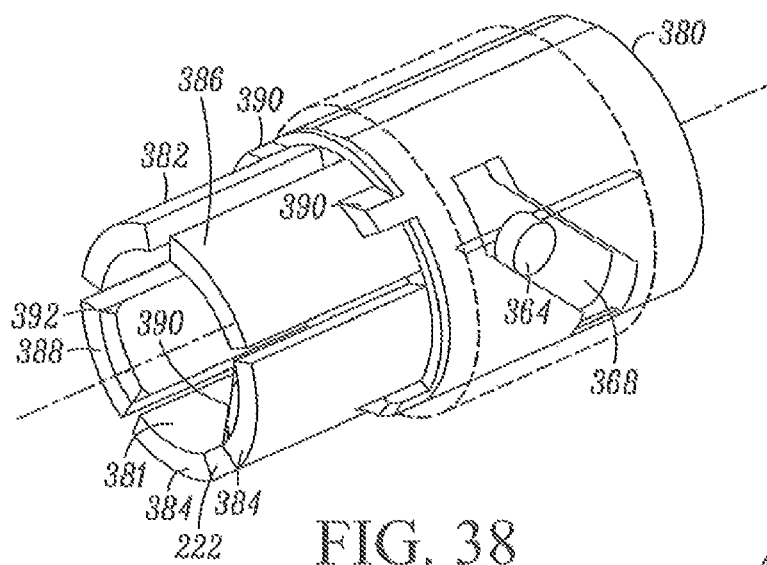
FIG. 38 is a front perspective view of the receiver of FIG. 17 and its relationship with the AST mode actuator ring.
Figure 39:
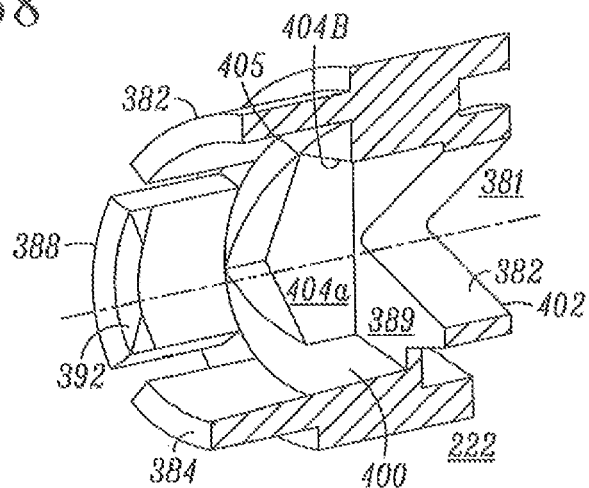
FIG. 39 is a front perspective sectional view of the receiver of FIG. 38, taken along the lines 39-39 in FIG. 33.
Figure 40:
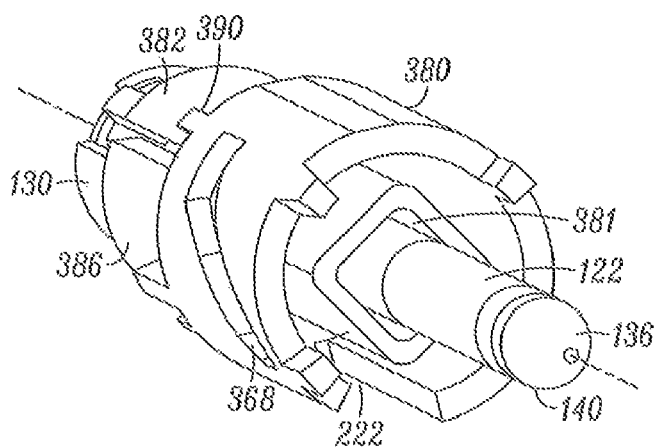
FIG. 40 is a rear perspective view of the receiver of FIG. 38 with a lancet inserted therein.

Referring to FIGS. 38 through 44, receiver 170 is described. As explained below, receiver 170 acts as a sleeve-engagement portion to releasably engage lancet sleeve 130. Receiver 170 is coupled to AST mode actuator ring 116 and configured to move sleeve 130 in response to the movement of AST mode actuator ring 116. Receiver 170 is generally tubular in construction with a cylindrical receiver body 380 defining an elongated inner chamber 381 therein that is sized and configured to receive lancet 104 as shown in FIG. 40. Elongated slot 222 runs the longitudinal extent of the underside of receiver 170.

Referring to FIG. 38, cam trails 368 and 370 are cut into the left and right exterior sides of receiver body 380. Cam trail 368 on the left side of receiver body 380 runs at a 45 degree angle from vertical from a forward-upper portion of the left exterior side of receiver body 380 to a lower-rearward portion of the left exterior side of receiver body 380. The angle determines the ratio of angular rotation to linear translation and can be varied to achieve different amounts of translation.

Cam trail 370 is complementary to cam trail 368, and runs at a forty five degree angle from vertical from a forward-lower portion of the right exterior side of receiver body 380 to a upper-rearward portion of the right exterior side of receiver body 380.

AST mode actuator is clasped about receiver body 380 of receiver 170 so that bosses 364 and 366 are inserted into cam trails 368 and 370, respectively, as shown in FIG. 36. As AST mode actuator ring 116 rotates rightward (that is, clockwise when looking at AST mode actuator ring from the rear of lancing device 102), bosses 364 and 366 drive receiver 170 (and thus lancet sleeve 130) axially rearward to the AST mode position (FIG. 33). As AST mode actuator ring 116 rotates leftward (that is, counter-clockwise when looking at AST mode actuator ring from the rear of lancing device 102), bosses 364 and 366 drive receiver 170 (and thus lancet sleeve 130) axially rearward to the finger mode position (see FIG. 34). Lancet body 122 is engaged by lancet carrier 208, so that lancet body 122 does not move as receiver 170 axially slides lancet sleeve 130.

Extending from the forward end of receiver body 380 are a pair of upper and lower guide fins 382 and 384 and a pair of lateral fins 386 and 388. Lower guide fine 384 is longitudinally bifurcated by slot 222. Fins 382-388 are curved about their respective longitudinal axii to define a portion of the circumference of a circle about the major axis of receiver body 380, as most readily seen in the front view of FIG. 42.

When lancet 104 is fully inserted into receiver 170, sleeve 130 is disposed in the closure defined by upper and lower guide fins 382, 384 and lateral fins 386, 388, with the rear end 152 of sleeve 130 abutting a backstop 389 (FIG. 39) formed in the elongated interior chamber 381 of receiver 170 and in the sectional view of FIG. 18. In this configuration, lancet body 122 extends entirely through the elongated interior chamber 381 so that conical rear end 136 of lancet body 122 extends from the rear end of receiver 170 and is engaged by lancet carrier 208.

Reinforcements 390, at the rear end of upper and lower guide fins 382 and 384, provide rigidity to guide fins 382 and 384 and to align the receiver within the housing. Lateral fins 386 and 388 do not have reinforcements and are sufficiently thin so as to have flexibility in response to lateral forces.

The front tips of lateral fins 386 and 388 include opposing inwardly projecting snaps 392. When lateral fins 386 and 388 are in a relaxed state (that is, not flexed outward), the distance between snaps 392 is slightly less than the diameter of annular flange 164 of sleeve 130. As lancet 104 is inserted into receiver 170, annular flange 164 abuts snaps 392. Continued insertion of annular flange 164 against snaps 392 will flex lateral fins 386 and 388 slightly apart, permitting passage of annular flange 164 into elongated interior chamber 381. Once annular flange 164 is clear of snaps 392, lateral fins 386 and 388 (having been pushed apart) urge snaps 392 into clasping engagement with mounting shoulder 166 on the front side of annular flange 164, as best seen in FIG. 18. Other suitable means can be used to couple receiver 170 and lancet sleeve 130.

Elongated interior chamber 381 is configured for mating engagement with the external contours of lancet sleeve 130 and lancet body 122. As shown in the cut-away perspective view of FIG. 39, receiver body 380 includes a forward internal portion 400 and a rearward internal portion 402.

Forward internal portion 400 of receiver body 380 has a diameter sufficiently wide to accommodate the rear portion 158 of sleeve 130. Forward internal portion 400 forms lateral guide wall 404a which has a vertical planar face and upper guide wall 404b which has a horizontal planar face forming a 90° intersection 405 with guide wall 404a in the upper right-hand portion of elongated interior chamber 381. FIG. 42 is a front view of receiver 170 showing in phantom lines a sectional view of lancet sleeve 130. When lancet sleeve 130 is inserted into receiver 170, depending on the random orientation of lancet 104 in the user's hand when inserted into lancing device 102), one of either planar surface 172c or 172f (see FIG. 15) will be flush against guide wall 404a, and the adjacent planar surface 172d or 172a (again, depending on the orientation of lancet 104 when inserted into lancing device 102) will be flush against guide wall 404b, so that the intersection of planar surfaces 172c and 172d (or, as the case may be, 172f and 172a) will be aligned in mating engagement with intersection 405, as shown in FIG. 42. A pair of guide walls 404c and 404d can be provided in the lower left-hand portion of elongated chamber 381 to engage the pair of planar surfaces 172 that are opposite the pair of planar surfaces engaged by guide walls 404a and 404b. It will be seen in FIG. 42 that the engagement of one of planar surfaces 172 with walls 404 will rotate the entire lancet forty five degrees from vertical orientation.

Figure 41:
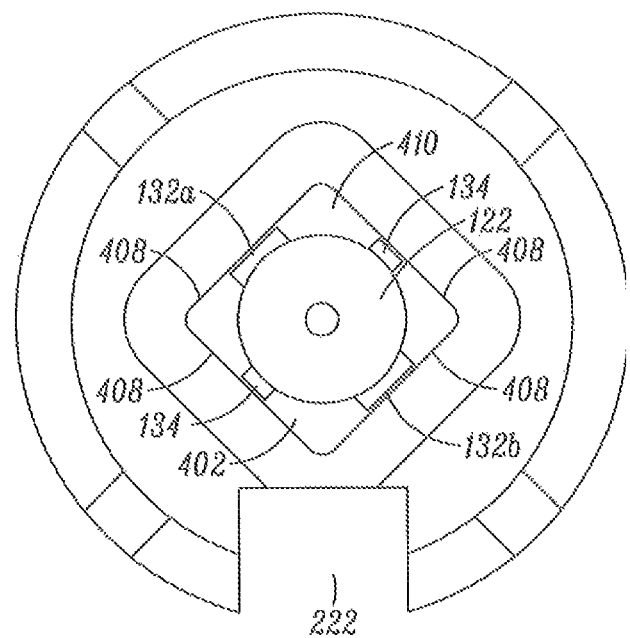
FIG. 41 is a rear view of the receiver and lancet of FIG. 40.

As seen in FIGS. 39 and 41, rearward internal portion 402 of receiver body 380 has a diamond-shaped cross section sized to accommodate lancet body 122 and including rear guidewalls 408. Rearward internal portion 402 is narrower than forward internal portion 400.

When lancet 104 is initially inserted into receiver 170 by the user, sleeve 130 is in its extended protective position and locking member wings 132a, 132b are in the extended configuration to engage sleeve 130 and prevent sleeve 130 from sliding toward the rear end of lancet body 122 (as shown in FIG. 5).

During insertion of the lancet 104 into receiver 170, the rear half of lancet body slides readily through the rearward internal portion 402 of receiver. As wings 132a, 132b enter rearward internal portion 402, they are folded into wing wells 142a, 142b by the constricted width between guide walls 408 into the retracted configuration, as best seen in FIG. 41.

When lancet 104 is fully inserted into lancing device 102, sleeve 130 is secured to receiver 170 by snaps 392 (at sleeve's front end 150) and backstop 389 (at sleeve's rear end 152). Thus, axial movement of receiver 170 will cause sleeve 130 to slide axially relative to piercing aperture 110 from its finger mode position (shown in FIGS. 31 and 33) to its AST mode position (shown in FIGS. 32 and 34) while lancet body 122 (and needle 118 embedded therein) remain in place relative to piercing aperture 110. At the same time, lancet body 122 is engaged in the mouth 260 of lancet carrier 208, so that lancet body 122 does not move axially as receiver slides sleeve 130 forward and rearward, as can be seen by comparing the position of lancet body 122 in FIGS. 33 and 34.

When lancet sleeve 130 is fully inserted into receiver 170, rear end 152 of sleeve 130 will impinge on backstop 389 of receiver 170, so that lancet sleeve 130 (and consequently, lancet body 122), cannot be further inserted. Thus, firm insertion of lancet 104 when lancing device 102 is in AST mode will cause conical rear end 136 of lancet body 122 to drive lancet carrier 208 rearward into its cocked position shown in FIG. 30c. Note that after initial firing, lancing device can be re-cocked by pulling cocking handle as described above in reference to FIG. 30b.

Figure 48:
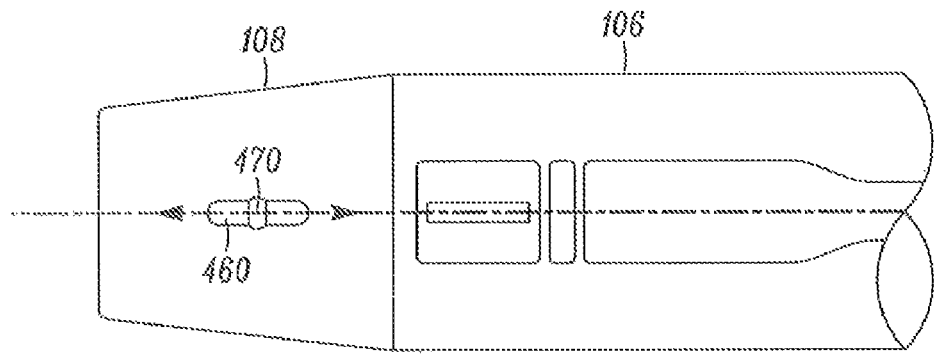
FIG. 48 is a top plan view of a lancing device in accordance with a further embodiment.
Figure 49:
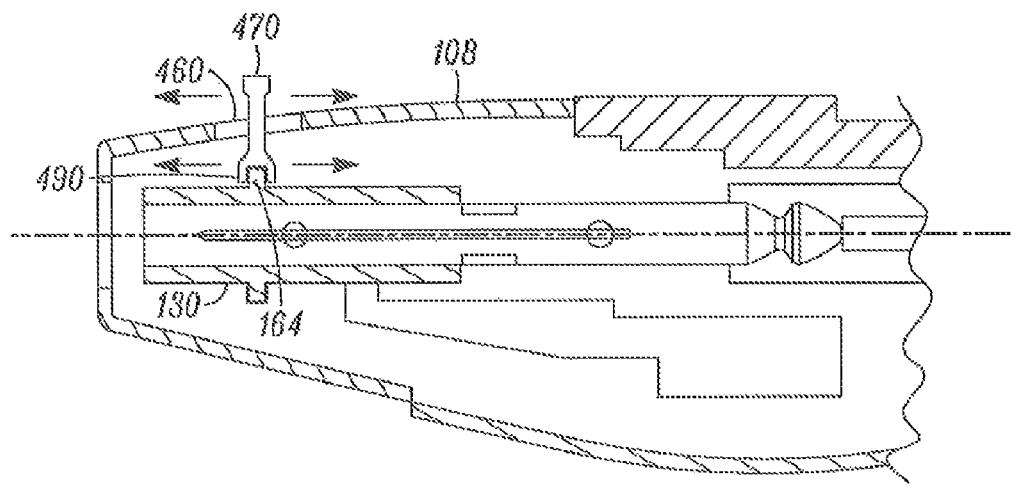
FIG. 49 is a partial sectional view of a lancing device in accordance with a further embodiment, taken along the lines 49-49 in FIG. 48.

It will be seen that AST mode actuator ring 116 and receiver 170 function together as an actuator that releasably engages sleeve 130 to permit the user to selectively move sleeve 130 relative to housing 106 and lancet needle 118. Other mechanisms can be employed within the scope of the present invention to accomplish this function. For example, referring to FIGS. 48 and 49, in lieu of rotatable AST mode actuator ring 116, a linear switch 460 can be provided which includes a finger 470 extending though a slot 480 in cap 108. Slot 480 can be parallel to the longitudinal axis of housing 106, and finger 470 can be coupled to the receiver so that axial movement of finger 470 by the user drives corresponding axial movement of sleeve 130. Also, in lieu of receiver 170, different structures may be employed to releasably clasp sleeve 130. For example, the end of finger 470 can include a pair of tines 490 to clasp sleeve 130 about annular flange 164, thus translating axial movement of finger 470 to corresponding axial movement of sleeve 130. Alternatively, inner chamber 381 of receiver 170 can be sized to hold sleeve 130 in a friction fit.

It should also be noted that while AST mode actuator ring 116 and receiver are directly coupled together, they may also be effectively coupled for purposes of the invention through one or more intermediate parts.

Ejection Slide and Ejection Actuator

Referring to FIGS. 45 and 46a through 46d, the structure and operation of ejection slide 115 and ejection actuator 121 is discussed. Ejection slide 115 is a user actuated feature external to housing 106, whose function (in conjunction with ejection actuator 121) is to eject lancet 104 from lancing device 102 such as after use.

Ejection actuator 121 is slidably mounted within housing 106 and includes an elongated main body 420 having top surface 422. A finger 424 extends from top surface 422 near the front end of main body 420 into the underside of receiver 170 through elongated slot 222, where finger 424 is to the rear of and the same height as the down most portion of ejection shoulder 168, as best shown in FIG. 18. Alternatively, finger 424 can engage another part of sleeve 130, such as its rear end 152. As explained below, finger 424 engages lancet sleeve to eject lancet 104 from lancing device 102. Two tongues 426 extend laterally and in opposing directions from the underside of main body 420. Each of tongues 426 extends through its adjacent one of elongated slots 240 formed in lateral walls of housing 106, permitting ejection actuator 121 to slide along elongated slots 240 in forward and rearward axial directions, but otherwise preventing lateral or vertical movement of ejection actuator 121.

Tongues 426 projects through slots 240 and are received by wells 430 formed on the interior side of ejection slide 115. Tongues 426 can be affixed in wells 430 by means of adhesive, snap engagement or other suitable means. Thus, ejection slide 115 is coupled to ejection actuator 121 so movement of one will cause movement of the other.

During lancing operations, ejection slide 115 and ejection actuator 1121 are in their rearmost at rest positions. To eject lancet 104, the user slides ejection slide 115 forward toward piercing aperture 110 from its at rest position. This in turn causes ejection actuator 121 to slide within housing, engaging and ejecting lancet 104 as described below. A spring or other biasing device (not shown) can be provided to bias ejection slide 115 and ejection actuator 121 in their most rearward position so as to avoid unintended ejection of lancet 104.

Ejection actuator 121 operates in conjunction with a locking member 432, which is disposed between top surface of main body 420 and lower jaw 264 of lancet carrier 208. The function of locking member 432 is to restrain the release of the lancet body 122 from the upper and lower jaws 262, 264 of the lancet carrier 208 until the lancet sleeve 130 has been fully extended by the ejection actuator 121.

Locking member 432 has an elongated body 434 having an upper surface 436 and a lower surface 438. Near its front end 440, elongated body 434 forms an upwardly facing bar 442 and a downwardly facing convex surface 444. At its rear end, elongated body 434 is pivotally mounted to lancet carrier 208 by pivot 446, so as elongated body 434 rotates about this pivot, its front end 440 is raised and lowered relative to the lower jaw 264 of lancet carrier 208.

Locking member 432 is aligned in parallel superposition with ejection actuator 121 so that locking member 432 rests on a top surface 422 of ejection actuator 121. Top surface 422 includes an upwardly-facing concave recess 450 sized and shaped to hold the downwardly facing convex surface 444 of locking member 432. When ejection actuator 121 is in its most rearward position, convex surface 444 is aligned with and rests in concave recess 450. In this position, bar 442 is clear of lower jaw 264.

Figure 46A:
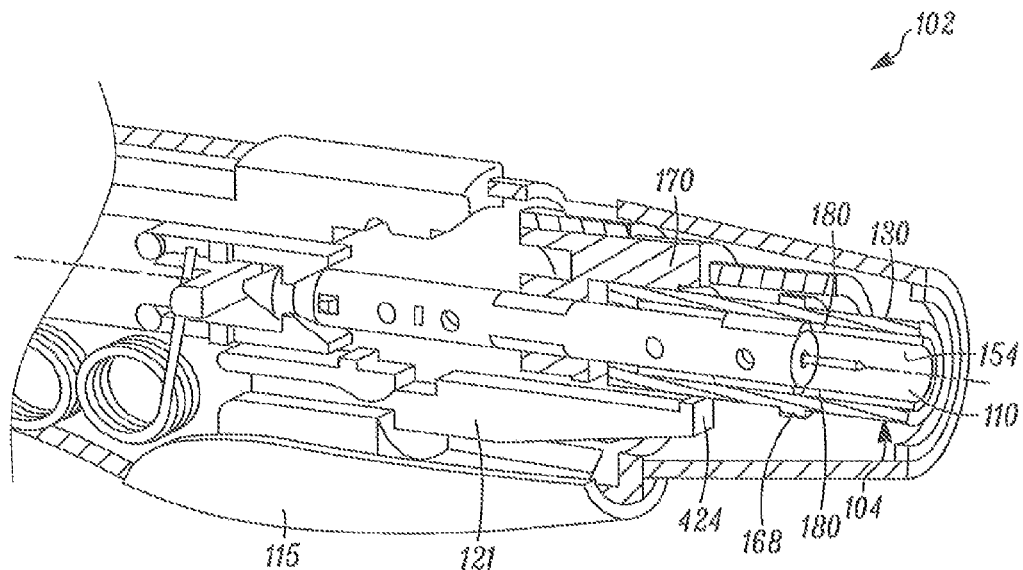
FIGS. 46a-46d are a series of cut-away right-hand perspective views of the lancing device of FIG. 1, illustrating the operation of the ejection slide and ejection actuator.

FIGS. 46a through 46d illustrate the operation of the ejection slide 115 and ejection actuator 121. After insertion of lancet 104 and operation of lancing device 102, ejection slide 115 and ejection actuator 121 are in their rearmost at rest positions, as shown in FIG. 46a. To eject lancet 104, the user slides ejection slide 115 forward toward piercing aperture 110. The resulting sliding motion of ejection actuator 121 causes finger 424 to move forward through slot 222 in receiver 170.

Figure 46B:
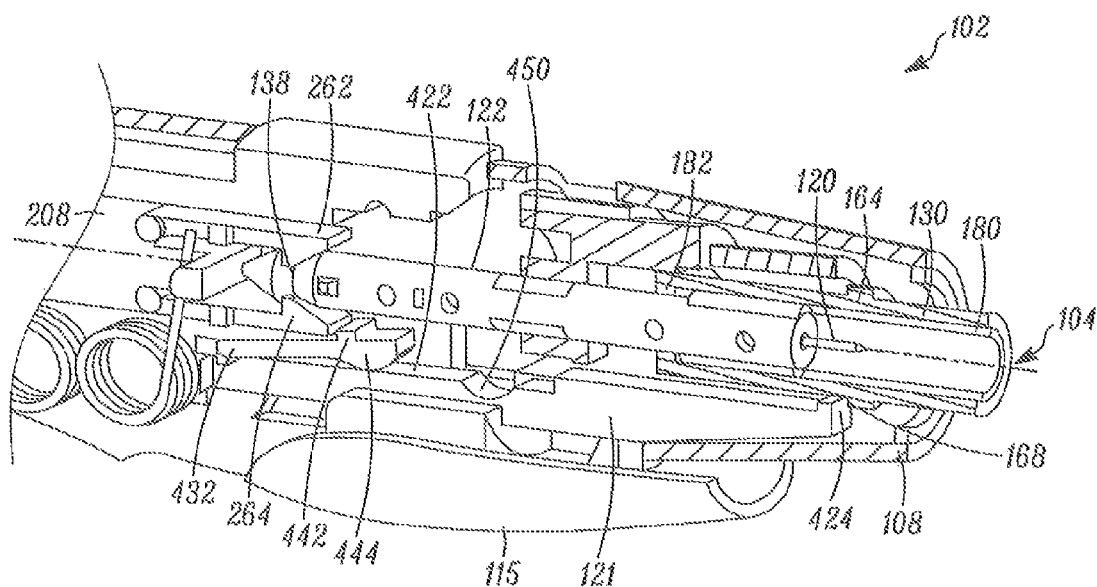

Referring to FIG. 46b, as ejection actuator slides 115 slides forward, convex surface 444 of locking member 432 slides out of concave recess 450 and onto top surface 422 of ejection actuator 121. As a result, bar 442 is thrust upward so that it engages with the underside of lower jaw 264 forcing lower jaw 264 to remain clamped about neck 138 of lancet body 122. It will be appreciated that in order for sleeve 130 to slide into the desired extended position (thus protecting sharp tip 120), it is helpful that lancet body 122 and lancet carrier 208 remain stationary. However, as lancet sleeve 130 moves forward, it may exert a force on lancet body 122 due to friction as the sleeve 130 slides axially over lancet body 122. This force has the tendency to pull lancet body 122 out of lancet carrier 208 and along with sleeve 130, thus preventing sleeve 130 from fully extending relative to lancet body 122. Even if lancet body 122 remains engaged by lancet carrier 208, the forward thrust on lancet 104 may move lancet carrier 208 forward. Locking member 432 restrains the release of the lancet body 122 from the upper and lower jaws 262, 264, thus holding lancet body stationary while lancet sleeve is pushed forward by finger 424. At the same time, it blocks forward movement of lancet carrier 208.

Figure 10:
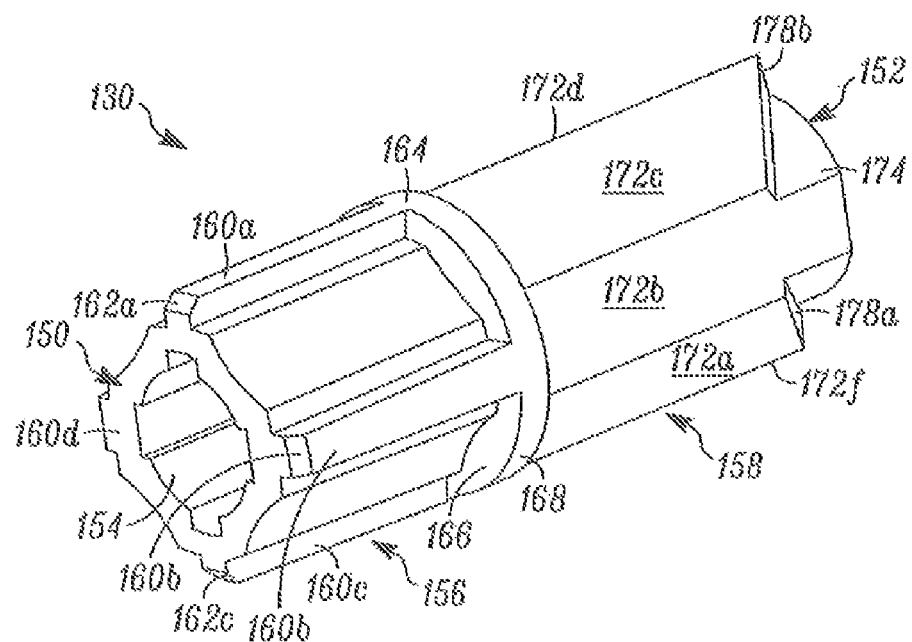
FIG. 10 is a perspective view of the sleeve in the lancet of FIG. 5.
Figure 11:
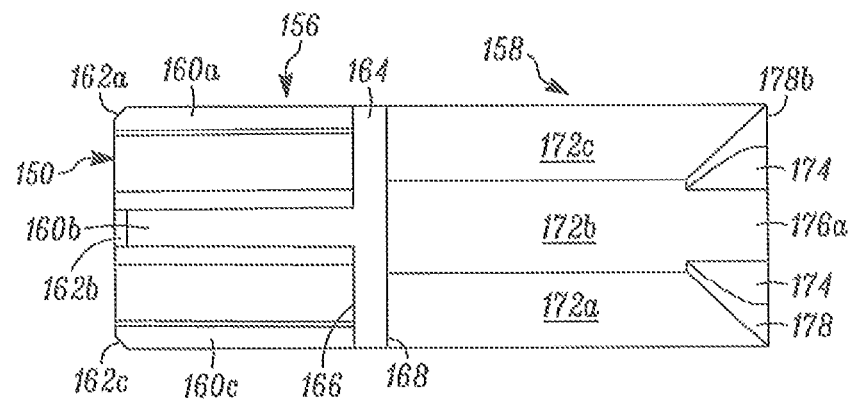
FIG. 11 is a left side view of the sleeve of FIG. 10.
Figure 12:
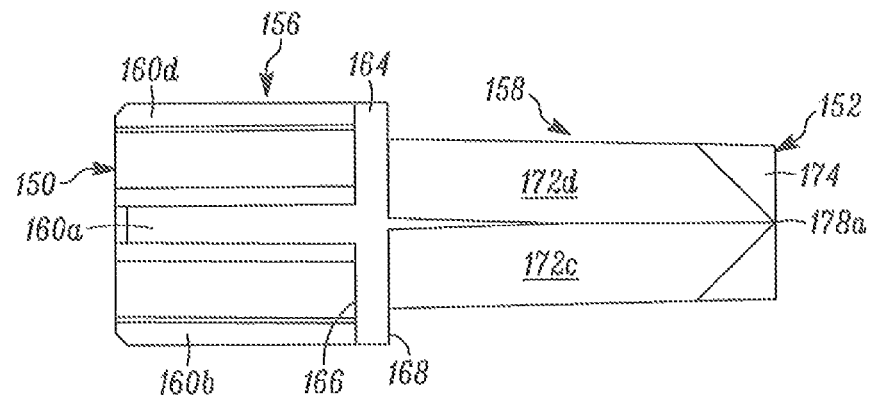
FIG. 12 is a top plan view of the sleeve of FIG. 10.

As the user continues to slide ejector 115 forward, finger 424 moves through the slot 222 in the receiver 170, until it engages ejection shoulder 168 formed in an annular flange 164 of the lancet sleeve 130 (see also FIG. 10 for more detailed view of ejection shoulder 168). Continued forward movement of the ejection actuator 121 causes finger 424 to slide lancet sleeve 130 axially over lancet body 122 in forward direction so that sleeve 130 surrounds sharp tip 120 in the extended protective position.

Figure 46C:
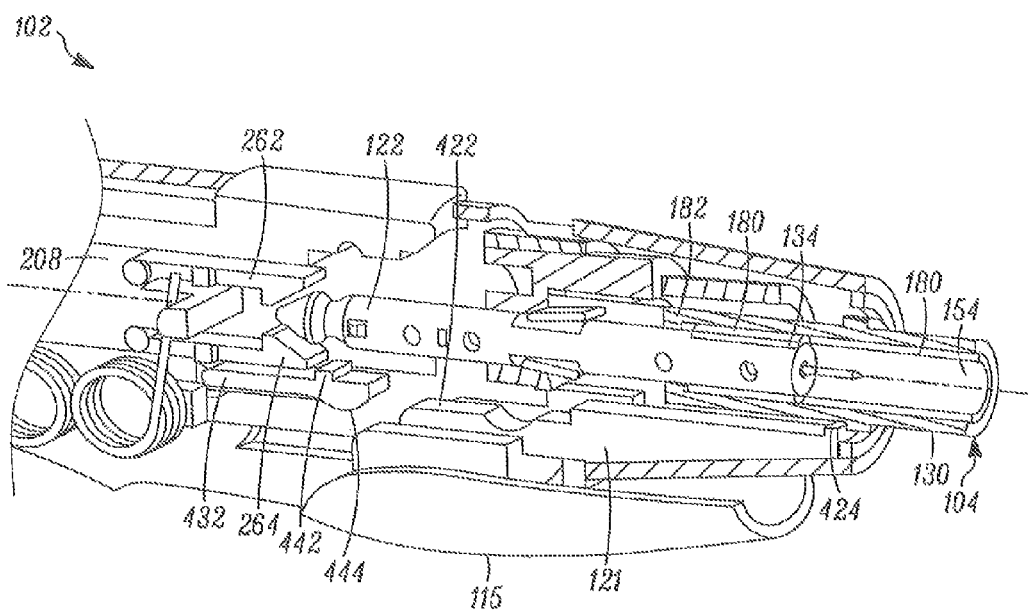

Referring to FIG. 46c, when ejection actuator 121 has pushed sleeve 130 to its most forward position relative to lancet body 122, guide ribs 134 of lancet body 122 engage backstops 182 at the end of grooves 180 inside the inner chamber 154 of sleeve 130. Further movement of sleeve 130 by ejection actuator 121 requires that lancet body 122 be pulled out of jaws 262, 264 of lancet carrier 208. At this same point in the forward travel of ejection actuator 121, the convex surface 444 locking member 432 has reached the end of top surface 422 and drops off the rear end of ejection actuator 121. This action allows bar 442 to fall below the lower jaw 264 and permits lower jaw 264 to be opened in response to urging of lancet body 122.

Figure 46D:
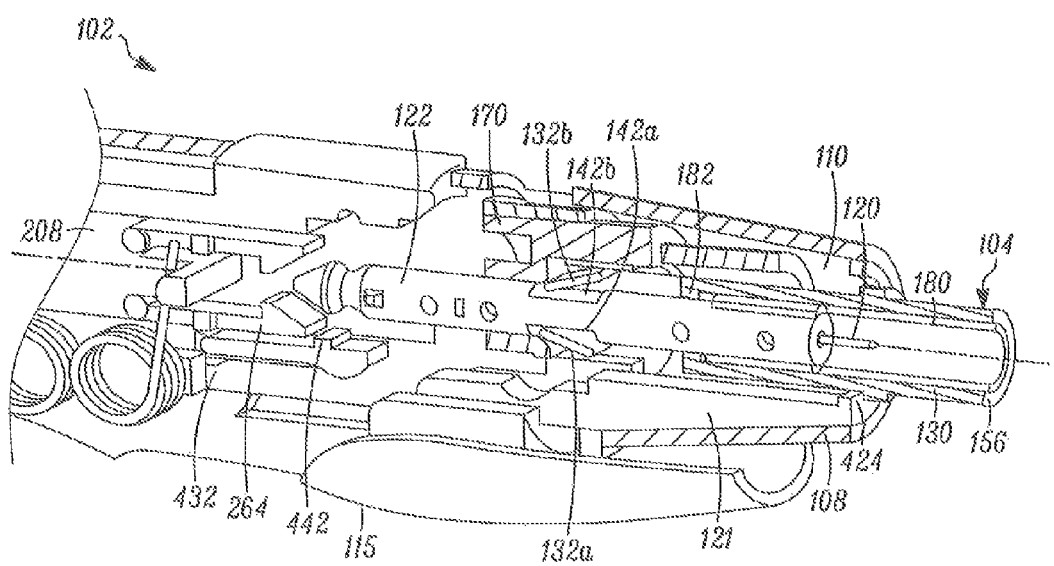

Referring to FIG. 46d, as continued movement of ejection actuator 121 pushes lancet sleeve 130 and lancet body 122 forward, wings 132a, 132b on lancet body 122 slide from the rearward internal portion 402 to the forward internal portion 400 of receiver 170. In the wider forward internal portion 400, wings 132a, 132b (which had been folded into wing wells 142a, 142b) are no longer deformed and restrained by rear guide walls 408 of receiver 170, and accordingly wings 132a, 132b flap out into an extended V-shaped configuration (See FIG. 5). In this extended V-shaped configuration, wings 132a, 132b engage and prevent sleeve 130 from moving axially rearward and thus exposing sharp tip 120.

With ejection slide 121 moved to its full forward position, finger 424 has pushed sleeve 130 so that its front portion 156 protrudes through piercing aperture 110 of cap 108. The user may now engage the protruding front portion 156 to pull lancet 104 out of the lancing device 102. Because the sleeve 130 has been extended to surround needle's sharp tip, it is less likely that the user will prick himself or herself in grasping the lancet 104 for removal. Lancet 104 may also be dropped out of lancing device 102 without the user touching lancet 104 at all.

Figure 47A:
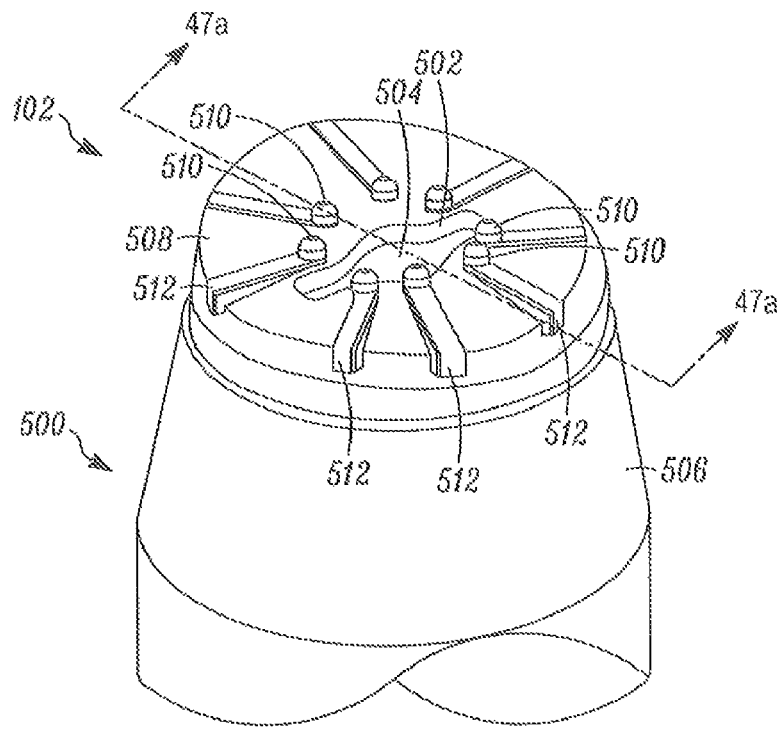
FIG. 47a is a partial perspective view of a lancing device in accordance with a further embodiment.
Figure 47B:
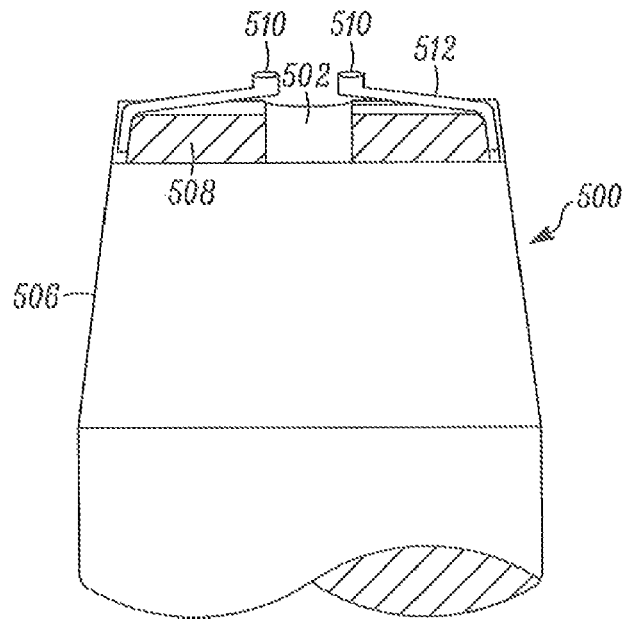

FIGS. 47a and 47b show another embodiment of lancing device 102, which includes a skin-engaging cap 500 with additional features for improving the user's comfort, expressing blood from the site of a lancing incision and stabilizing the device on the skin. Cap 500 includes a piercing aperture 502, which in this case may be elongated with a enlarged center portion 504. Cap 500 has a rigid base 506 which can be opaque, and a skin-engaging cover 508 which is composed of electrometric material and can be transparent. A plurality of small bumps 510 are disposed about the piercing aperture 502 and are mounted on upwardly extending arms 512 which act as cantilevers. Arms 512 can be mounted to ridged base 506 and can extend upward at an angle (as shown) through the electrometric cover 508 so that a portion of arms 512 extends beyond the cover.

Arms 512 are flexible to permit bumps 510 to move toward cap 500 when bumps 510 are pressed against the user's skin. When bumps 510 move toward cap 500, they draw closer to the piercing aperture 502, concentrating blood near the incision. Electrometric cover 508 serves to add compliance to the skin as well as to spread the motion of bumps 510 to adjacent skin. Arms 512 can include stops or other suitable mechanisms (not shown) to limit inward movement of bumps 510. This permits lancing depth to be more predictable and less dependent upon the force applied to the user's skin.

Additional Embodiment for Depth Adjustment

Figure 50A:
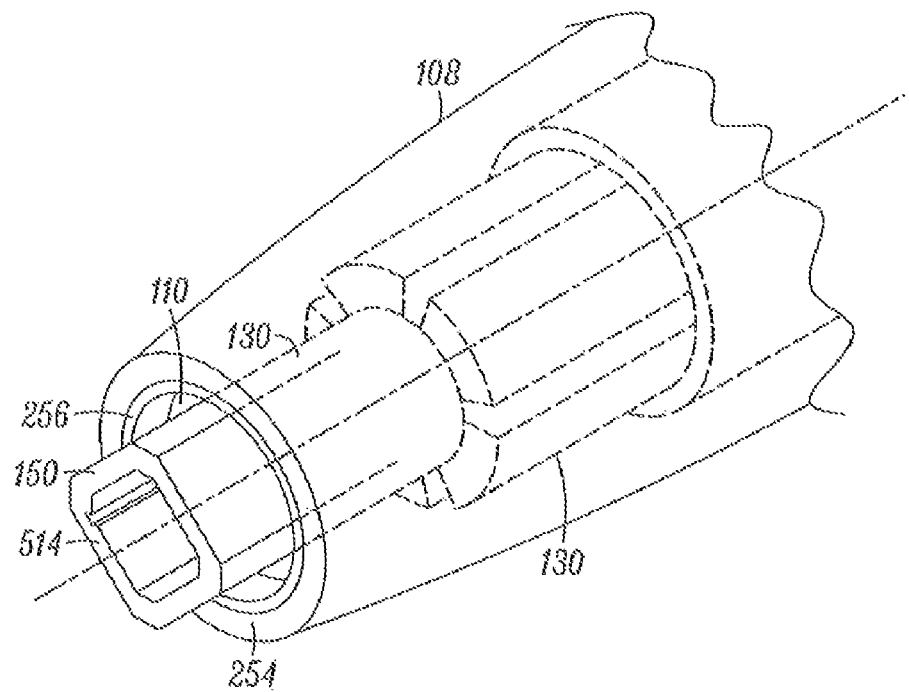
FIG. 50a is an isolated perspective view of the lancing device of FIG. 1, showing the position of the lancet sleeve protruding beyond the piercing aperture to adjust penetration depth of the needle sharp.
Figure 50B:
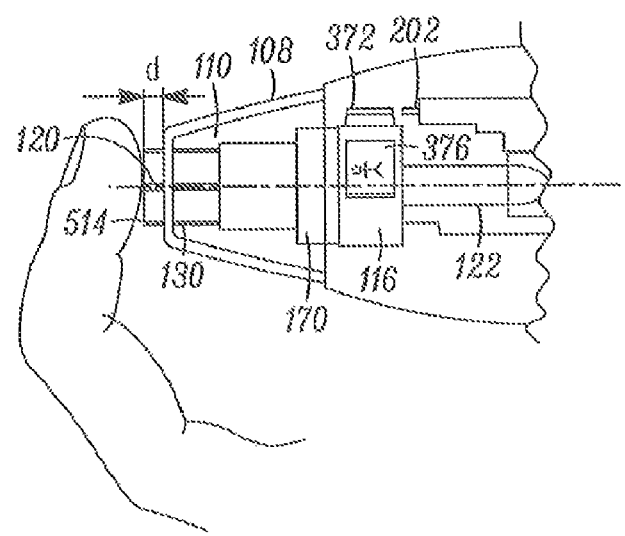
FIG. 50b is a left side view (with the housing cut away to reveal internal mechanisms) of the lancing device as shown in FIG. 50a, with the lancet sleeve protruding beyond the piercing aperture and placed on a user's skin in preparation for lancing operations.

Referring to FIGS. 50a and 50b, an alternative embodiment is illustrated for adjusting penetration depth of sharp tip 120. In this embodiment, sleeve 130 slides through the front end of the cap 108 by the motion of AST mode actuator ring 116 and receiver 170, as described above. However, cam trails 368 and 370 of receiver 170 are cut to permit receiver 170 to move a greater distance toward cap 108 when AST mode actuator ring 116 is rotated. In this manner, the front end 150 of sleeve 130 can be extended through the piercing aperture 110 to provide a skin engaging surface 514 that protrudes from the plane of piercing aperture 110 by a distance "d" as shown in FIG. 50b.

Because sleeve 150 extends beyond piercing aperture 110, it spaces the user's finger away from needle 118 and reduces by the distance "d" the length of sharp tip 120 that is exposed to penetrate the user's skin. The farther out sleeve 130 is extended, the less distance sharp tip 120 penetrates the user's skin.

Referring to FIGS. 50a and 5b, sleeve 130 is held by receiver 170, which in turn is controlled in cam-like fashion by AST mode actuator ring 116. To adjust the position of sleeve 130 relative to piercing aperture 110, the user rotates AST mode actuator ring 116, which drives the receiver 170 (and hence the lancet sleeve 130) axially toward or away from the skin-engaging surface 254 of the cap 108 (depending on which direction the user rotates AST mode actuator ring 116). It will be seen that actuator ring 116 can operate as a user-operable switch or control to adjust penetration depth by moving sleeve 130 into a first position where it extends beyond piercing aperture 110 and a second position (see for example FIG. 33) where sleeve 130 is withdrawn from piercing aperture 110 so that sleeve 130 no longer impinges on the user's skin when cap 108 is placed into contact with the user prior to firing lancing device 102. AST mode actuator ring can also be rotated to a third position, for example, where sleeve 130 extends beyond piercing apertures 110 by a distance less than or greater than distance d. By selectively positioning AST mode actuator ring, the user can achieve a desired depth penetration level. Detents and indicia can be provided on AST mode actuator ring 116 to assist users in selecting a desired position.

Additional Embodiment of Lancing Device

Figure 51:
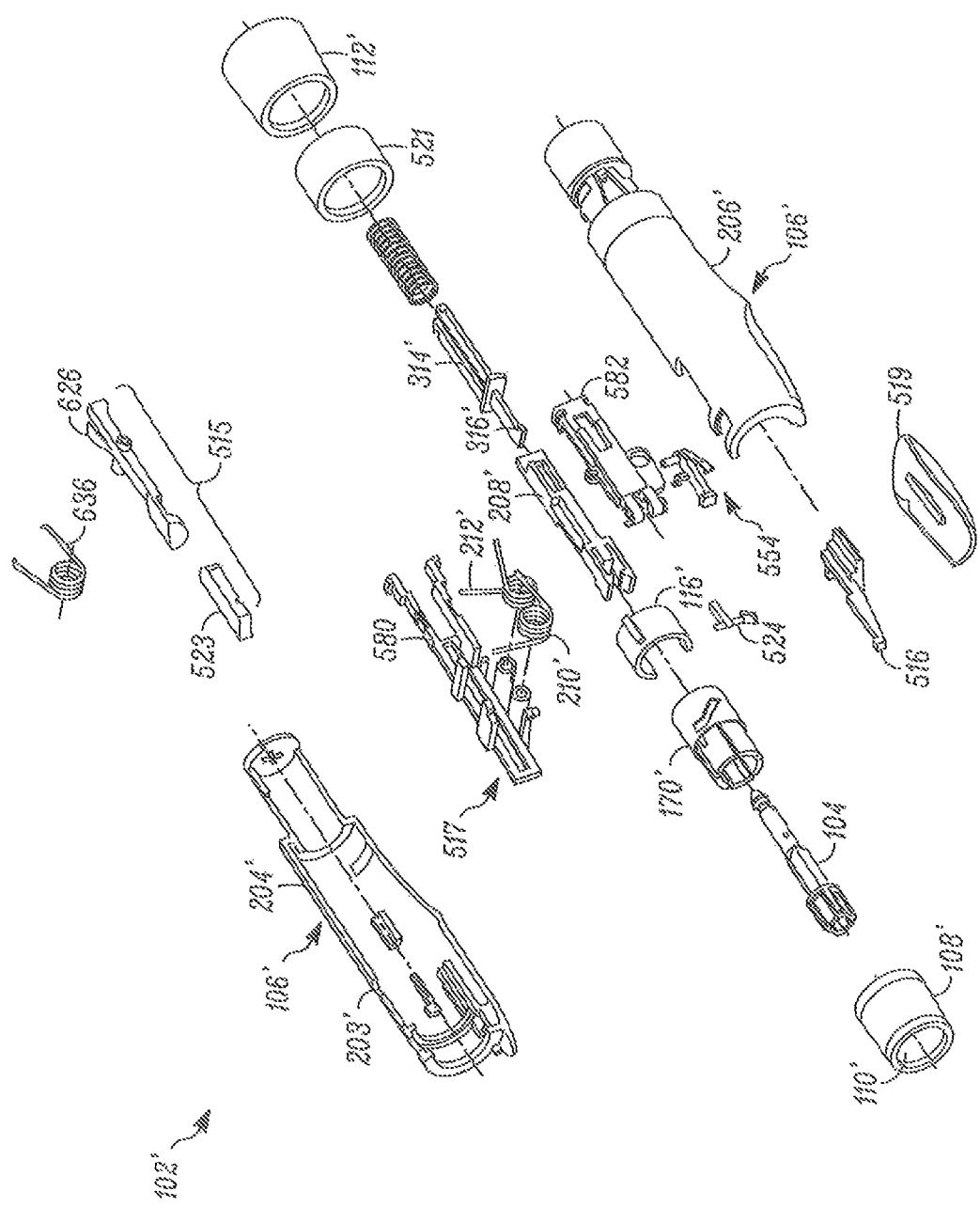
FIG. 51 is an exploded perspective view of a lancing device in accordance with a second embodiment of the invention.

Referring to FIG. 51, alternative embodiment of lancing system 100 includes a lancing device 102' and a lancet such as lancet 104. Lancing device 102' is similar in construction and operation to lancing device 102, and only those features that are different are described in detail. Lancing device 102' is operated by a user to draw a sample of blood or other bodily fluid from the body such as for diagnostic purposes. Lancing device 102' includes a housing 106' with a skin-engaging cap 108' having a piercing aperture 110' and a cocking handle 112' used to cock an internal firing mechanism (described below). Cocking handle 112' includes an elongated rod 314' extending into the interior of housing 106' that terminates in an L-shaped cocking hook 316'.

Lancing device also includes a trigger assembly 515 that includes a trigger button 523 that projects through a trigger aperture 203' in housing 106'. An ejection slide 519 is provided to eject lancet 104 from lancing device 102' after use. Housing 106' includes right- and left half portions, 204' and 206', respectively.

An AST mode actuator ring 116' is provided which operates with a receiver 170' substantially as described above with respect to actuator ring 116 and receiver 170.

A carriage assembly 517 is disposed within housing 106' for sliding axial movement to and away from piercing aperture 110'. Included in carriage assembly 517 is a slidable lancet carrier 208' that engages lancet 104, a drive spring 210' that propels the lancet carrier 208' toward piercing aperture 110' to drive lancet 104 to pierce the user's skin or other bodily tissue. Also included with in carriage assembly 517 is a return spring 212' that propels lancet carrier 208' rearward to withdraw lancet 104 from the user's skin after piercing. If desired, lancing device 102' can be equipped with other drive mechanisms, such as a coil spring, a leaf spring, and electro-mechanical or electromagnetic drive or other suitable mechanisms known in the art to propel lancet carrier 208' axially within housing 106'.

Lancing device 102' includes a depth adjuster 521 which operates in concert with carriage assembly 517. As explained below, the user's rotation of depth adjuster 521 causes carriage assembly 517 to slide axially within the housing 106' to regulate penetration depth of lancet 104 when lancing device 102' is fired.

Ejection Slide and Ejection Actuator

Referring to FIGS. 52 and 53, the structure and operation of an ejection actuator 516 and an ejection slide 519 (shown in FIG. 51), whose structure and operation are substantially the same as ejection actuator 121 and ejection slide 115 discussed above.

Ejection actuator 516 is slidably mounted within housing 106' and includes an elongated main body 518 with a spine 520 extending upwardly therefrom along the longitudinal extent of the main body. Spine 520 includes a finger 522 whose structure and function is the same as that of finger 424 described above. Ejection actuator 516 operates in conjunction with a locking member 524 (which is used in place of the locking member 432 described in the previous embodiments).

To eject lancet 104 (not shown in FIGS. 52 and 53), the user slides ejection slide (not shown in FIGS. 52 and 53) forward toward piercing aperture 110'. This in turn causes ejection actuator 516 to slide within housing, engaging and ejecting lancet 104 as described above in reference to FIGS. 45-46. Ejection actuator 516 operates in conjunction with a locking member 524 to restrain movement of lancet carrier 208' during operation of ejection actuator 516 as described below.

Referring to FIGS. 54-59, locking member 524 is described. Locking member 524 includes a cylinder 526 from which extend upper arm 528 and lower arm 530. Upper arm 528 defines an abutment surface 532 near its distal tip. Lower arm 530 defines a front surface 534 and a rear surface 536 near it distal end.

Figure 52A:
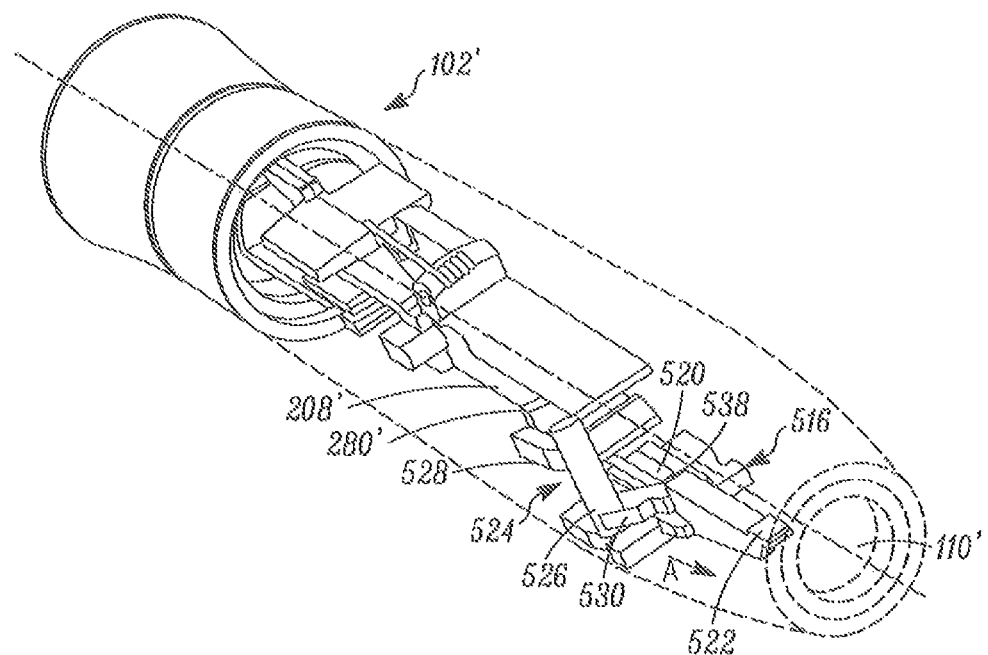
FIG. 52a is a perspective view (with the housing in phantom lines to reveal internal mechanisms) of the lancing device of FIG. 51, showing a stopper in an open position.
Figure 52B:
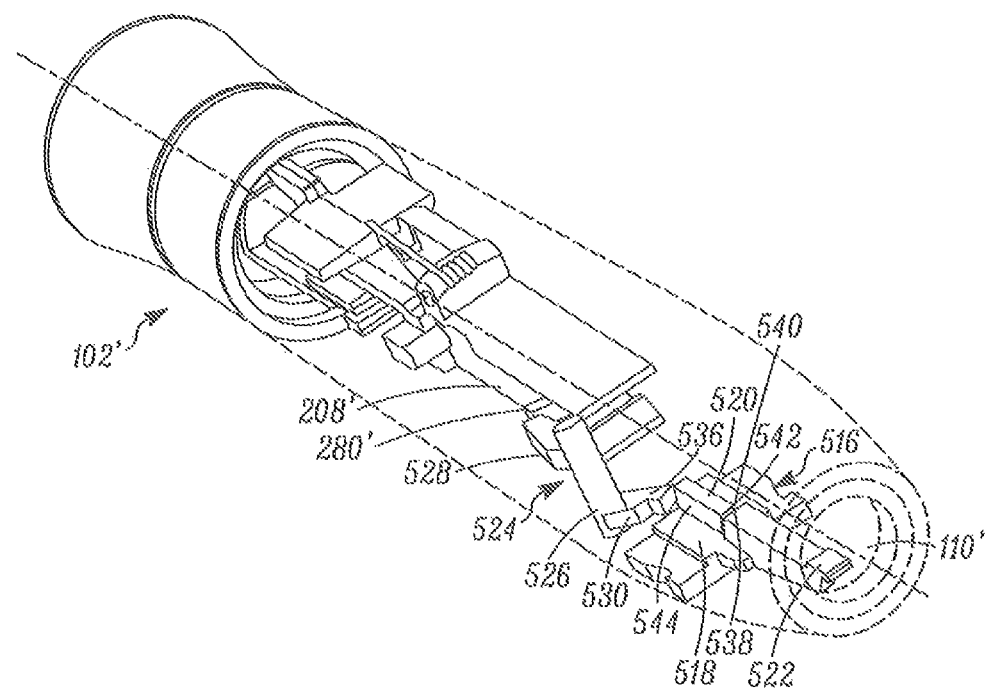
FIG. 52b is a perspective view (with the housing in phantom lines to reveal internal mechanisms) of the lancing device of FIG. 52a, showing the stopper in a closed position.

Referring to FIG. 52a, cylinder 526 is mounted to housing to permit rotation about its major axis. Lower arm 530 extends from cylinder 526 so that its distal end extends into a notch 538 in spine 520 of ejection actuator 516 when ejection actuator is at its rearward "at-rest" position. Notch 538 defines a front wall 540 and rear wall 542 as best seen in FIGS. 52b and 53b. In this "open" configuration, upper arm 528 is clear of an engagement boss 280' on lancet carrier 208', as shown in the top plan view of FIG. 53a. Accordingly, locking member 524 does not in this configuration prevent forward axial movement of lancet carrier 208'.

As ejection actuator 516 slides forward (in the direction of arrow A in FIGS. 52a and 53a), rear wall 542 of notch 538 impinges on rear surface 536 of lower arm 530, driving lower arm 530 away from the central axis of lancing device 102' and causing locking member 524 to pivot about cylindrical main body 526 in clockwise direction D (FIG. 53b) to swing upper arm 528 to a position adjacent to a front of drive spring engagement boss 280' on lancet carrier 208', as shown in FIGS. 52b and 53b. In this "closed" configuration, the abutment surface 532 of upper arm 528 abuts drive spring engagement boss 280' in blocking engagement to block forward movement of lancet carrier 208', as best seen in FIG. 53b.

Figure 45:
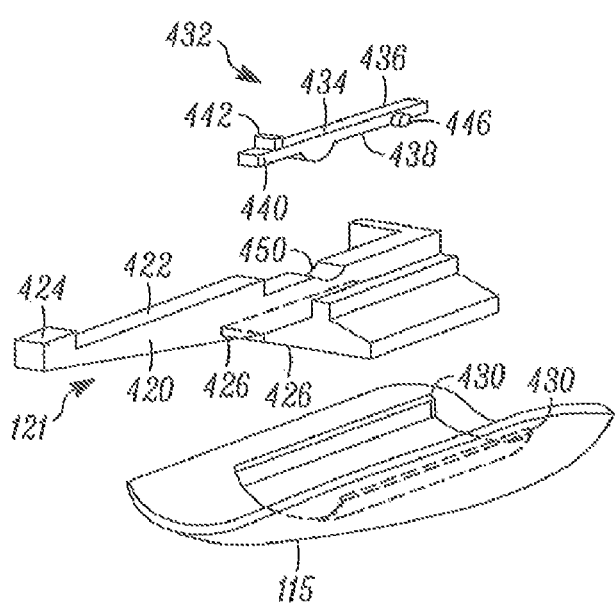
FIG. 45 is an exploded perspective view of the ejection slide, ejection actuator and locking member of FIG. 17.

As with the embodiments of FIGS. 45-46, ejection actuator 516 engages sleeve 130 to eject lancet 104. As ejection actuator 516 pushes sleeve forward to its extended position, lancet body 122 is held by lancet carrier 208' by a pair of jaws similar in construction to jaws 262 and 264 described above. As lancet sleeve 130 moves forward, it may exert a force on lancet body 122 due to friction as the sleeve 130 slides axially over lancet body 122. This force has the tendency to pull lancet body 122 out of lancet carrier 208' and along with sleeve 130, thus preventing sleeve 130 from fully extending relative to lancet body 122. The snap closure of jaws on lancet carrier 208' may be sufficiently stiff to prevent removal of lancet body 122 as lancet sleeve 130 is pushed forward. However, the thrust imposed on lancet body 122 is communicated to lancet carrier 208', which then has a tendency to move. In the closed position, as shown in FIGS. 52b and 53b, locking member 524 engages a boss 280' extending from lancet carrier 208' to prevent forward movement of lancet carrier 208'. As ejection actuator 516 continues to move forward, the distal end of lower arm 530 is thrust out of notch 538 and abuts a sidewall 544 of spine 520, which prevents rotation of locking member to its open position shown in FIG. 52a.

Figure 53A:
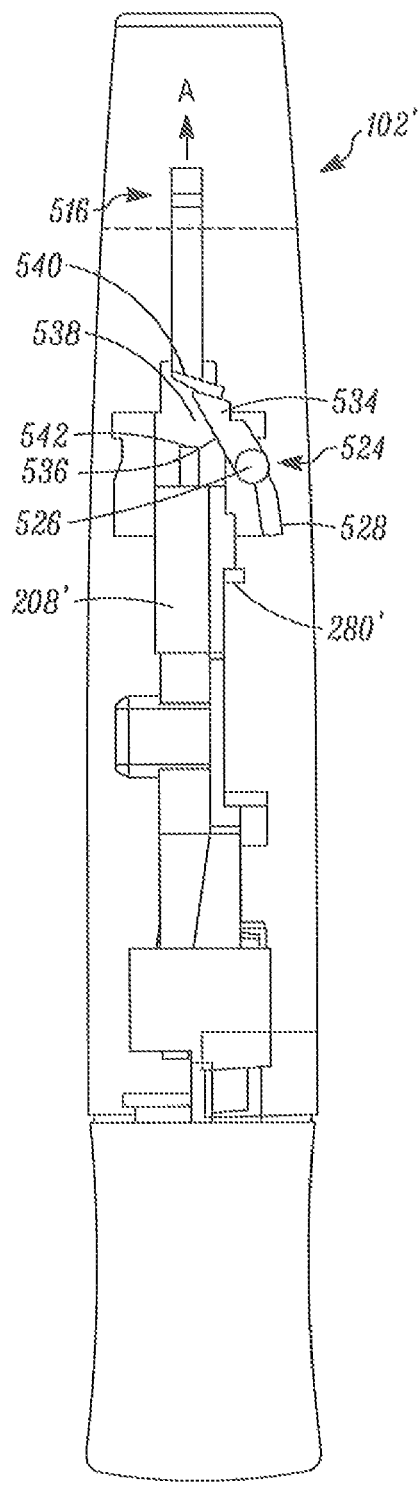
FIG. 53a is a top plan view (with the housing in phantom lines to reveal internal mechanisms) of the lancing device as shown FIG. 52a, with the stopper in an open position.
Figure 53B:
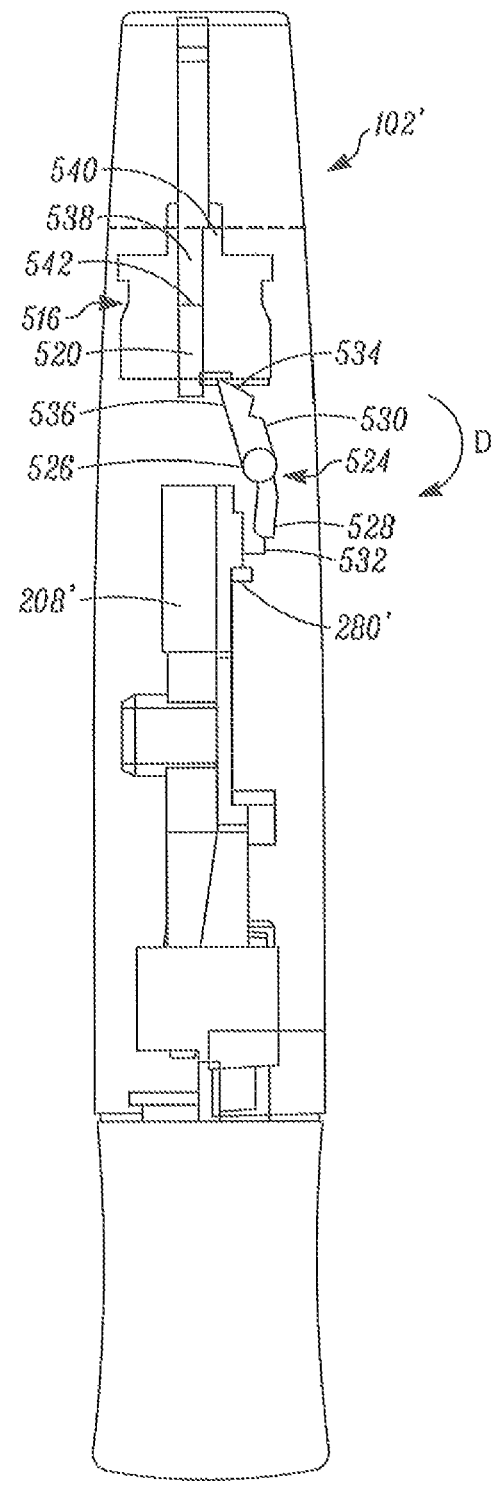
FIG. 53b is a top plan view (with the housing in phantom lines to reveal internal mechanisms) of the lancing device as shown in FIG. 52b, with the stopper in a closed position.
Figure 54:
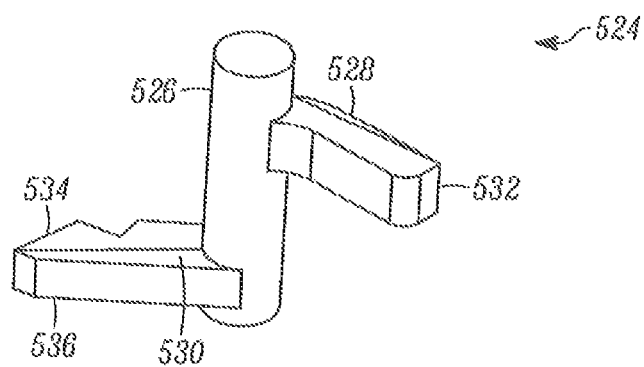
FIG. 54 is a perspective view of the stopper of FIGS. 52a and 52b.
Figure 55:
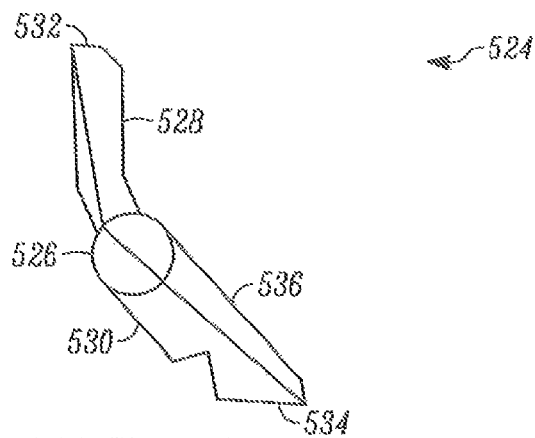
FIG. 55 is a top plan view of the stopper of FIG. 54.
Figure 56:
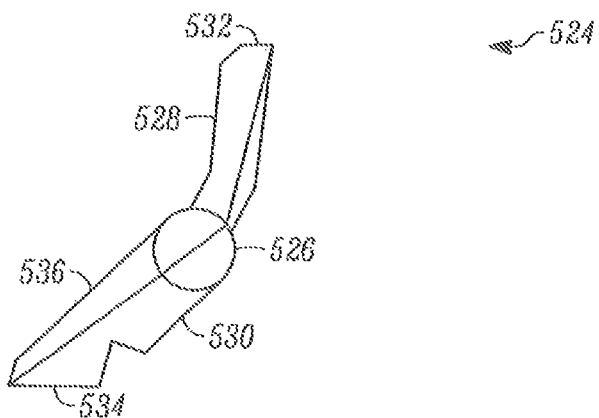
FIG. 56 is a bottom plan view of the stopper of FIG. 54.
Figure 57:
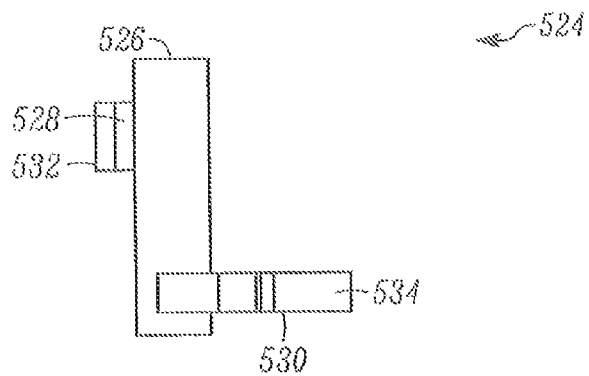
FIG. 57 is front elevation view of the stopper of FIG. 54.
Figure 58:
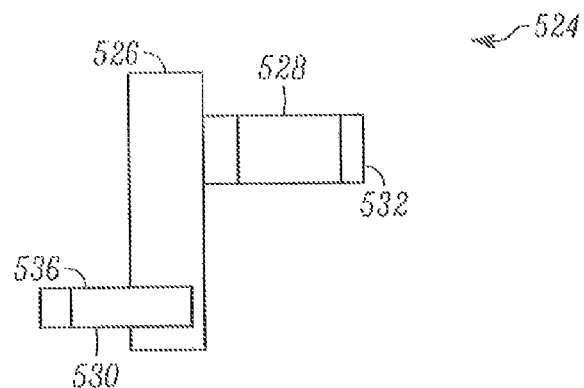
FIG. 58 is left-side elevation view of the stopper of FIG. 54.

After lancet 104 is ejected, ejection actuator 516 returns rearward to its at-rest position as shown in FIGS. 52a and 53a. As ejection actuator 516 returns to its rearward at-rest position, front wall 540 pushes lower arm 530 rearward, pivoting locking member 524 about its cylindrical body 526 into the open configuration shown in FIGS. 52a and 53a.

It will appreciated that that when locking member 524 is in its closed configuration, substantially all of the force exerted on locking member 524 by lancet carrier 208' is transmitted to housing 106' via main cylindrical body 526, whose interface with housing 106' acts as a bearing surface, which is static while locking member 524 is in its closed configuration. Other bearing surfaces can be provided as well (apart from ejection actuator 516) and substantially all of the force exerted by lancet carrier 208' can be distributed amongst these bearing surfaces in any desired proportion.

Additionally, the forward thrust of lancet carrier 206' upon upper arm 528 urges locking member 524 to continue rotating in a clockwise direction of arrow D (as shown in FIG. 53b) urges upper arm 528. This can reduce or eliminate the force directed onto ejection actuator 516 via lower arm 530, which in turn reduces the friction between lower arm 530 of locking member 524 and sidewall 544 of ejection actuator 516, as ejection actuator 516 moves forward past lower arm 530.

Referring to FIG. 53b, it will be seen that the forward thrust of lancet carrier 206' urges locking member 524 to rotate in the clockwise direction of arrow D because the upper arm 528 has rotated sufficiently far in the clockwise direction about cylinder 526.

Figure 59:
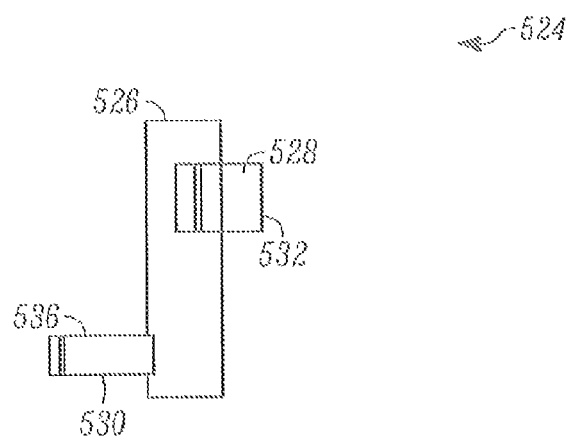
FIG. 59 a rear elevation view of the stopper of FIG. 54.
Figure 59A:
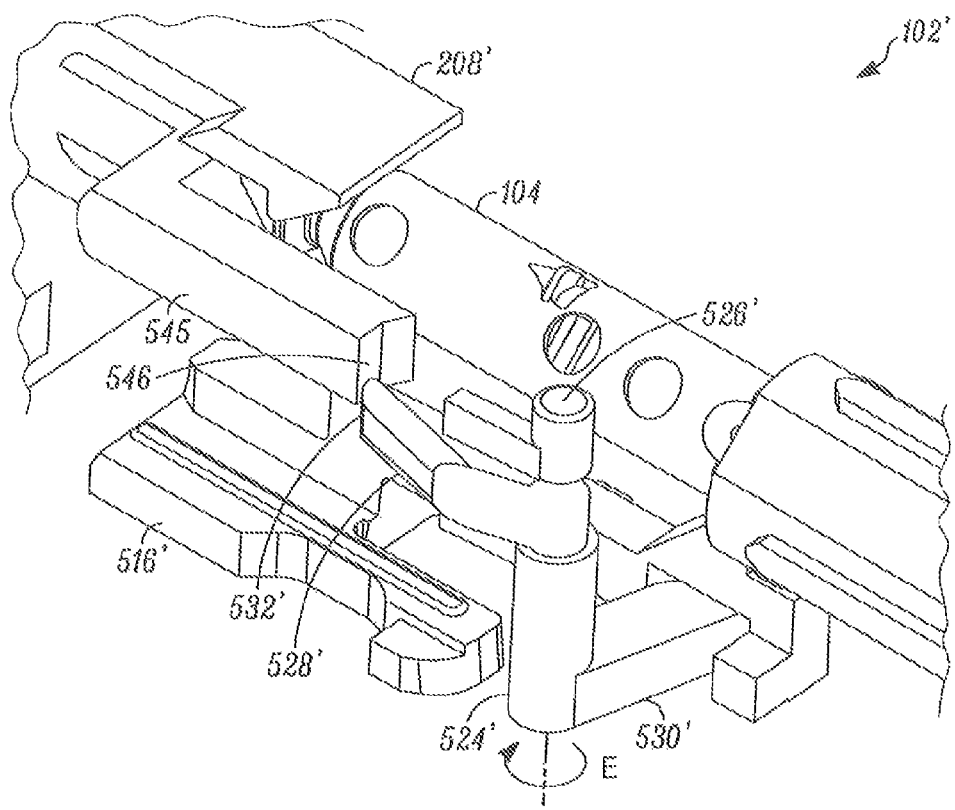
FIG. 59A is partial perspective view of an alternative embodiment of the lancing device of FIG. 51, showing an ejection slide engaging a stopper in an open position.
Figure 59B:
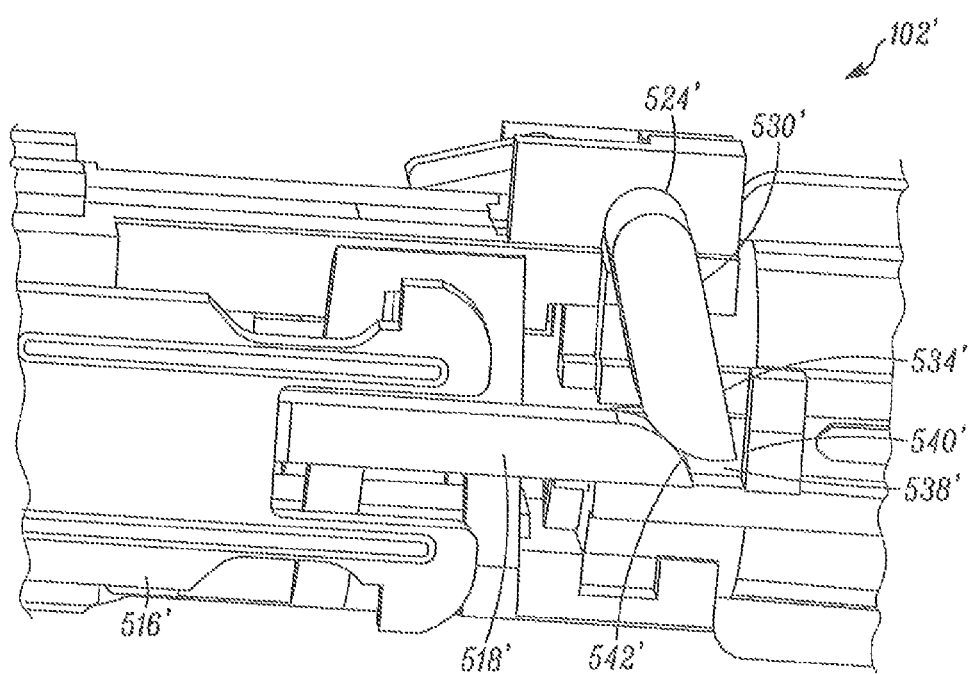
FIG. 59B is a bottom plan view of an the engagement slide and slide and stopper of FIG. 59A.

An alternative embodiment in the form of ejection actuator 516' and locking member 524' is illustrated in FIGS. 59A and 59B. Ejection actuator 516' and locking member 524' operate substantially as described above with respect to ejection actuator 516 and locking member 524. Ejection actuator 516' is slidably mounted within housing 106' and includes an elongated main body 518'. Locking member 524' includes a cylinder 526' from which extend upper arm 528' and lower arm 530'. Upper arm 528' defines an abutment surface 532' near its distal tip. Lower arm 530' defines a front surface 534' and a rear surface 536' near it distal end.

Lower arm 530' extends from cylinder 526' so that its distal end extends into a notch 538' in elongated main body 518'. Notch 538' defines a front wall 540' and rear wall 542' as best seen in FIG. 59B. To facilitate the rotation of lower arm 530' about cylinder 526' when engagement actuator 516' moves forward, rear wall 542' and rear surface 536' have corresponding convex contoured surfaces.

Referring to FIG. 59A, lancet carrier 208' includes a projection 545 jutting forward to engage abutment surface 532' of upper arm 528'. The forward end of projection 545 includes a beveled front face 546 that defines a V-shaped contour. Abutment surface 532' is tapered to engage face 546 so that forward movement of lancet carrier 208' urges locking member 524' to rotate about cylinder 526' in the direction of arrow E. This can reduce or eliminate the force directed onto ejection actuator 516' via lower arm 530', which in turn reduces the friction between lower arm 530' of locking member 524' and sidewall 544 of ejection actuator 516', as ejection actuator 516' moves forward past lower arm 530'.

If desired, a bias element such as a spring can be included to also urge locking member 524' to rotate in the direction of arrow E.

Figure 59C:
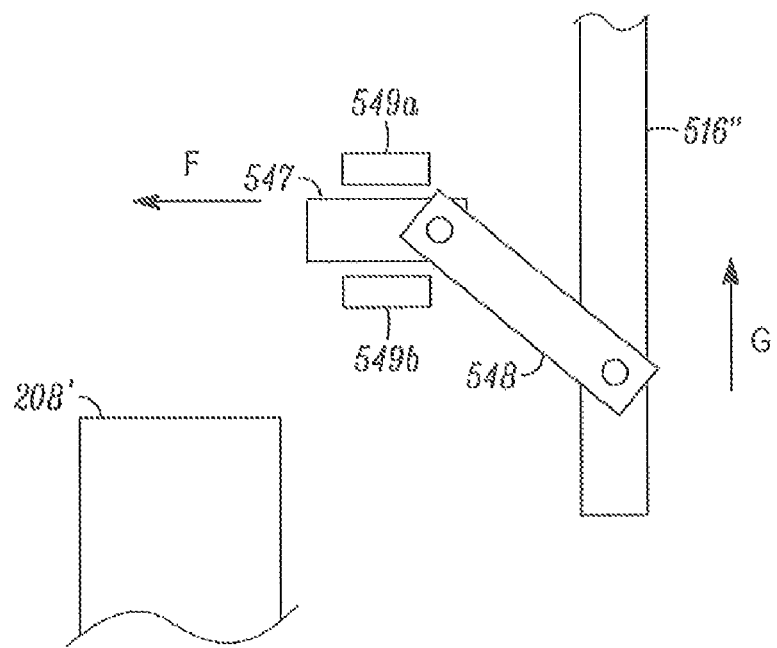
FIG. 59C is a top plan view of an engagement slide and stopper in accordance with an alternative embodiment of the invention, showing the stopper in an open position.
Figure 59D:
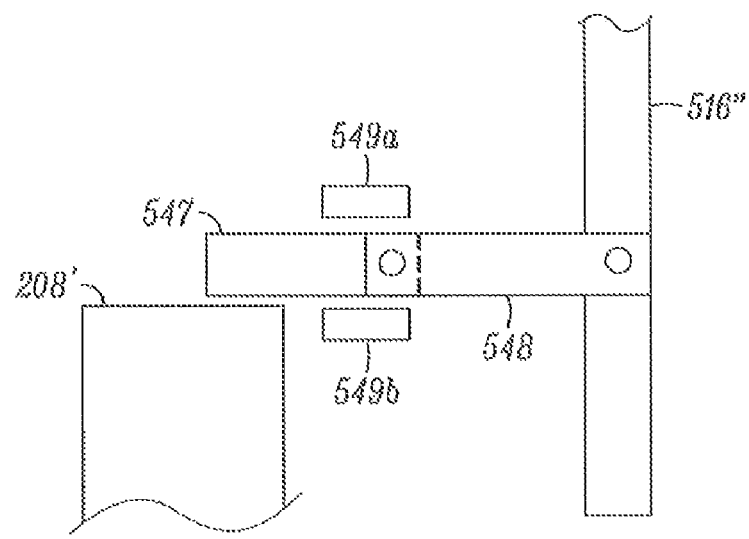
FIG. 59D is a top plan view of the engagement slide and stopper of FIG. 59C, showing the stopper in a closed position.

Referring to FIG. 59C, another embodiment is illustrated in the form of locking member 547. Locking member 547 is mounted to housing 106' (not shown in FIG. 59C) by guide tracks 549a, 549b to permit locking member 547 to slide laterally in the direction of arrow F between a position (as shown in FIG. 59C) where locking member 547 does not block the forward movement of lancet carrier 208' and a position where locking member 547 does block the forward movement of lancet carrier 208' (as shown in FIG. 59D). Locking member 547 is coupled to ejection actuator 516" by a rod 548 that is pivotally mounted to both locking member 547 and ejection actuator 516". As ejection actuator 516" moves forward in the direction of arrow G during ejection, rod 548 urges locking member 547 away from ejection actuator 516" and into blocking engagement with lancet carrier 208'. It will be noted that when locking member 547 is blocking the forward movement of lancet carrier 208', substantially all of the forward force imposed by lancet carrier 208' can be borne by the bearing surfaces of guide tracks 549a, 549b, which can be close enough to locking member 547 an lancet carrier 208' to reduce or eliminate torque imposed on rod 548.

Lancet Interlock

Referring to FIGS. 60 through 71, an interlock member 554 is illustrated. Interlock member 554 prevents lancet 104 (shown in FIG. 61c) from being inserted for operable engagement into lancing device 102' when lancing device 102' is cocked. The interlock member selectively prevents the lancet from being operably engaged for use. This feature reduces the chance that a user will accidentally prick himself or herself while loading lancet 104 into lancing device 102'.

Interlock member 554 cooperates with a trigger assembly 515. With respect to the cocking and firing operations of lancing device 102, trigger assembly 515 operates in substantially the same manner as trigger 114 shown in FIGS. 27-30. When lancing device 102' is cocked, trigger assembly 515 pivots in see-saw fashion so that trigger button 523 moves upward to extend through a trigger aperture 203' of housing 106' (shown in phantom lines in FIGS. 60 and 61). When lancing device 102' is uncocked, trigger assembly 515 pivots in see-saw fashion so that trigger button 523 moves downward.

As explained below, trigger button 523 is coupled to interlock member 554 so that when lancing device 102' is cocked, the resulting upward movement of trigger button 523 causes interlock member 554 to swing to an engagement position (shown in FIGS. 60b and 61b) in which interlock member 554 blocks or is interposed into the path of insertion P of lancet 104 to prevent full insertion of lancet 104 into lancing device 102'. When lancing device 102' is not cocked, the resulting downward movement of trigger button 523 causes interlock member 554 to swing to a disengagement position (shown in FIGS. 60a and 61a) in which interlock member 554 does not prevent the insertion of lancet 104 into lancing device 102'.

Referring to FIGS. 62 through 69, interlock member 554 is illustrated. Interlock member 554 includes an elongated main body 556 having a blocking member 558 at its front end and an elongated cylinder 560 at its rear end. The major axis of cylinder 560 is generally perpendicular to the major axis of main body 556. Cylinder 560 is mounted to housing 106' to permit cylinder 560 to rotate about its major axis. As cylinder 560 rotates, interlock member 554 swings into and out of its engagement and disengagement positions.

A resilient cantilever spring 562 extends from an off-center rear portion of cylinder 560 and terminates in a distal portion 563 that is spaced apart from main body 556. Distal portion 563 of cantilever spring 562 engages housing 106' in a position that flexes cantilever spring 562 and urges interlock member 554 to rotate about the major axis of cylinder 560 to move blocking member 558 to its engagement position in which at least a portion of the blocking member 558 is interposed between the front end of the housing 106' and the lancet holding assembly to block full insertion of the lancet 104 into the housing 106' by blocking the path of insertion P of lancet 104 (see FIG. 61b).

As best seen in FIGS. 62-63 and 68-69, blocking member 558 includes two front-facing surfaces 564 and 565. Surfaces 564 and 565 form an angle therebetween of about 120 degrees; however, other angles and configurations can be selected.

A cam follower 566 extends upward from main body 556. As best seen in FIG. 64, cam follower 566 includes a vertical base portion 568 and horizontal finger portion 570 extending from the upper end of vertical base portion 568. Finger portion 570 is crowned by a boss 572.

Figure 60A:
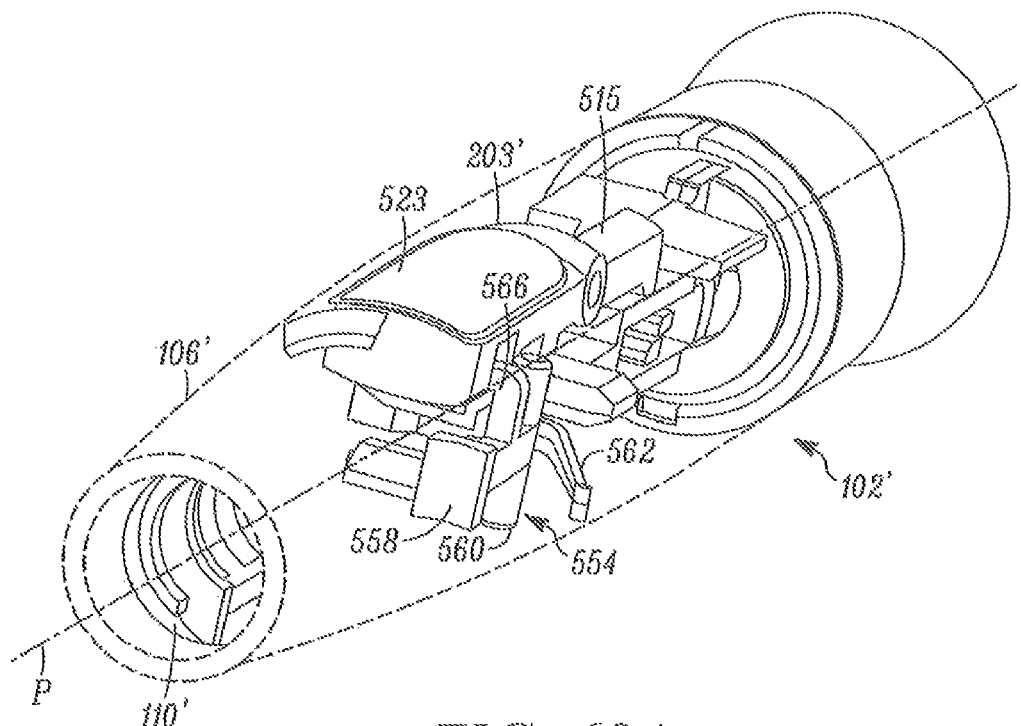
FIG. 60a is a perspective view (with the housing in phantom lines to reveal internal mechanisms) of the lancing device of FIG. 51, showing a trigger and a locking member in a disengagement position.
Figure 60B:
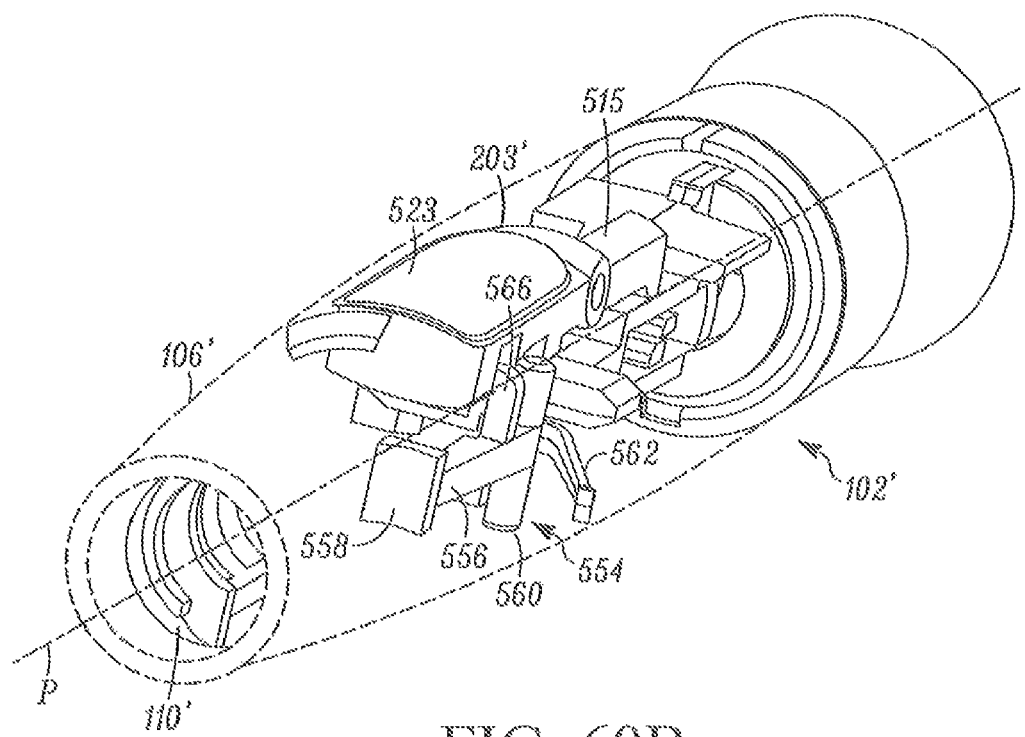
FIG. 60b is a perspective view (with the housing in phantom lines to reveal internal mechanisms) of the lancing device of FIG. 60a, showing the locking member in an engagement position.
Figure 70:
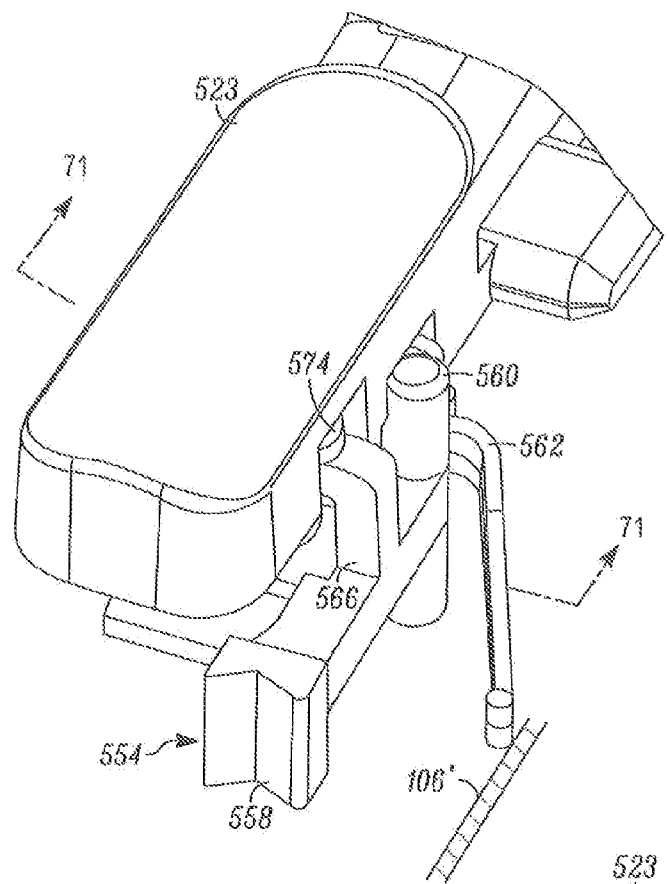
Figure 71:
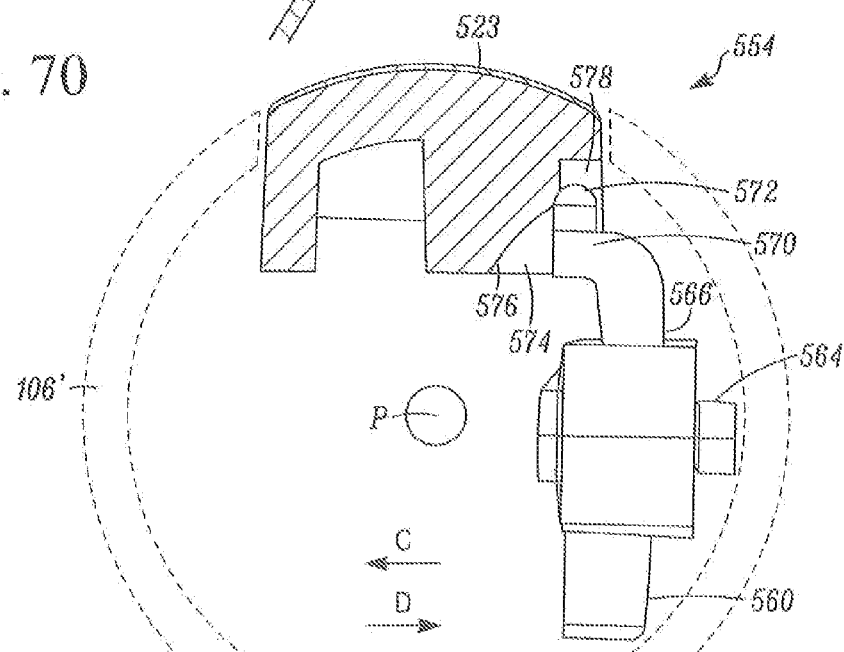
FIG. 71 is a sectional view of the trigger and locking member of FIG. 70 taken along the lines 71-71.

Referring to FIGS. 60a, 70 and 71, the interaction of trigger button 523 and interlock member 554 determines the position of interlock member 554 when lancet 104 is not inserted into lancing device 102'. Interlock member 554 is disposed within housing 106' adjacent to the trigger button 523. Trigger button 523 includes a cam trail 574 positioned to admit finger 570 of cam follower 566, as best seen in FIGS. 70 and 71. Inside of cam trail 574 is a sloped cam surface 576, against which boss 572 engages under the bias force of cantilever spring 562

Figure 61A:
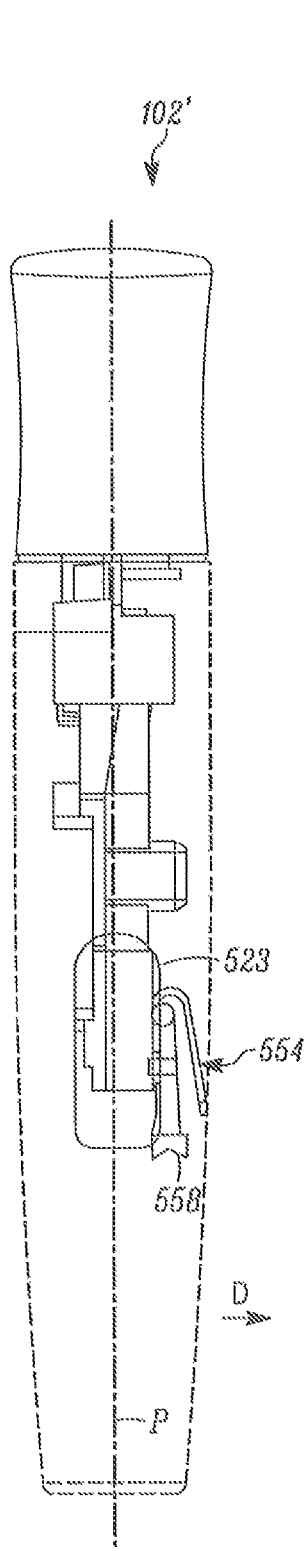
FIG. 61a is a top plan view (with the housing in phantom lines to reveal internal mechanisms) of the lancing device as shown FIG. 60a, with the locking member in a disengagement position.
Figure 61B:
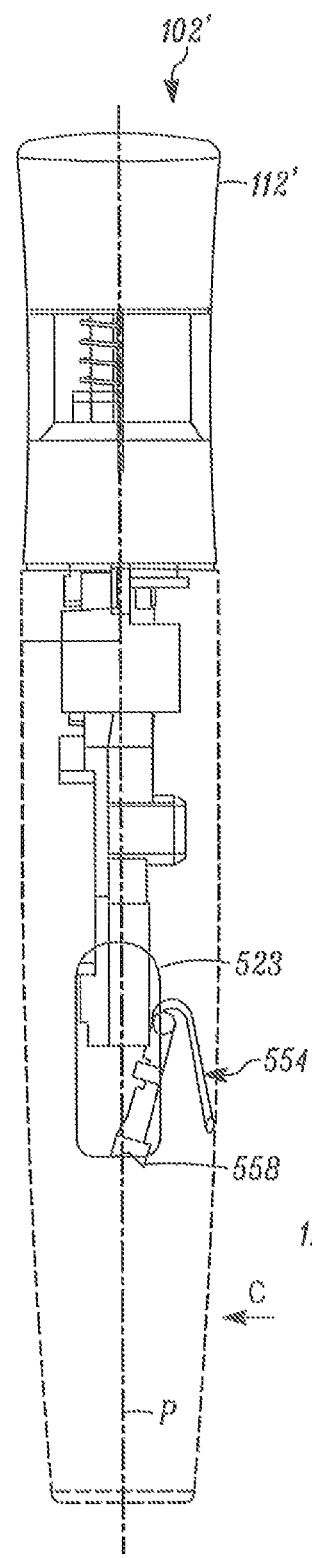
FIG. 61b is a top plan view (with the housing in phantom lines to reveal internal mechanisms) of the lancing device as shown in FIG. 60b, with the locking member in an engagement position.

Because of the slope of cam surface 576, upward movement of trigger button 523 will permit finger 570 to move (under the bias force of cantilever spring 562) in the direction of arrow "C" toward the path of insertion P (sees FIGS. 61b and 71). As finger 570 moves in the direction of arrow "C", interlock mechanism 554 rotates clockwise about cylinder 560 (when viewed from above), thus swinging blocking member 558 into an engagement position where it blocks the path of insertion P of lancet 104 (see FIG. 61b).

Likewise, downward movement of trigger button 523 will force finger 570 to move in the direction of arrow "D" away from the path of insertion P (see FIG. 61a) of lancet 104. As finger 570 moves in the direction of arrow "D", finger 570 overcomes the bias force of cantilever spring 562 to drive interlock mechanism 554 to rotate counter-clockwise (when viewed from above) about cylinder 560, thus swinging blocking member 558 into an disengagement position where it does not block the path of insertion P (see FIG. 61a).

Figure 61C:
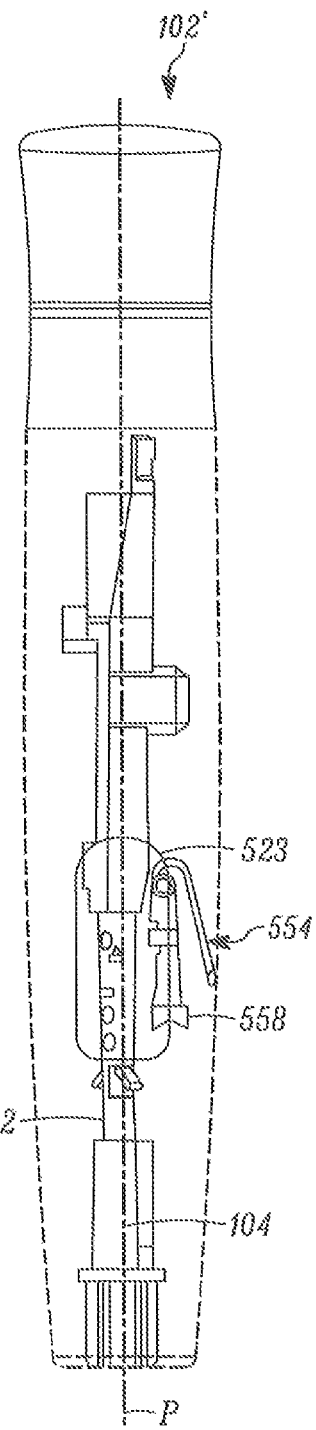
FIG. 61c is a top plan view (with the housing in phantom lines to reveal internal mechanisms) of the lancing device as shown FIG. 60b with a lancet inserted therein.
Figure 66:
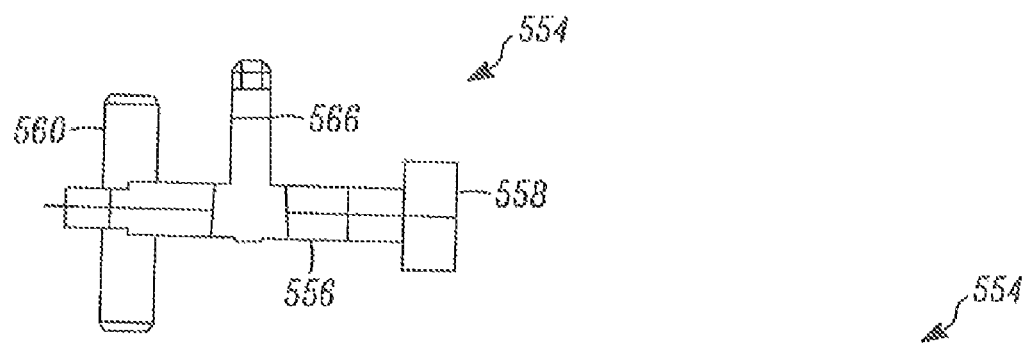
FIG. 66 is a right side view of the locking member of FIG. 62.
Figure 67:
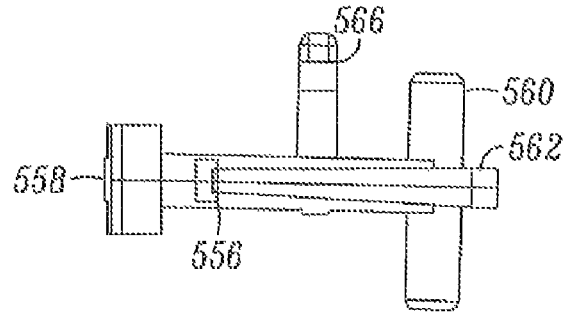
FIG. 67 is a left side view of the locking member of FIG. 62.
Figure 68:
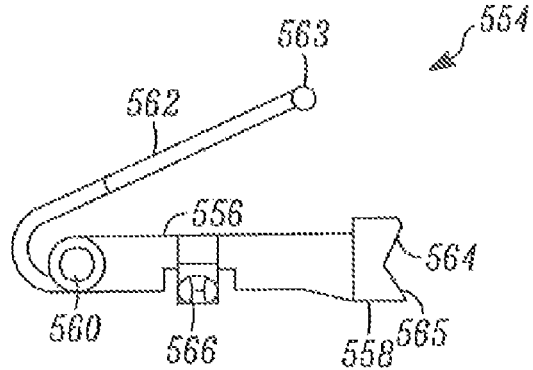
FIG. 68 is a top plan view of the locking member of FIG. 62.
Figure 69:
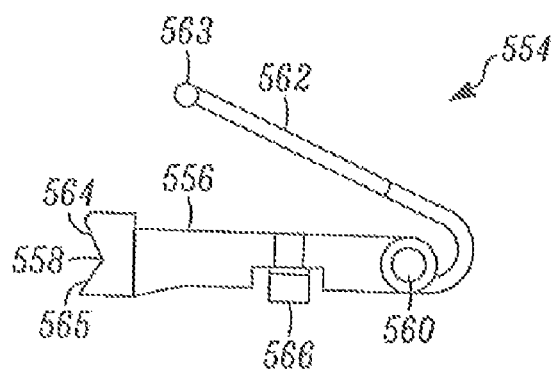
FIG. 69 is a bottom plan view of the locking member of FIG. 62.

Referring to FIGS. 61a through 61c, operation of trigger button 523 (shown in phantom lines) and interlock member 554 is illustrated. As shown in FIG. 61a, when lancing device 102' is uncocked, trigger button 523 is in a lowered elevation, forcing rotation of interlocking member 554 to the disengagement position. The user may insert lancet 104 into lancing device. As shown in FIG. 61b, when lancing device is cocked, such as by pulling cocking handle 112', trigger button 523 is in an elevated position, forcing rotation of interlocking member 554 to the engagement position where blocking member 558 obstructs the path of insertion P for inserting a lancet 104. When interlocking member 554 is in the engagement position, the user cannot fully insert lancet 104 into lancing device 102'.

As shown in FIG. 61c, if lancet 104 is inserted into lancing device 102' when lancing device is uncocked, and then subsequently lancet device is cocked, the resulting elevation of trigger button 523 would permit interlock member 554 to swing into its engagement position blocking path of insertion P of lancet 104. However, with lancet 104 already inserted (as shown in FIG. 61c), blocking member 558 simply abuts the side of lancet body 122.

It will be appreciated that the lancet interlock detailed above may be any other suitable interlock means, including for example slidable locking means or push tab locking means. It will be further appreciated that the movement of interlock member 554 may be actuated by other suitable arrangement and references to such arrangements are not limited to trigger button 523. For example, lancet carrier 208 can be coupled by cam action to interlock member 554 to urge interlock member 554 out of path of insertion P when lancet carrier 208 is moved out of its cocked position.

Carriage Assembly

Figure 72:
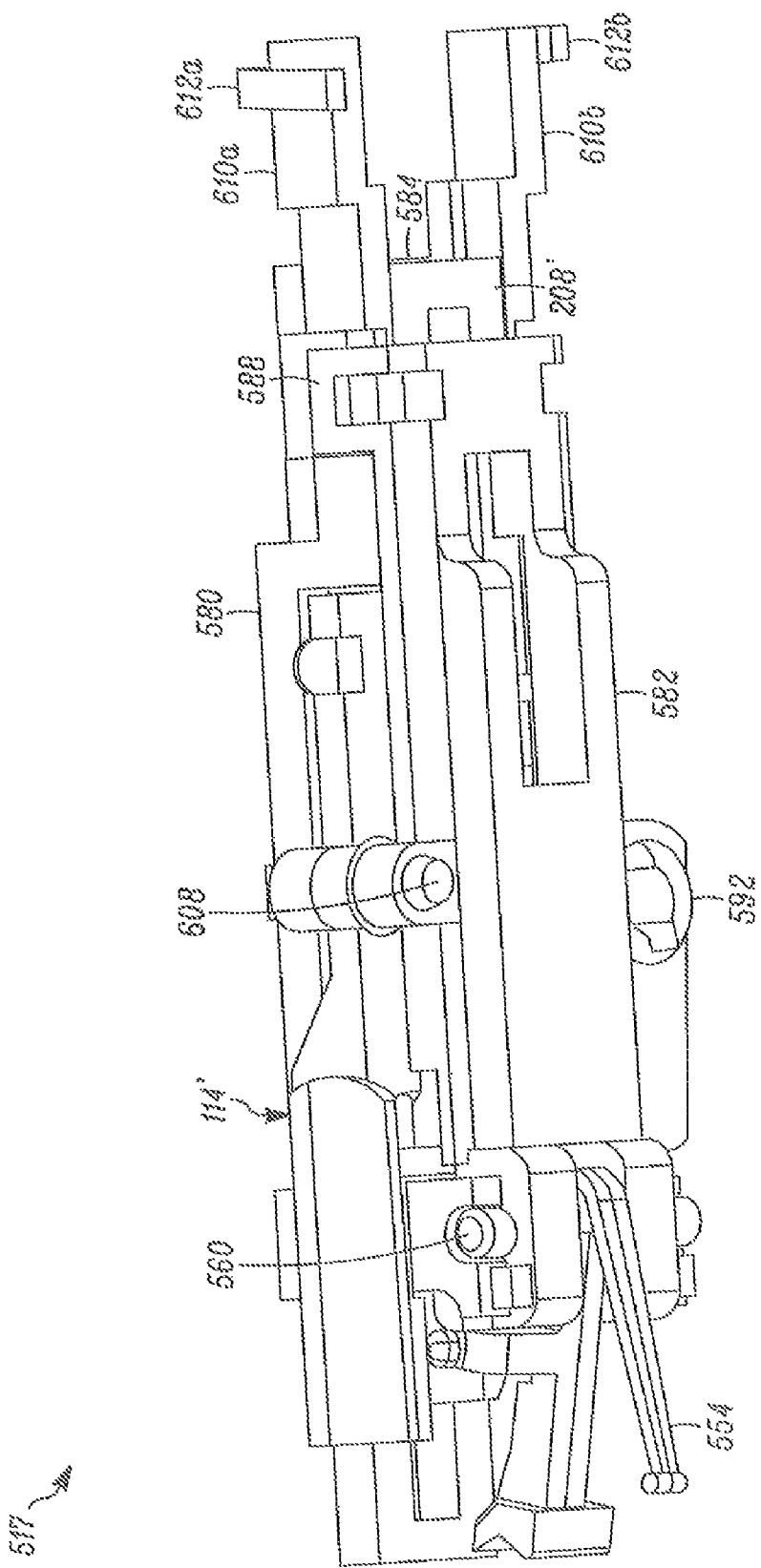
FIG. 72 is a perspective view of a carriage assembly of the lancing device of FIG. 51.
Figure 73:
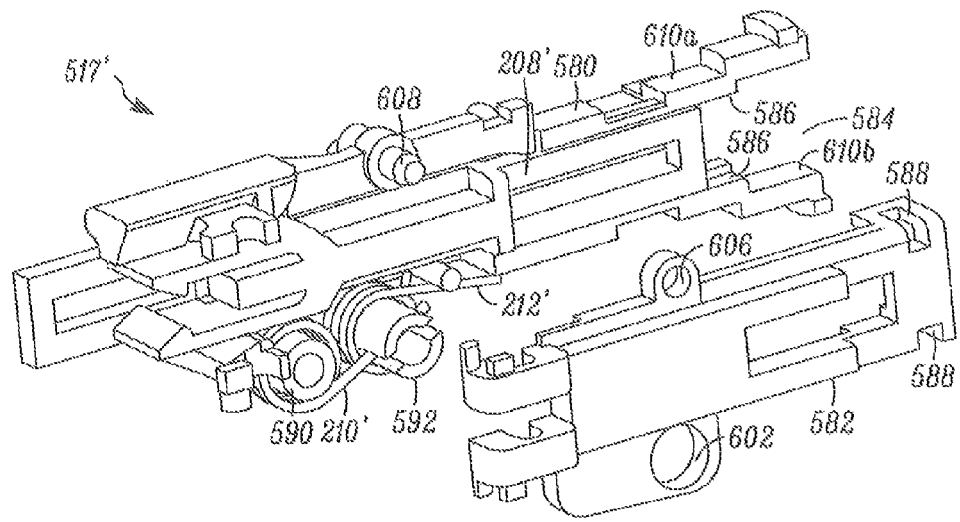
FIG. 73 is a partial exploded view of the carriage assembly of FIG. 72.
Figure 74:
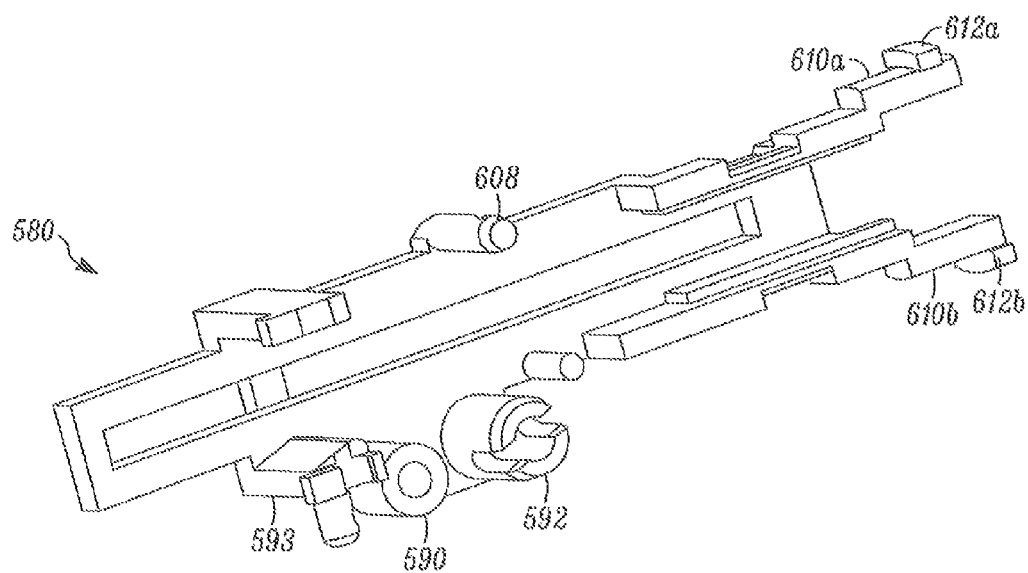
FIG. 74 is a front perspective view of a carriage in the carriage assembly of FIG. 72.
Figure 75:
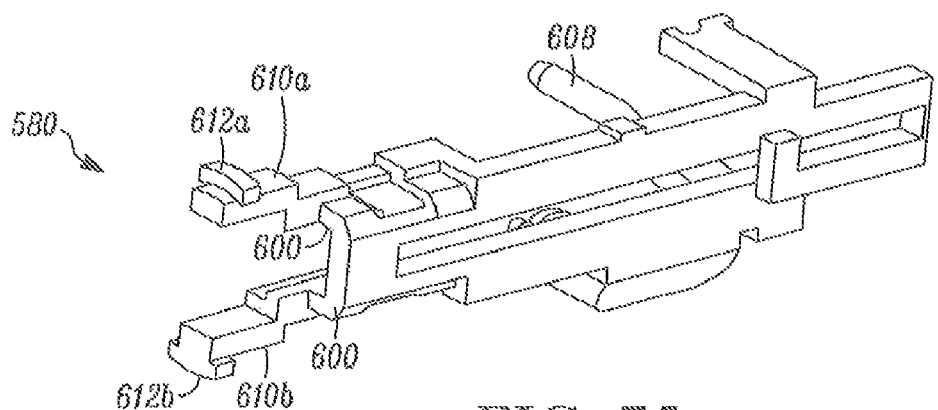
FIG. 75 is a rear perspective view of the carriage in the carriage assembly of FIG. 72.
Figure 77:
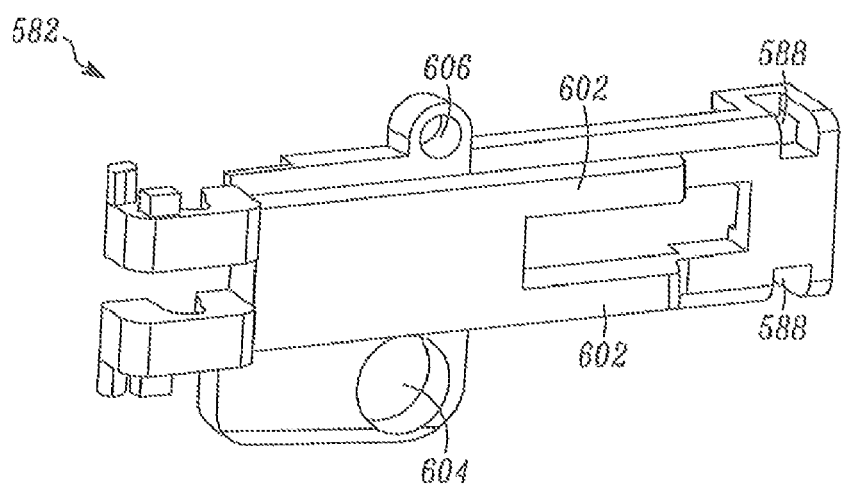
FIG. 77 is a front perspective view of a carriage cover of the carriage assembly of FIG. 72.

Referring to FIGS. 51 and 72, the structure and operation of carriage assembly 517 is described. Carriage assembly includes a carriage 580 and a carriage cover 582 suitably connected together to define therebetween a chamber 584 in which lancet carrier 208' is captured as seen in FIG. 73. Opposing top and bottom portions of lancet carrier 208' engages planar guide surfaces 586 of carriage 580 to permit lancet carrier 208' to slide axially within carriage assembly 517, as seen in FIG. 73. FIGS. 74 and 75 show carriage 580 in more detail. FIG. 77 shows carriage cover 582 in more detail. Carriage 580 and carriage cover 582 can be connected in any suitable manner, such as by snaps 588 on carriage cover 582. Adhesive, screws or other suitable fasteners may also be used.

As seen in FIGS. 72 and 73, carriage 580 includes a boss 590 on which drive spring 210' is mounted and a boss 592 on which drive spring 212' is mounted. Springs 210' and 212' engage lancet carrier 208' to move lancet carrier 208' to and away from piercing aperture in the same manner as describe above with respect to springs 210 and 212 and lancet 208. When a user pulls cocking handle 112', rod 314' draws back cocking hook 316' which engages lancet carrier 208' to pull lancet carrier toward the rear of housing 106' and thus tensioning drive spring 210'. When trigger assembly 515 is actuated, lancet carrier 208' is released from this tensioned or cocked position and is propelled forward to drive lancet 104 forward toward the piercing aperture 110' and thus penetrates the user's skin. As lancet carrier 208' moves forward in a piercing action, it engages and tensions return spring 212', which then impels lancet carrier 208' toward the rear of housing 106', thus retracting lancet 104 from the user's skin. The operations of springs 210' and 212' and the lancet carrier 208' and cocking handle 112' are substantially the same as described above with respect to springs 210 and 212 and lancet carrier 208 and cocking handle 112.

When lancet carrier 208' is fired, its forward motion is limited by a fixed projection such as a stop 593 located on carriage 580. Projection or stop 593 is fixed and is not aligned with or otherwise moved relative to lancet carrier 208'. Thus, in each cycle of cocking and firing, the length of travel of lancet carrier 208' can be the same. The stop 593 can be located and positioned in any suitable manner such as the top, bottom, front or rear of carriage assembly 517. Note that the position of projection stop 593 is fixed and is not moved or aligned relative to lancet carrier 208'

Figure 76:
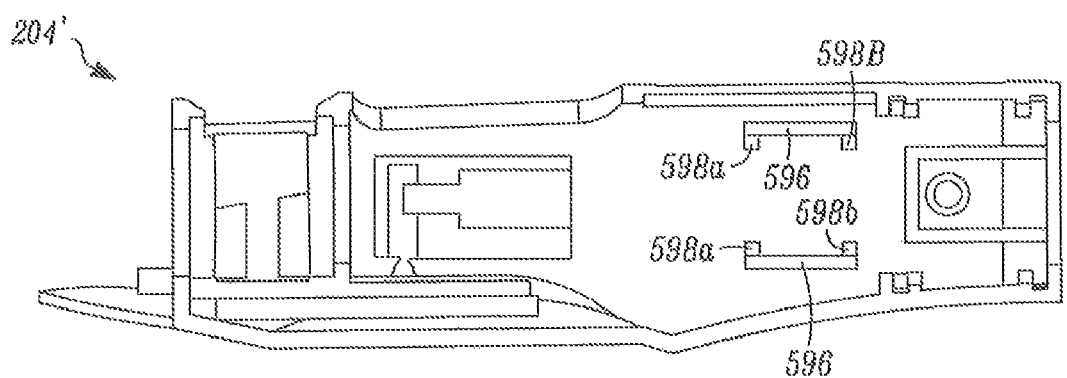
FIG. 76 is a side elevation of the right half portion of the housing shown in FIG. 51.

Carriage assembly 517 is slidably disposed with housing 106', which includes a pair of guide tracks 596 on at least the right half housing portion 204' as shown in FIG. 76. Each of tracks 596 includes stops 598 *a*, 598*b* at its opposing ends. Corresponding guide tracks (not shown) may be provided on left half housing portion 206' as well. Projections 600 extending from carriage 580 (see FIG. 75) engage tracks 596 and permit sliding axial movement of carriage assembly 517 defined by the distance between stops 598*a*, 598*b*. Carriage cover 582 includes guide surfaces 602 that engage corresponding structure (not shown) in the interior wall of left half housing portion 206' to prevent movement of carriage assembly 517 other than in an axial direction within housing 106'. Carriage cover 582 also includes an aperture 604 to revive boss 592 of carriage 580 and an aperture 606 to receive a boss 608 projecting from carriage 580. Bosses 592 and 608 align and couple carriage 580 and carriage cover 582.

Figure 78A:
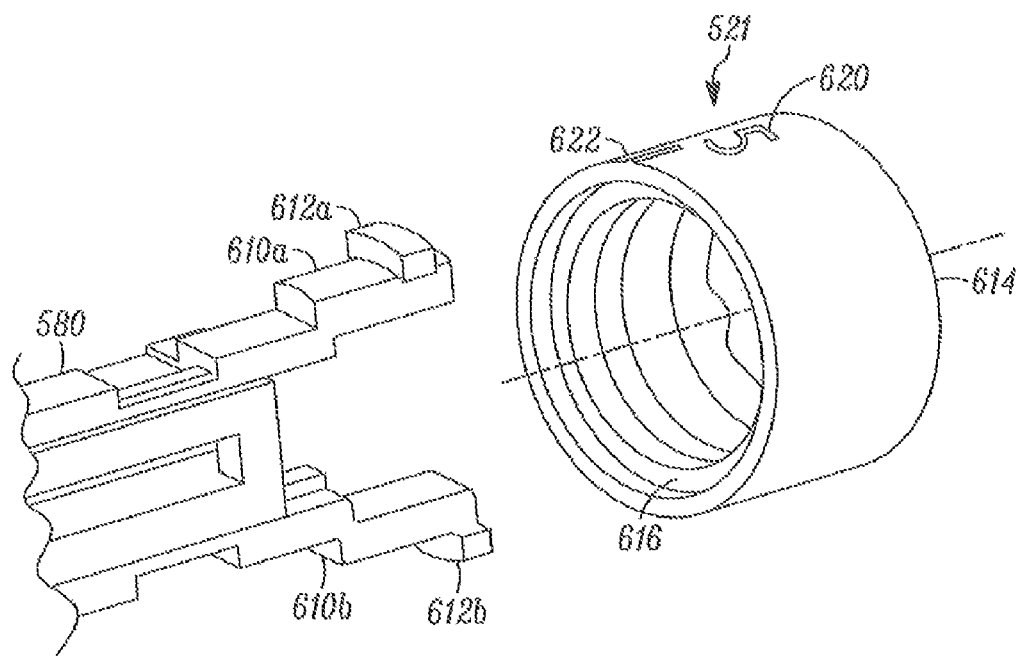
FIG. 78A is an enlarged perspective view of a depth adjuster of the lancing device shown in FIG. 51, illustrating its interaction with the carriage assembly of FIG. 72.

Referring to FIG. 74, the rear end of carriage 580 includes upper and lower members 610*a* and 610*b*, respectively. Fingers 612*a* and 612*b* extend in radially opposite directions from each of upper and lower members 610*a* and 610*b*, respectively. As explained below, fingers 612*a*, 612*b* engage depth adjuster 521 as shown in FIG. 78A.

Figure 78B:
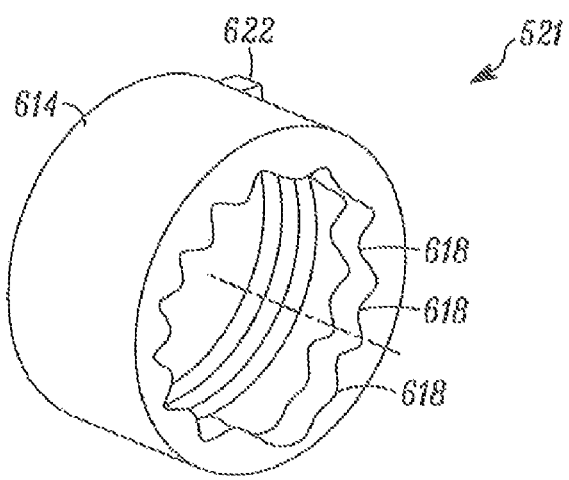
FIG. 78B is a rear perspective view of the depth adjuster of FIG. 78A.

The function of depth adjuster 521 is to permit users to adjust the penetration depth of lancet 104 when lancing device 102' is fired. Referring to FIGS. 78A and 78B, depth adjuster 521 includes a depth adjustment ring 614 mounted on housing 106' for rotation about the axis of housing 106'. The forward interior portion of depth adjustment ring 614 has threads 616 and the rearward interior portion depth adjustment ring 614 has circumferentially arranged detents 618. A protrusion (not shown) on housing 106', engages detents 618 to provide discrete settings for depth adjustment ring 614 as it rotates about the axis of housing 106'.

Carriage assembly 517 is positioned within housing 106' so that fingers 612*a*, 612*b* extend into the interior of depth adjustment ring 614 and engage threads 616. When a user rotates depth adjustment ring 614, threads 616 acts on fingers 612*a*, 612*b* to drive carriage assembly 517 in sliding axial motion to and from piercing aperture 110'. Note that the path of travel of lancet carrier 208' during firing of lancing device 102' does not vary relative to carriage assembly 517. Thus, when depth adjustment ring 614 is rotated in a first direction, carriage assembly 517 is moved closer to piercing aperture 110', the entire lancet carrier 208' and its travel path is also moved closer to piercing aperture 110'. As a consequence, sharp tip 120 of lancet 104 extends farther from piercing aperture 110' when lancing device is fired, and thus penetrates more deeply into the user's skin. Similarly, when depth adjustment ring 614 is rotated in a second direction, carriage assembly 517 is moved away from piercing aperture 110', so that the entire lancet carrier 208' is moved away from piercing aperture 210. As a consequence, sharp tip 120 of lancet carrier 104 extends a shorter distance from piercing aperture 110' when lancing device 102' is fired, and thus penetrates less deeply into the user's skin.

It will be appreciated that manipulation of depth adjustment ring 614 permits the user to adjust the ultimate penetration depth of lancet 104 when lancing device 102' is fired. The exterior of depth adjustment ring 614 is accessible to users for rotation and can include indicia 620 and a knob 622 to facilitate manipulation by the user. As depth adjustment ring 614 rotates, indicia 620 are visible to the user to indicate the resulting depth setting.

Figure 79A:
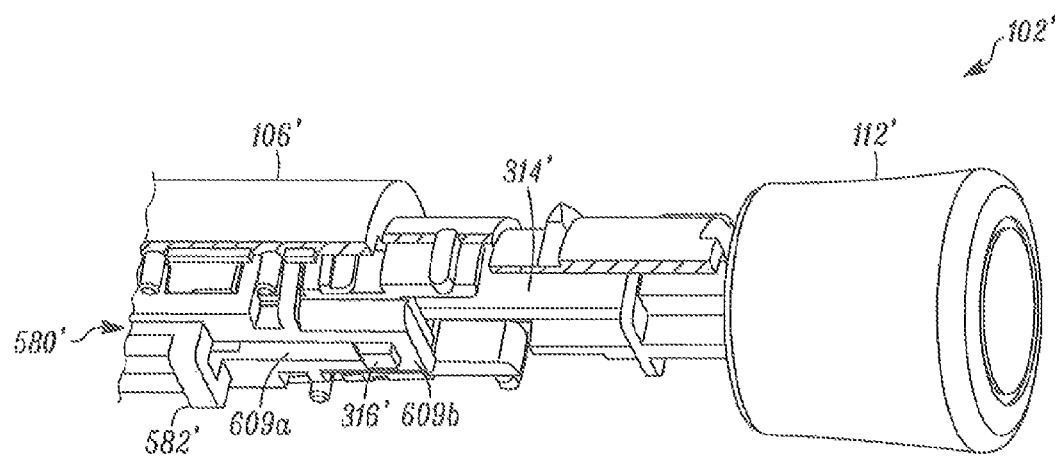
FIG. 79A is a partial perspective view of an alternative embodiment of the carriage assembly of FIG. 72, showing the engagement of a cocking assembly with the carriage assembly.
Figure 79B:
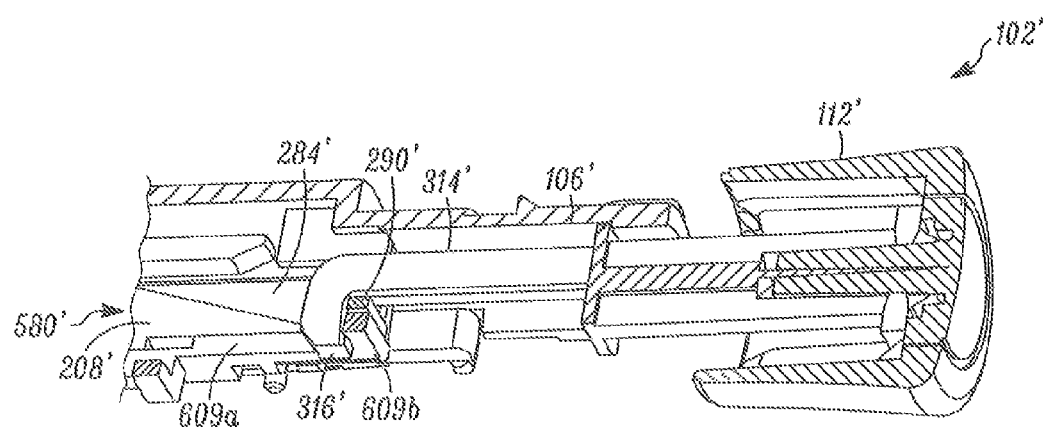
FIG. 79B is a sectional view of the carriage assembly as shown in FIG. 79A.

Referring to FIGS. 79A and 79B, an alternative embodiment in the form of carriage 580' is illustrated. This embodiment is substantially identical to the embodiment of FIG. 72. An elongated horizontal slot 284' is provided in rearward half portion of lancet carrier 208'. Slot 284 defines a rear wall 290'. As described above, when a user pulls cocking handle 112', rod 314' draws back cocking hook 316' which engages rear wall 290' of lancet carrier 208' to move lancet carrier 208' rearward. In this embodiment, however, carriage cover 582' includes an elongated slot 609*a* to accommodate the distal tip of cocking hook 316'. A stop 609*b* at the rearward end of slot 609*a* limits the distance that cocking rod 314' (and therefore lancet carrier 208') can be pulled rearward. This is advantageous for example, when receiver 170 is mounted to carriage assembly 517'. In that case, if lancet 104 is inserted into lancing device 102' with removable tab 124 still attached and then pulls cocking handle, there is a possibility of retracting lancet carrier 208' sufficiently rearward so that removable tab 124 engages the front end of receiver 170. In that case, the engagement of tab 124 with receiver 170 can prevent further rearward movement of lancet 104, resulting in a disengagement of lancet 104 from lancet carrier 208' as cocking handle 112' draws lancet carrier 208' further back. If the stop 609*b* is placed on carriage assembly 517', the distance between stop 609*b* and receiver 170 is fixed, and therefore it can be assured that cocking handle 112' will not draw back lancet carrier 208' so far as to disengage lancet 104. If however, a cocking handle stop such as stop 609*b* were placed on the housing it would need to be sufficiently rearward to allow cocking through the full range of positions of carriage assembly 517'. This rearward position of a cocking handle stop fixed to housing 106' would be farther from the front end of receiver 170 as carriage assembly 517' was moved forward by depth adjustment ring 614 so that the movement rearward of lancet carrier 208' by cocking handle 112' would potentially disengage lancet 104 from lancet carrier 208'

Figure 80:
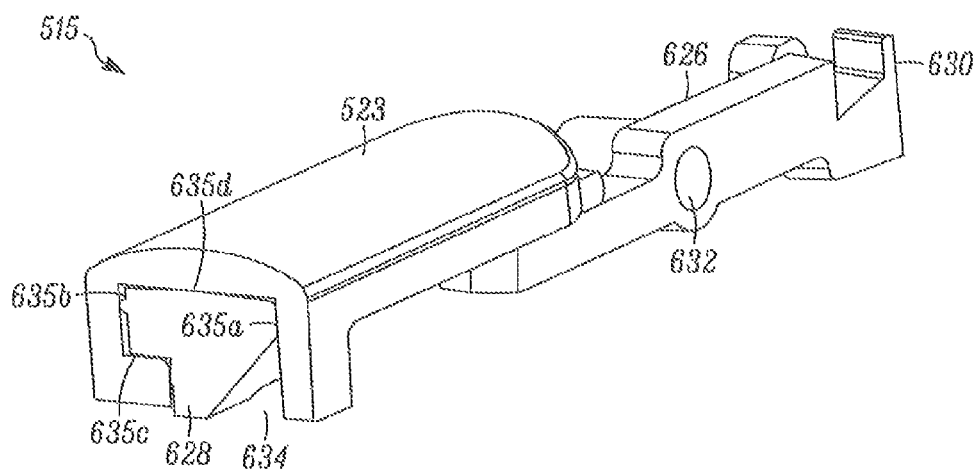
FIG. 80 is a front perspective view of the trigger assembly of the lancing device of FIG. 51.
Figure 81:
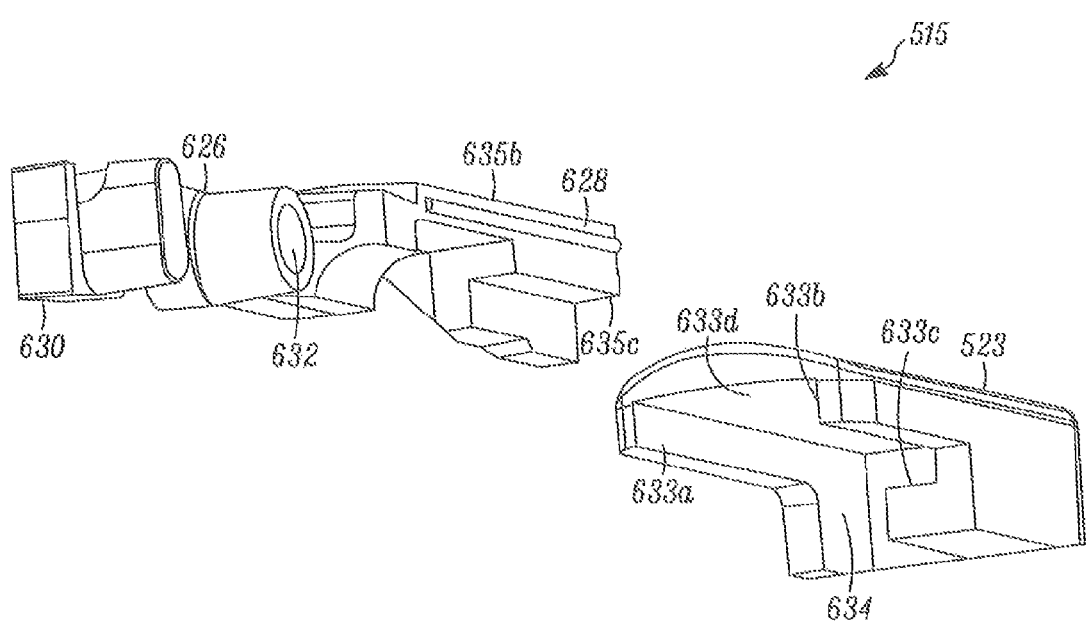
FIG. 81 is an exploded, rearward perspective view of the trigger assembly of FIG. 80.

To accommodate movement of carriage assembly 517, a trigger assembly 515 is provided as shown in FIGS. 51, 80 and 81. Trigger assembly 515 operates in substantially the same manner as trigger 114. Its functions can include holding lancet carrier 208' in, and upon actuation by a user releasing lancet carrier 208' from, its cocked position so that drive spring 210' can propel lancet carrier 208' forward.

Trigger assembly 515 includes trigger button 523 which is captured by a trigger aperture 203' in housing 106' and a trigger arm 626 having a front end 628 and a rear end 630 and laterally-oriented mounting aperture 632 there between. Trigger arm 626 is mounted by aperture 632 to boss 608 extending from carriage 580 so that trigger arm 626 can pivot about boss 608 in see-saw fashion. Alternatively, aperture 632 can be located near end of trigger arm 626. Note that trigger button 523 is captured by trigger button aperture 203' so that it cannot move in a longitudinal direction relative to housing 106' as carriage assembly 517 is moved by depth adjustment ring 614. In contrast, trigger arm 626 is mounted to boss 608 of carriage 580, so that when carriage assembly 517 moves axially within housing 106', trigger arm 626 is also moved axially with carriage assembly 517.

To accommodate the axial movement of trigger arm 626, front end 628 of trigger arm 626 is received in sliding engagement by a recess 634 in trigger button 523, so that the trigger arm 626 can be extended relative to trigger button 523 by varying lengths as carriage assembly 517 slides within housing 106'. Recess 634 includes interior guide surfaces 633*a*-

633d which corresponds in mating engagement to guide surfaces 635a-635d, respectively on trigger arm 626, as best seen in FIG. 80. The engagement of guide surfaces 633a-d and 635a-d allows trigger arm to slide axially within trigger button 523, thus allowing trigger arm 626 to be extended by varying lengths when carriage assembly 517 slides within housing 106'. Other mechanisms such as a telescoping arm structure could also be employed to achieve this purpose.

A clip spring 636 or other suitable biasing mechanism is coupled to housing 106' and urges the rear end 630 of trigger arm 626 downward and front end 628 upward, so that trigger button 523 extends through trigger aperture 203'. In this position, a latch 638 that depends from rear end 630 of trigger arm 626 can engage lancet carrier 208' to hold it in a cocked position. When a user presses trigger button 523, the bias of clip spring 636 is overcome, and trigger arm 626 pivots so that the front end 628 moves downward and the rear end 630 moves up, effectively firing lancing device 102' by lifting latch 638 up off of lancet carrier 208' so that drive spring 210' can propel lancet carrier 208' toward piercing aperture 110'.

Because trigger arm 626 moves with carriage assembly 517, the relative axial position of trigger arm 626 and the front end of lancet carrier 208' can be fixed. When lancet 104 is inserted into lancing device 102', lancet 104 engages lancet carrier 208' to both insert the rear end of lancet 104 into lancet carrier 208' and push lancet carrier rearward into a cocked position, as described above. Trigger arm 626 can be positioned so that trigger assembly 515 goes into a cocked configuration at or just after the time when lancet 104 has been inserted into lancet carrier 208'. Thus, the cocking of trigger assembly 515 (and the attended visual indication of trigger button 523 extending through housing 106') occurs after a user has successfully inserted lancet 104 into lancet carrier 208'. If the cocking of trigger assembly 515 occurs earlier, the user may stop inserting lancet 104 on the mistaken perception that the lancet was successfully inserted. If the position of trigger arm 626 did not move with carriage assembly, then cocking of trigger assembly 515 could occur at different times relative to the insertion of lancet 104 into lancet carrier 208' depending on the axial position of carriage assembly 517.

Alternative Embodiment of Lancet

Figure 82:
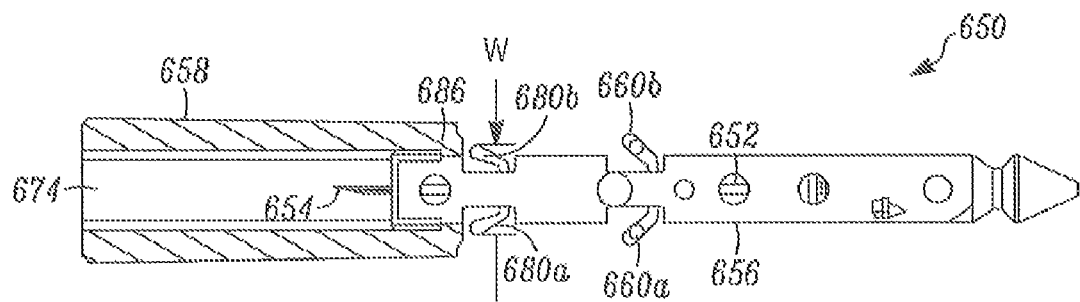
FIG. 82 is a lancet in accordance with an alternative embodiment of the invention, showing the lancet sleeve (in sectional) in its fully extended and locked position.
Figure 83:
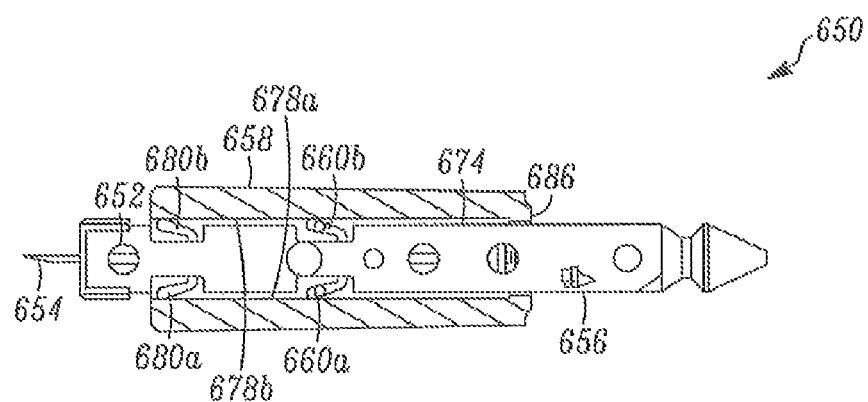
FIG. 83 is side elevation of showing the lancet sleeve in its retracted position.
Figure 84:
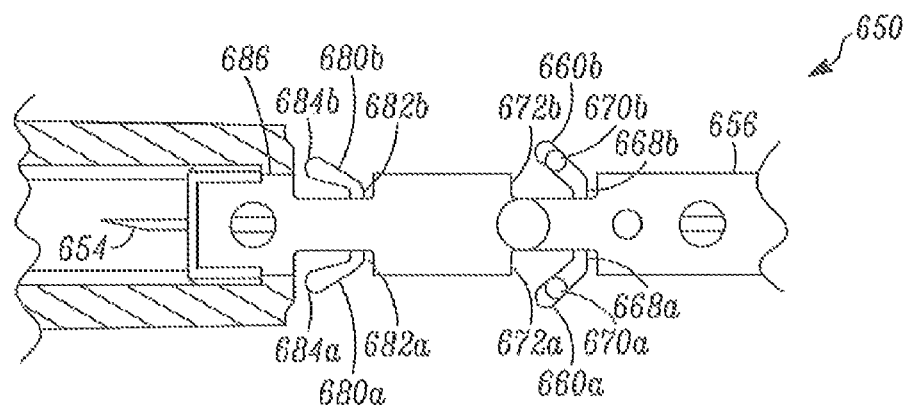
FIG. 84 is an enlarged side elevation of the lancet of FIG. 82.

Referring to FIGS. 82-84, an alternative embodiment of lancet 104 is illustrated in the form of lancet 650. Lancet 650 includes needle 652 whose length (excluding a sharp tip 654) is encased in an elongated lancet body 656. A sleeve 658 slides axially over a portion of the lancet body 656 between forward position (as shown in FIG. 82), in which it protectively surrounds the sharp tip 654 of needle 652, and a rearward position (as shown in FIG. 83) in which sharp tip 654 protrudes beyond the front end of sleeve 658.

Referring to FIG. 84, lancet body 656 includes a pair of locking members or wings 660a, 660b extending from left and right lateral surfaces of lancet body 656, respectively, near the mid-section of lancet body 656. Each of wings 660a, 660b has a short, stiff base portion 668a, 668b extending radially out from lancet body 656 and a planar flexion member 670a, 670b having a wingtip extending in generally forward direction but at a 45° angle away from the major axis of the lancet body 656 in the extended configuration. Wings 660a, 660b may be molded as part of lancet body 656.

Wings 660a, 660b can flap into retracted configuration by folding planar flexion members 670a, 670b from their extended position shown in FIG. 84 to a retracted position in which each flexion member 670a, 670b is folded forward so that each flexion member 670a, 670b is substantially disposed within its corresponding one of wing wells 672a, 672b, as shown in FIG. 83. Planar flexion members 670a, 670b are flexible and resilient in that they can be folded into wing wells 672a, 672b under the influence of a lateral force, but will return to their outward extending position when that force is removed.

Sleeve 658 is generally tubular with an elongated inner chamber 674 having a cylindrical contour to receive lancet body 656. The cylindrical contour of inner chamber 674 is modified by the inclusion of wing engagement surfaces 678a, 678b, which are a pair of wide, shallow lateral grooves on opposing lateral sides of sleeve interior chamber 674 that extend the length of sleeve 658. Although sleeve 658 is tubular, sleeve 658 can be made with different sectional shapes or slots (to reduce the material used to manufacture sleeve 658). In additional embodiments, the sleeve 658 has a cross section that is one of polygonal, circular and ovular, as shown in FIGS. 93a-c.

When wings 660a, 660b are in extended configuration (as shown in FIG. 82), their wingtips span a distance greater than the diameter of inner chamber 674. If sleeve 658 moves rearward relative to lancet body 656 from its protective extended position, wings 660a, 660b, if extended, will engage the rear end of lancet sleeve 658, blocking further rearward movement of sleeve 658 and in effect locking sleeve 658 in its protective extended position.

However, when wings 660a, 660b are in their retracted configuration (that is, folded into wing wells 672a, 672b as shown in FIG. 83), they do not extend beyond the diameter of inner chamber 674, so that sleeve 658 can slide axially over lancet body 656 without interruption. As sleeve 658 slides over wings 660a, 660b, each of the wings (now folded into wing wells 672a, 672b) brushes along the longitudinal extent of elongated guide surfaces, or wing engagement surfaces 678a, 678b, as shown in FIG. 83.

While wings 660a, 660b are made of a deformable, resilient material, it is possible in rare cases that if wings 660a, 660b remain in a folded position for a long time, they may lose resiliency and therefore not return to their extended position when lancet 650 is ejected from its lancing device 102 and sleeve 658 is pushed to its extended protected position. This may occur, for example, if lancet 104 is loaded into lancing device 102 and is then left by the user without further use for a long period of time, particularly if lancing device 102 is subject to high temperature. Alternatively, if lancet 650 is used repeatedly (inserted, ejected from and re-inserted into lancing device 102), wings 660a, 660b may lose resiliency and therefore not return to their extended position when lancet 650 is ejected from lancing device 102.

If wings 660a, 660b did not return to their extended position, then upon ejection it is possible that sleeve 658 would not be locked into its extended position. To ensure that this does not happen, the alternative embodiment of FIGS. 82 through 84 includes a second pair of locking members or wings 680a, 680b formed in left and right lateral surfaces of lancet body 656 respectively, near the forward end of lancet body 656 and axially spaced from the first set of wings 660a, 660b. Wings 680a, 680b are similar in structure to wings 660a, 660b, but are of a material that is less flexible than the material of wings 660a, 660b. Each of wings 680a, 680b has a short, stiff base portion 682a, 682b (see FIG. 84) extending radially out from lancet body 656 and a planar flexion member 684a, 684b extending from the base portion 682a, 682b in generally forward direction but at an acute angle away from the major axis of the lance body 656. Second pair of wings 680a, 680b may be molded as part of lancet body 656.

Planar flexion member 684a, 684b are sized and configured so that the wing span of wings 680a, 680b is equal to or less than the diameter of the interior chamber 674 of sleeve 658, with the sleeve 658 having a diameter of less than 5 mm. During use and operation of lancet 650, second pair of wings 680a, 680b may be within the interior chamber 674 of sleeve 658. However, as shown in FIG. 82, since the wingspan W of wings 680a, 680b is equal or less than the diameter of chamber 674, they remain in a relatively relaxed state (as compared to wings 660a, 660b) when placed into chamber 674 and are subject to little or no deformation. As a result, wings 680a, 680b retain their resiliency even when lancet 650 remains in lancing device 102 for a long time.

When lancet 650 is ejected from lancing device 102 (as described above), sleeve 658 is pushed forward to its extended position where it surrounds needle sharp 654. As sleeve 658 slides forward relative to lancet body 656, second pair of wings 680a, 680b pass through a neck 686 in the rear end of sleeve 658. The diameter of neck 686 is less than the diameter of chamber 674 and also less than the wingspan of wings 680a, 680b when in an extended configuration. Wings 680a, 680b are configured so that when the rear-facing surface of planar flexion members 684a, 684b engages neck 686, it is pushed toward the longitudinal axis of lancet body 656, in effect folding wings 680a, 680b to permit their passage through neck 686.

Once sleeve 658 has moved fully forward, so that wings 680a, 680b have passed through neck 686, then wings 680a, 680b return to their relaxed position, as shown in FIG. 82. Because the diameter of neck 686 is less than the span of wings 680a, 680b, the tips of wings 680a, 680b engage the rear end of sleeve 658, locking it in its extended position.

Because the flexion of wings 680a, 680b occurs for a short interval upon ejection of lancet 650, there is less chance that wings 680a, 680b will lose their resiliency and fail to extend to a wingspan sufficient to lock sleeve 658 into place. In the unlikely event that wings 660a, 660b were to fail, wings 680a, 680b would in all probability be operable to prevent sleeve 658 from sliding completely out of its extended forward position protecting needle sharp 654.

Note that one possible configuration to package lancet 650 is such that when it is initially manufactured, a frangible tab similar to frangible tab 124 (see FIG. 5) holds sleeve 658 in a position where it encloses second wing pair 680a, 680b but is forward of (and locked into position by) first wing pair 660a, 660b. In this manner, if the frangible tab is removed by a user before inserting lancet 650 into lancing device 102, wings 660a, 660b will prevent sleeve from moving out of an extended forward position in which it protects sharp 654.

A variety of structures may be used to perform the locking function. These other structures include, but are not limited to, pivoting members that pivot rather than fold into the wing wells, studs that extend out from the lancet body that can be pushed into a retracted position into a well in the lancet body, or barbs. For example, referring to FIGS. 85-87, an alternative embodiment in the form of a lancet 690 is shown having a pair of barbs 692a, 692b which, although having a different structure and orientation, perform the locking function as wings 680a, 680b.

Lancet 690 is similar in form and function to lancet 104. Lancet 690 includes a needle 694 (not shown) that is encased in elongated lancet body 698. A sleeve 700 slides axially over a portion of the lancet body 698 between an extended position in which it protectively surrounds the needle sharp, and a rearward position in which a portion of sharp protrudes beyond the front end of sleeve 700.

Lancet body 698 has a substantial cruciform cross section to define four elongated guide ribs 702a-d extending radially at ninety degree intervals.

Sleeve 700 includes a rear end having a cruciform opening 704 to engage the four guide ribs of lancet body 702a-d so that sleeve 700 can slide axially over lancet body 698.

Extending from ribs 702a and 702b are wings 706a and 706b, respectively. Wings 706a, 706b function substantially as wings 660a, 660b described above. Wings 706a, 706b are configured as an inclined planar flexion member extending from and integral with each of ribs 702a and 702b, respectively.

Barbs 692a, 692b are aligned with ribs 702c and 702d, respectively. Barbs 692a, 692b have flexible portions 708a and 708b forming in a V-shaped configuration, with the point of the V facing rearward. The rearward ends of portions 708a, 708b define a width that is wider than the portions 710a and 710b of cruciform opening 704 that receives barbs 692a, 692b when sleeve 700 moves rearward relative to lancet body 698. However, the inter chamber of sleeve 700 is sized to accommodate barbs 692a, 692b without deformation.

When lancet 690 is initially manufactured, sleeve 700 can be positioned relative to lancet body 698 so that barbs 692a, 692b are within the interior chamber of sleeve 700, which includes opposing longitudinal engagement surfaces 712a and 712b (see FIGS. 86 and 87) sized and positioned to accommodated barbs 692a, 692b, thus permitting sleeve 700 to slide axially relative to lancet body 698. When lancet 690 is ejected from lancing device 102, for example, sleeve 700 is pushed forward until barbs 692a, 692b are forced through portions 710a and 710b of cruciform opening 704 in the rear of sleeve 700. Although the opening portions 710a, 710b are more narrow than barbs 692a, 692b, barbs 692a, 692b are configured so that when the rear-facing surface of each flexible portion 708a, 708b engages opening portions 710a, 710b, barbs 692a, 692b are squeezed to in effect pinch the barbs 692a, 692b and permit their passage through the opening portions 710a, 710b.

Figure 85:
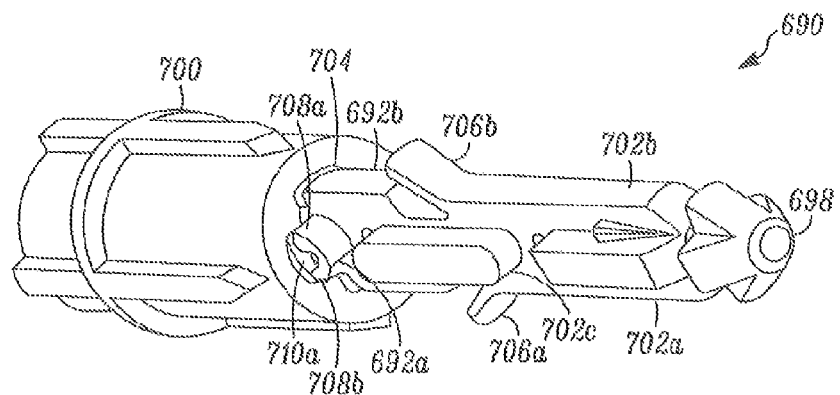
FIG. 85 is a perspective view of a lancet in accordance with another embodiment of the invention.
Figure 86:
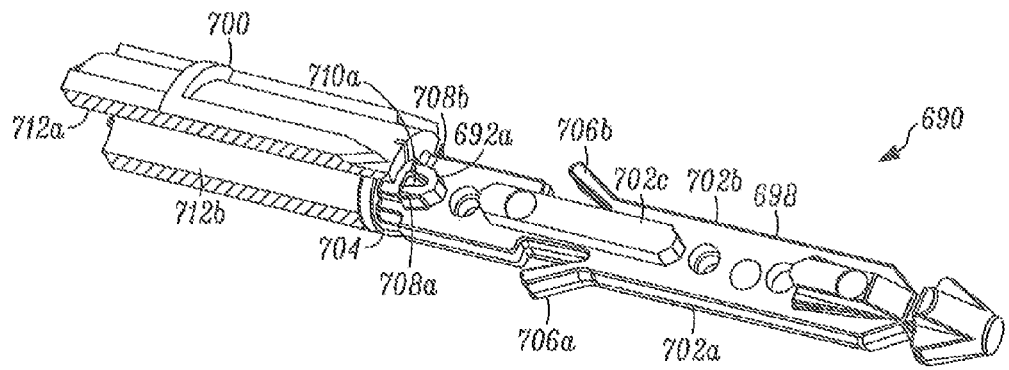
FIG. 86 is a rear perspective view of the lancet of FIG. 85, with a portion of its sleeve cut away to reveal its interior structure.
Figure 87:
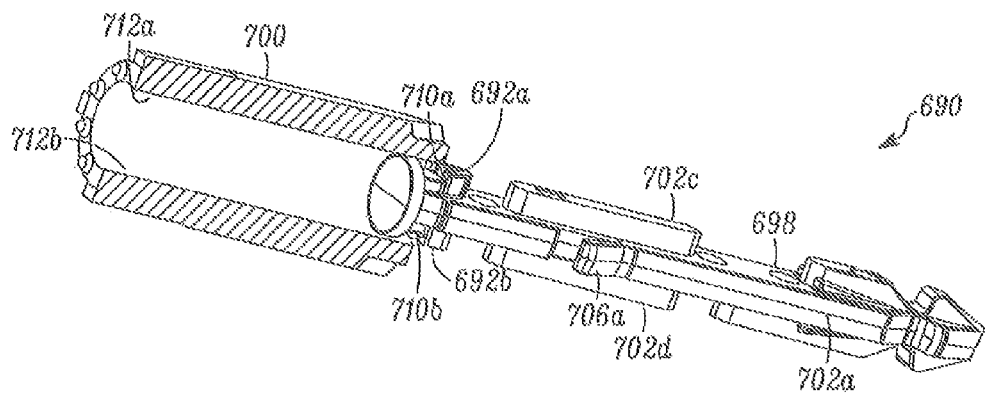
FIG. 87 is a front perspective view of the lancet of FIG. 85, with a portion of its sleeve cut away to reveal its interior structure.

Once sleeve 700 has moved fully forward, so that barbs 692a, 692b have passed through opening portions 710a, 710b, then flexible portions 708a, 708b return to their relaxed position, as shown in FIGS. 85 through 87. Because the width of opening portions 710a, b is less than the width of barbs, barbs engage the end of sleeve, locking it in its extended position.

Alternative Embodiment of Ejection Locking Member

Referring to FIGS. 88 through 92, an alternative embodiment of lancing device 102' is described in which an ejection locking member 750 is provided. Ejection locking member 750 performs a function similar to that of ejection locking member 524, described above, namely to prevent forward movement of lancet carrier 208' when lancet 104 is ejected from housing 106'. Ejection locking member 750 operates in conjunction with an ejection actuator 516' similar in construction and function to ejection actuator 516 described above.

Figure 88:
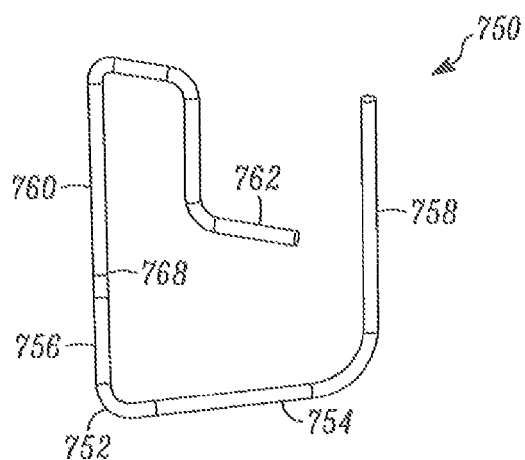
FIG. 88 is an ejection locking member in accordance with an alternative embodiment of the lancing device of FIG. 51.

Referring to FIG. 88, ejection locking member 750 is made of a wire-like metal (although plastic or other materials can be used) which is configured to define V-shaped blocking portion 752 formed by two elongated members 754 and 756 at approximately right angles to each other, each lying in a common horizontal plane. Extending vertically from the distal end of member 754 is an elongated guide arm 758. Extending vertically from the distal end of member 756 is an elongated anchor arm 760. Anchor arm 760 terminates in a Z-Shaped anchor portion 762. Ejection locking arm is mounted to a carriage 580.

Figure 89:
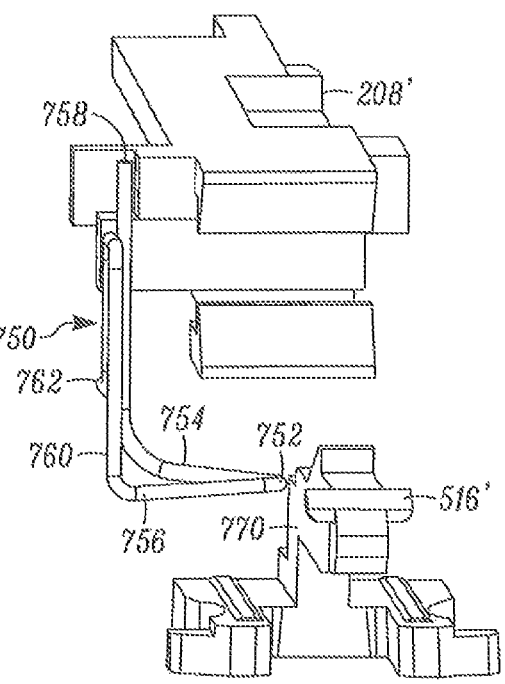
FIG. 89 is an isolated perspective view of the ejection locking member of FIG. 88 in relation to the lancet carrier and an ejection actuator.
Figure 90:
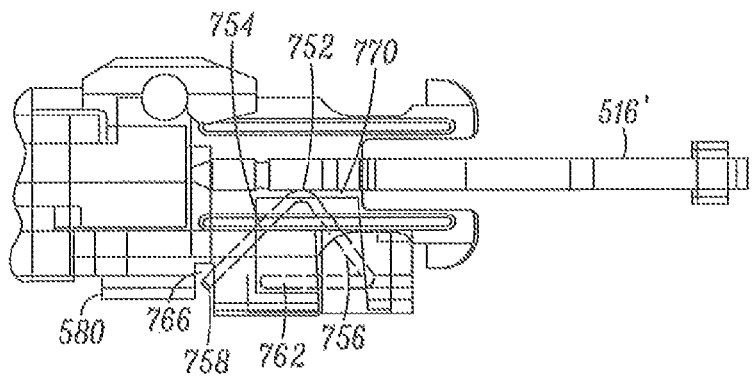
FIG. 90 is partial top plan view of the carriage assembly of FIG. 51 in which the ejection locking member of FIG. 88 has been installed.
Figure 91:
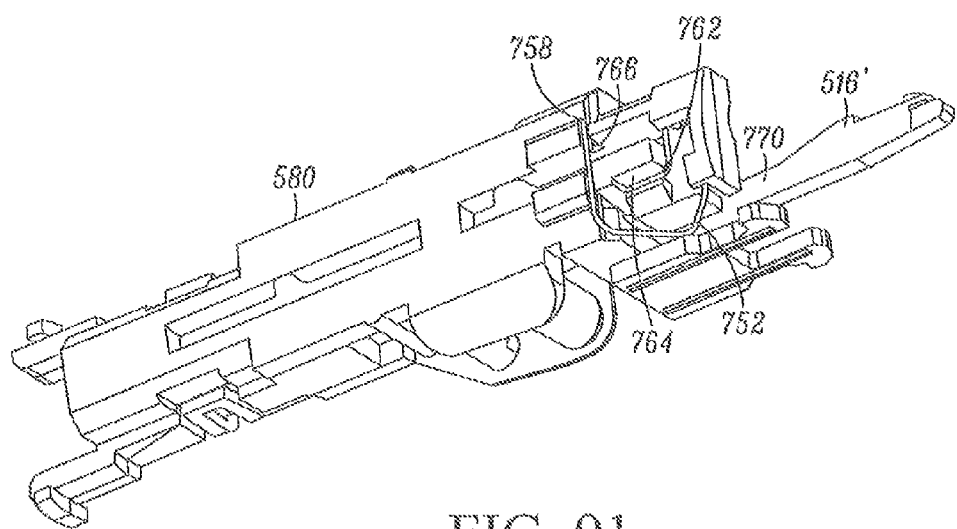
FIG. 91 is an isolated perspective view of the carriage assembly and ejection locking member of FIG. 90, showing the ejection locking member forced into its open position by the ejection actuator of FIG. 89.
Figure 92:
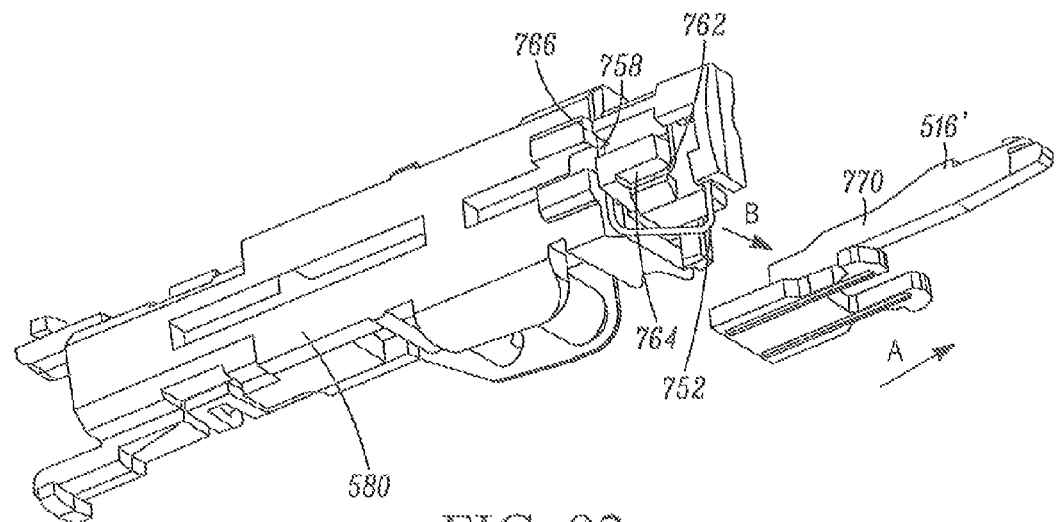
FIG. 92 is an isolated perspective view of the carriage assembly and ejection locking member of FIG. 90, showing the ejection locking member in its closed position after the ejection actuator of FIG. 89 has been slid forward.

Referring to FIGS. 89 through 92, the interrelationship of ejection locking member 750, carriage 580 and lancet carrier 208' and ejection actuator 516' is shown. Ejection locking member 750 is installed on carriage 580 so that anchor portion 762 is secured by a receiving notch 764 on carriage 580 (seen in FIGS. 91 and 92) and guide arm 758 is slidably engaged by a vertical notch 766 in carriage 580. In this configuration, blocking portion 752 is interposed in the path of lancet carrier 208', so that the forward movement of lancet carrier 208' along its longitudinal axis is blocked, as shown in FIGS. 89 and 92. Note that for clarity carriage 580 is not illustrated in FIG. 89.

Referring to FIGS. 90 and 91, during the loading, cocking and firing operations of lancing device 102', ejection actuator 516' is in its rearward neutral position, where an engagement surface 768 on the right-hand side of ejection actuator 516' engages blocking portion 752 to push it out of the path of lancet carrier 208'. Notch 766 provides clearance to allow movement of guide arm 758 when this movement occurs. Note, however, that in this configuration, a torsion force is imposed on ejection locking member 750 at point 768 (FIG. 88), as member 756 rotates slightly about the longitudinal axis of anchor arm 760.

When lancing operations are completed, the user will actuate ejection actuator 516' as described above to remove lancet 104 (not shown in FIG. 88 through 92), resulting in the forward movement of ejection actuator 516' as shown in FIG. 92. As ejection actuator 516' moves forward in the direction of arrow A, engagement surface 770 no longer engages blocking portion 752. The torsion force imposed at point 768 causes member 756 to rotate in spring-like fashion to its neutral, untensioned state, thus moving blocking portion 752 in the direction of arrow B to block the path of lancet carrier 208' and thus prevent the forward movement of lancet carrier 208' during the ejection of lancet 104.

An advantage of ejection locking member 750 is that its neutral position is blocking lancet carrier 208'. Thus when ejection actuator 516' is moved forward, the spring-like action of ejection locking member 750 provides for reliable and quick transition to a blocking position.

The above-mentioned embodiments have been described in order to allow easy understanding of the present invention. The invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A lancing device for use with a removable lancet, comprising:
    a housing;
    a lancet carrier slidably disposed within the housing and adapted to receive the lancet;
    an ejection slide mounted to the housing and configured to move a first direction from an at rest position when ejecting the lancet from the lancet carrier and to move a second direction to the at rest position after ejecting the lancet; and
    a locking member comprising a first arm and a second arm, the locking member contacted by the ejection slide to move the locking member into blocking engagement with the lancet carrier to prevent forward movement of the lancet carrier when the ejection slide ejects the lancet, the ejection slide comprising a front-facing surface and a rear-facing surface defining therebetween a recess to receive a portion of the of the second arm when the ejection slide is at the at rest position, the rear-facing surface configured to engage the second arm to move the locking member out of blocking engagement with the lancet carrier when the ejection slide moves in the second direction to the at rest position.

2. The lancing device of claim 1, further comprising a bias element to urge the locking member into blocking engagement with the lancet carrier.

3. The lancing device of claim 1 wherein the lancet carrier continues to urge the locking member in a direction away from the ejection slide when the locking member is in blocking engagement with the lancet carrier.

4. The lancing device of claim 1, wherein the locking member contacts the housing on one or more bearing surfaces apart from the ejection slide, the locking member being configured so that substantially all of the force exerted on it by the lancet carrier is transmitted to the housing via the one or more bearing surfaces.

5. The lancing device of claim 4 wherein:
    the one or more bearing surfaces include a pivot on which the locking member is rotatably mounted to the housing;
    the lancet carrier moves along a longitudinal axis of the housing and further comprises at a front-facing planar surface that forms an angle with the axis of between zero and forty five degrees; and
    the locking member engages the front-facing planar surface to urge the locking member to rotate away from the ejection slide in response to the forward thrust of the lancet carrier.

6. The lancing device of claim 4 wherein the one or more bearing surfaces include a pivot on which the locking member is rotatably mounted to the housing.

7. The lancing device of claim 6 wherein the ejection slide rotates the locking member into blocking engagement with the lancet carrier when the ejection slide ejects the lancet.

8. The lancing device of claim 6 wherein the ejection slide rotates the locking member about the pivot into blocking engagement with the lancet carrier when the ejection slide moves forward to eject the lancet, and rotates the locking member about the pivot out of blocking engagement with the lancet carrier when the ejection slide moves rearward to its at rest position.

9. The lancing device of claim 8 wherein the front-facing surface engages the second arm to rotate the locking member into blocking engagement with the lancet carrier when the ejection slide moves forward from the at rest position.

10. The lancing device of claim 9 where in the front-facing surface is convex.

11. A lancing device for use with a removable lancet, comprising:
    a housing;
    a lancet carrier slidably disposed within the housing and adapted to receive the lancet;
    an ejection slide mounted to the housing and configured to eject the lancet from the lancet carrier, the ejection slide comprising a front-facing surface and a rear-facing surface; and
    a locking member configured to move in a first direction into blocking engagement with the lancet carrier due to contact with the ejection slide when the ejection slide begins to eject the lancet, the locking member comprising a first arm and a second arm, the rear-facing surface configured to directly engage the second arm to rotate the first arm out of blocking engagement with the lancet carrier when the ejection slide moves in a second direction to an at rest position;

wherein the locking member and lancet carrier are configured so that forward thrust of the lancet carrier continues to urge the locking member in the first direction to remain in blocking engagement with the lancet carrier while the ejection slide ejects the lancet.

12. The lancing device of claim 11, wherein the ejection slide comprises a bias member to contact the locking member and urge the locking member into blocking engagement with the lancet carrier.

13. The lancing device of claim 11 wherein the locking member contacts the housing on one or more bearing surfaces apart from the ejection slide, the locking member being configured so that substantially all of a force exerted on it by the lancet carrier is transmitted to the housing via the one or more bearing surfaces.

14. The lancing device of claim 11, further comprising a carriage assembly slidably disposed within the housing and having mounted thereon the lancet carrier and a drive member, wherein the locking member contacts the carriage on one or more bearing surfaces apart from the ejection slide, the locking member being configured so that substantially all of a force exerted on it by the lancet carrier is transmitted to the carriage via the one or more bearing surfaces.

15. The lancing device of claim 11 wherein the locking member is mounted to the housing and comprises a body having an axis and the first arm for rotation about the axis in the first direction to move the locking member into blocking engagement with the lancet carrier, and in the second direction to move the locking member out of blocking engagement with the lancet carrier.

16. The lancing device of claim 15 wherein the ejection slide is configured to move forward from the at rest position when ejecting the lancet and to move rearward to the at rest position after ejecting the lancet, wherein the ejection slide and locking member cooperate to move the first arm about the axis and into blocking engagement with the lancet carrier when the ejection slide moves forward to eject the lancet, and to move the first end about the axis out of blocking engagement with the lancet carrier when the ejection slide moves rearward to its at rest position.

17. The lancing device of claim 15 wherein the front-facing surface and the rear-facing surface of the ejection slide define therebetween a recess to receive the second arm of the locking member when the ejection slide is in the at rest position.

18. The lancing device of claim 17 wherein the front-facing surface engages the second arm to rotate the first armed into blocking engagement with the lancet carrier when the ejection slide moves forward from the at rest position.

* * * * *